United States Patent
Dehmlow et al.

(10) Patent No.: US 7,906,546 B2
(45) Date of Patent: Mar. 15, 2011

(54) TETRAHYDROCARBAZOLES AND DERIVATIVES

(75) Inventors: Henrietta Dehmlow, Grenzach-Wyhlen (DE); Bernd Kuhn, Liestal (CH); Raffaello Masciadri, Basel (CH); Narendra Panday, Basel (CH); Hasane Ratni, Habsheim (FR); Matthew Blake Wright, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/774,779

(22) Filed: May 6, 2010

(65) Prior Publication Data

US 2010/0216833 A1    Aug. 26, 2010

Related U.S. Application Data

(63) Continuation of application No. 11/088,065, filed on Mar. 23, 2005, now abandoned.

(30) Foreign Application Priority Data

Mar. 26, 2004  (EP) .................................. 04101252

(51) Int. Cl.
  *A61K 31/403*  (2006.01)
  *A61K 31/4245*  (2006.01)
  *C07D 209/82*  (2006.01)
(52) U.S. Cl. ......... 514/411; 548/125; 548/143; 548/250; 548/427; 548/439; 514/361; 514/381; 514/383; 514/410
(58) Field of Classification Search .................. 548/125, 548/143, 250, 255, 262.2, 416, 427, 439; 514/361, 381, 383, 410, 411
See application file for complete search history.

(56) References Cited

FOREIGN PATENT DOCUMENTS

| WO | 03/090732 | 11/2003 |
| WO | 03/090746 | 11/2003 |
| WO | 03/099775 | 12/2003 |
| WO | 03/099821 | 12/2003 |
| WO | 2004/011448 | 2/2004 |

OTHER PUBLICATIONS

Willy, et. al., Genes Dev. (1995) 9:1033-45.
Song, et. al., Proc. Natl Acad Sci USA (1994), 91:10809-13.
Miller, NE., Lipids (1978) 13:914-9.
Gordon, et. al., Am. J Med. (1977) 62:707-14.
Lund, et. al., Arterioscler. Thromb. Vasc. Biol. (2003) 23:1169-77.
Joseph & Tontonoz, Curr. Opin. Pharmacol. (2003) 3:192-7.
Cao, et. al., J. Biol Chem (2003) 278:1131-6.

*Primary Examiner* — Golam M Shameem
(74) *Attorney, Agent, or Firm* — George W. Johnston; Dennis P. Tramaloni; Samuel H. Megerditchian

(57) ABSTRACT

The present invention relates to compounds of the formula (I)

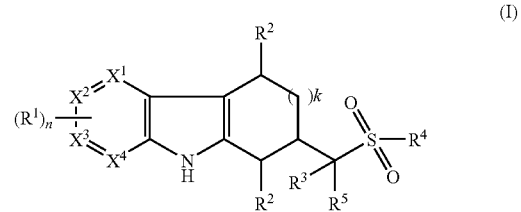

wherein $R^1$, $R^2$, $R^3$, $R^4$, $R^5$, $X^1$, $X^2$, $X^3$, $X^4$, n, and k are defined in the description and claims, and pharmaceutically acceptable salts and/or pharmaceutically acceptable esters thereof. The compounds are useful for in the treatment and prophylaxis of diseases which are modulated by LXRα and/or LXRβ agonists, including increased lipid and cholesterol levels, particularly low HDL-cholesterol, high LDL-cholesterol, atherosclerotic diseases, diabetes, particularly non-insulin dependent diabetes mellitus, metabolic syndrome, dyslipidemia, Alzheimer's disease, sepsis, inflammatory diseases such as colitis, pancreatitis, cholestasis/fibrosis of the liver, and diseases that have an inflammatory component such as Alzheimer's disease or impaired/improvable cognitive function.

35 Claims, No Drawings

TETRAHYDROCARBAZOLES AND DERIVATIVES

PRIORITY TO RELATED APPLICATION(S)

This application is a continuation of U.S. application Ser. No. 11/088,065, filed Mar. 23, 2005, now Pending, which claims the benefit of European Application No. 04101252.7 filed Mar. 26, 2004. The entire contents of the above-identified applications are hereby incorporated by reference.

FIELD OF THE INVENTION

The present invention relates to compounds of the formula (I):

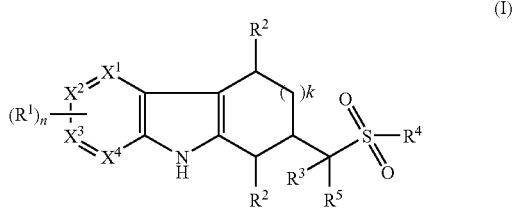

and pharmaceutically acceptable salts and pharmaceutically acceptable esters thereof.

It has been found that the compounds of the present invention are useful as liver-X-modulators.

All documents cited or relied upon below are expressly incorporated herein by reference.

BACKGROUND OF THE INVENTION

Liver-X-Receptors (LXRs) are members of the nuclear hormone receptor superfamily. The LXRs are activated by endogenous oxysterols and regulate the transcription of genes controlling multiple metabolic pathways. Two subtypes, LXRα and LXRβ, have been described (Willy et al., Genes Dev. 1995, 9:1033-45; Song et al., Proc Natl Acad Sci USA. 1994, 91:10809-13). LXRβ is ubiquitously expressed, while LXRα is predominantly expressed in cholesterol metabolizing tissues such as the liver, adipose, intestine and macrophage. The LXRs modulate a variety of physiological responses including regulation of cholesterol absorption, cholesterol elimination (bile acid synthesis), and transport of cholesterol from peripheral tissues via plasma lipoproteins to the liver. The LXRs are also involved in glucose metabolism, cholesterol metabolism in the brain, cell differentiation, and inflammation.

At present, approximately half of all patients with coronary artery disease have low concentrations of plasma high-density lipoprotein cholesterol (HDL-C). The atheroprotective function of HDL was first highlighted almost 25 years ago and stimulated exploration of the genetic and environmental factors that influence HDL-C levels (Miller N E., Lipids 1978, 13:914-9).

The protective function of HDL derives from its role reverse cholesterol transport. HDL mediates the removal of cholesterol from cells in peripheral tissues, including macrophage foam cells in the atherosclerotic lesions of the arterial wall. HDL delivers its cholesterol to the liver and sterol-metabolizing organs for conversion to bile and elimination in feces. Studies have shown that HDL-C levels are predictive of coronary artery disease risk independently of low-density lipoprotein cholesterol (LDL-C) levels (Gordon et al., Am J Med. 1977, 62:707-14).

At present, the estimated age-adjusted prevalence among Americans age 20 and older who have HDL-C of less than 35 mg/dl is 16% (males) and 5.7% (females). A substantial increase of HDL-C is currently achieved by treatment with niacin in various formulations. However, the substantial unfavorable side-effects limit the therapeutic potential of this approach.

It has been observed that as many as 90% of the 14 million diagnosed type 2 diabetic patients in the United States are overweight or obese, and a high proportion of type 2 diabetic patients have abnormal concentrations of lipoproteins. Studies have shown that the prevalence of total cholesterol >240 mg/dl is 37% in diabetic men and 44% in women. The rates for LDL-C >160 mg/dl are 31% and 44%, and for HDL-C <35 mg/dl are 28% and 11%, in diabetic men and women respectively. Diabetes is a disease in which a patient's ability to control glucose levels in blood is decreased because of partial impairment in response to the action of insulin. Type II diabetes (T2D) is also called non-insulin dependent diabetes mellitus (NIDDM) and has been shown to afflict 80-90% of all diabetic patients in developed countries. In T2D, the pancreatic Islets of Langerhans continue to produce insulin. However, the target organs for insulin action, mainly muscle, liver and adipose tissue, exhibit a profound resistance to insulin stimulation. The body continues to compensate by producing unphysiologically high levels of insulin, which ultimately decreases in the later stages of the disease, due to exhaustion and failure of pancreatic insulin-producing capacity. Thus, T2D is a cardiovascular-metabolic syndrome associated with multiple co-morbidities, including insulin resistance, dyslipidemia, hypertension, endothelial dysfunction and inflammatory atherosclerosis.

The first line of treatment for dyslipidemia and diabetes at present generally involves a low-fat and low-glucose diet, exercise and weight loss. However, compliance can be moderate, and as the disease progresses, treatment of the various metabolic deficiencies becomes necessary with lipid-modulating agents such as statins and fibrates for dyslipidemia, and hypoglycemic drugs, e.g. sulfonylureas, metformin, or insulin sensitizers of the thiazolidinedione (TZD) class of PPARγ-agonists, for insulin resistance. Recent studies provide evidence that modulators of LXRs would result in compounds with enhanced therapeutic potential, and as such, modulators of LXRs should improve the plasma lipid profile, and raise HDL-C levels (Lund et al., Arterioscler. Thromb. Vasc. Biol. 2003, 23:1169-77). LXRs are also known to control the efflux of cholesterol from the macrophage foam cell of the atherosclerotic lesion, and agonists of LXRs have been shown to be atheroprotective (Joseph and Tontonoz, Curr. Opin. Pharmacol. 2003, 3:192-7). Thus, modulators of LXRs would be effective treatments for the atherosclerotic disease which underlies the cardiovascular morbidity and mortality of stroke and heart disease.

Recent observations also suggest that there is an independent LXR mediated effect on insulin-sensitization in addition to its role in atheroprotection (Cao et al., J Biol Chem. 2003, 278:1131-6). Thus LXR modulators can also show superior therapeutic efficacy on HDL-raising and atheroprotection, with additional effects on diabetes, compared to current therapies.

SUMMARY OF THE INVENTION

In one embodiment of the invention, provided are compounds of the formula (I):

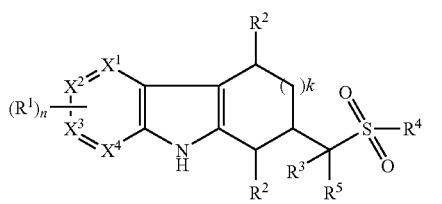

wherein n is an integer selected from 0 to 3;

$R^1$ is independently selected from the group consisting of halogen, —CN, —NO$_2$, —SO$_2$Me, lower alkyl, trifluoromethoxy, —OR$^{11}$, piperidinyl, pyrrolidinyl, and —N(R$^{11}$)(R$^{11}$), wherein R$^{11}$ is independently selected from lower alkyl and H, $X^1$, $X^2$, $X^3$, and $X^4$ are independently selected from nitrogen and carbon, provided that no more than two of $X^1$, $X^2$, $X^3$, and $X^4$ can be nitrogen at one time, and when two of $X^1$, $X^2$, $X^3$, and $X^4$ are nitrogen, n is 0, 1, or 2;

k is an integer from 0 to 1;

$R^2$ is H;

$R^3$ is H, alkyl, or halogen;

$R^4$ is aryl, heteroaryl, alkylaryl or alkylheteroaryl, all being optionally substituted with from one to five substituents independently selected from the group consisting of halogen, alkyl, —OR$^{41}$, lower alkynyl, and NR$^{42}$R$^{43}$, wherein R$^{41}$ is lower alkyl or —H, R$^{42}$ and R$^{43}$ independently from each other are hydrogen or alkyl, or NR$^{42}$R$^{43}$ is piperidinyl or pyrrolidinyl, or R$^4$ is alkyl;

$R^5$ is selected from the group consisting of

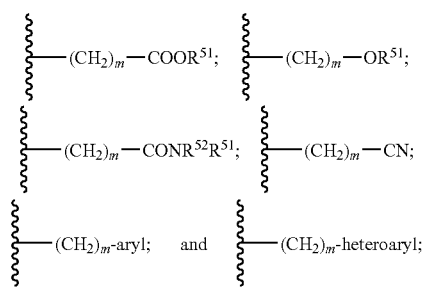

said aryl and heteroaryl being optionally substituted at one or more positions with one or more substituents independently selected from the group consisting of H, halogen, lower alkyl and (CH$_2$)$_v$R$^{53}$, wherein $R^{51}$ is selected from the group consisting of H, alkyl, lower alkenyl and alkylaryl, said alkylaryl being optionally substituted at one or more positions with one or more of lower alkyl, —CN, halogen, —COOR$^{54}$, and —CH$_2$OR$^{54}$, wherein R$^{54}$ is alkyl or —H;

$R^{52}$ is lower alkyl or —H;

$R^{53}$ is H, alkyl, cycloalkyl, —COOR$^{55}$, —N(R$^{55}$)(R$^{56}$), —CH$_2$OH, —CN, CF$_3$, —CONH$_2$, —CH$_2$OR$^{55}$ or —CONR$^{55}$R$^{56}$, wherein R$^{55}$ is independently selected from the group consisting of alkyl, —H, —C(O)-aryl, —C(O)-alkyl, or —C(O)-heteroaryl, and R$^{56}$ is selected from the group consisting of H, alkyl, C(O)CF$_3$, —C(O)-aryl, —C(O)-alkyl, —C(O)-heteroaryl, alkylaryl and alkylheteroaryl, and wherein said aryl, heteroaryl, alkylaryl and alkyl-heteroaryl are optionally substituted at one or more positions with one or more of alkyl, —CN, halogen, —COOR$^{57}$, and —CH$_2$OR$^{57}$, wherein R$^{57}$ is lower alkyl or —H, or R$^{55}$ and R$^{56}$ together with the atom to which they are attached form a ring;

or $R^{53}$ is aryl which can optionally be substituted with benzyloxy, carboxy, lower-alkoxy-carbonyl, hydroxy-lower-alkyl, halogen, carbamoyl, lower-alkyl-carbamoyl, di-lower-alkyl-carbamoyl, m is an integer selected from 0 to 2;

v is an integer selected from 0 to 4;

and pharmaceutically-acceptable salts and/or pharmaceutically-acceptable esters thereof.

In other embodiments of the invention, provided are uses of such compounds as therapeutic active substances as well as their use for the preparation of medicaments for the treatment or prophylaxis of diseases which are modulated by LXRα and/or LXRβ agonists

DETAILED DESCRIPTION OF THE INVENTION

The novel compounds of the present invention have been found to bind to and selectively activate LXRα or LXRβ or coactivate LXRα and LXRβ. Consequently, cholesterol absorption is reduced, HDL cholesterol is increased, and inflammatory atherosclerosis is reduced. Since multiple facets of combined dyslipidemia and cholesterol homeostasis are addressed by LXR modulators, novel compounds of the present invention have an enhanced therapeutic potential compared to the compounds already known in the art. They can therefore be used in the treatment and prophylaxis of diseases which are modulated by LXRα and/or LXRβ agonists. Such diseases include increased lipid and cholesterol levels, particularly low HDL-cholesterol, high LDL-cholesterol, atherosclerotic diseases, diabetes, particularly non-insulin dependent diabetes mellitus, metabolic syndrome, dyslipidemia, Alzheimer's disease, sepsis, and inflammatory diseases such as colitis, pancreatitis, cholestasis/fibrosis of the liver, and diseases that have an inflammatory component such as Alzheimer's disease or impaired/improvable cognitive function. The novel compounds of the present can further be used for treatment and prophylaxis of age-related macular degeneration.

The present invention also relates to pharmaceutical compositions comprising a compound of formula I and a pharmaceutically acceptable carrier and/or adjuvant. Furthermore, the present invention relates to the use of such compounds as therapeutic active substances as well as their use for the preparation of medicaments for the treatment or prophylaxis of diseases which are modulated by LXRα and/or LXRβ agonists. The invention further relates to processes for the preparation of the compounds of formula I. In addition, the present invention relates to a method for the prophylaxis or therapeutic treatment of diseases modulated by LXRα and/or LXRβ agonist, such as increased lipid and cholesterol levels, particularly low HDL-cholesterol, high LDL-cholesterol, atherosclerotic diseases, diabetes, particularly non-insulin dependent diabetes mellitus, metabolic syndrome, dyslipidemia, Alzheimer's disease, sepsis, and inflammatory diseases such as colitis, pancreatitis, cholestasis/fibrosis of the liver, and diseases that have an inflammatory component such as Alzheimer's disease or impaired/improvable cognitive function, said method comprising administering a compound of formula I to a human being or animal.

In more detail, the invention relates to compounds of the formula (I)

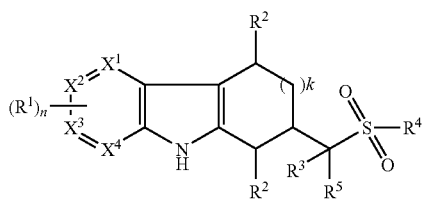

wherein
n is an integer selected from 0 to 3;
R$^1$ is independently selected from the group consisting of halogen, —CN, —NO$_2$,
—SO$_2$Me, lower alkyl, trifluoromethoxy, —OR$^{11}$, piperidinyl, pyrrolidinyl, and —N(R$^{11}$)(R$^{11}$), wherein R$^{11}$ is independently selected from lower alkyl and H,
X$^1$, X$^2$, X$^3$, and X$^4$ are independently selected from nitrogen and carbon, provided that no more than two of X$^1$, X$^2$, X$^3$, and X$^4$ can be nitrogen at one time, and when two of X$^1$, X$^2$, X$^3$, and X$^4$ are nitrogen, n is 0, 1, or 2;
k is an integer from 0 to 1;
R$^2$ is H;
R$^3$ is H, alkyl, or halogen;
R$^4$ is aryl, heteroaryl, alkylaryl or alkylheteroaryl, all being optionally substituted with from one to five substituents independently selected from the group consisting of halogen, alkyl, —OR$^{41}$, lower alkynyl, and NR$^{42}$R$^{43}$, wherein R$^{41}$ is lower alkyl or —H, R$^{42}$ and R$^{43}$ independently from each other are hydrogen or alkyl, or NR$^{42}$R$^{43}$ is piperidinyl or pyrrolidinyl, or R$^4$ is alkyl;
R$^5$ is selected from the group consisting of

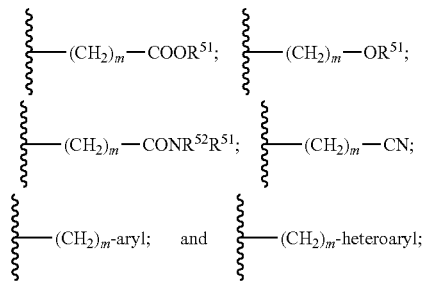

said aryl and heteroaryl being optionally substituted at one or more positions with one or more substituents independently selected from the group consisting of H, halogen, lower alkyl and (CH$_2$)$_v$R$^{53}$, wherein
R$^{51}$ is selected from the group consisting of H, alkyl, lower alkenyl and alkylaryl, said alkylaryl being optionally substituted at one or more positions with one or more of lower alkyl, —CN, halogen, —COOR$^{54}$, and —CH$_2$OR$^{54}$, wherein R$^{54}$ is alkyl or —H;
R$^{52}$ is lower alkyl or —H;
R$^{53}$ is H, alkyl, cycloalkyl, —COOR$^{55}$, —N(R$^{55}$)(R$^{56}$), —CH$_2$OH, —CN, CF$_3$, —CONH$_2$,
—CH$_2$OR$^{55}$ or —CONR$^{55}$R$^{56}$, wherein R$^{55}$ is independently selected from the group consisting of alkyl, —H, —C(O)-aryl, —C(O)-alkyl, or —C(O)-heteroaryl, and R$^{56}$ is selected from the group consisting of H, alkyl, C(O)CF$_3$, —C(O)-aryl, —C(O)-alkyl,
—C(O)-heteroaryl, alkylaryl and alkylheteroaryl, and wherein said aryl, heteroaryl, alkylaryl and alkyl-heteroaryl are optionally substituted at one or more positions with one or more of alkyl, —CN, halogen, —COOR$^{57}$, and —CH$_2$OR$^{57}$, wherein R$^{57}$ is lower alkyl or —H, or R$^{55}$ and R$^{56}$ together with the atom to which they are attached form a ring;
or R$^{53}$ is aryl which can optionally be substituted with benzyloxy, carboxy, lower-alkoxy-carbonyl, hydroxy-lower-alkyl, halogen, carbamoyl, lower-alkyl-carbamoyl, di-lower-alkyl-carbamoyl,
m is an integer selected from 0 to 2;
v is an integer selected from 0 to 4;
and pharmaceutically-acceptable salts and/or pharmaceutically-acceptable esters thereof.
Preferred compounds of formula (I) as defined above are those, wherein
n is an integer selected from 0 to 3;
R$^1$ is independently selected from the group consisting of halogen, —CN, —NO$_2$,
—SO$_2$Me, lower alkyl, trifluoromethoxy, —OR$^{11}$, and —N(R$^{11}$)(R$^{11}$), wherein R$^{11}$ is independently selected from lower alkyl and H;
X$^1$, X$^2$, X$^3$, and X$^4$ are independently selected from nitrogen and carbon, provided that no more than two of X$_1$, X$_2$, X$_3$, and X$_4$ can be nitrogen at one time, and when two of X$_1$, X$_2$, X$_3$, and X$_4$ are nitrogen, n is 0, 1, or 2;
k is an integer from 0 to 1;
R$^2$ is H;
R$^3$ is H, alkyl, or halogen;
R$^4$ is aryl, heteroaryl, alkylaryl or alkylheteroaryl, all being optionally substituted with from one to five substituents independently selected from the group consisting of halogen, alkyl and —OR$^{41}$, wherein R$^{41}$ is lower alkyl or —H, or R$^4$ is alkyl;
R$^5$ is selected from the group consisting of

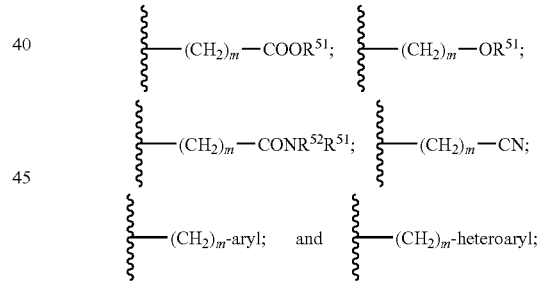

said aryl and heteroaryl being optionally substituted at one or more positions with one or more substituents independently selected from the group consisting of H, halogen, lower alkyl and (CH$_2$)$_v$R$^{53}$, wherein
R$^{51}$ is selected from the group consisting of H, alkyl, allyl and alkylaryl, said alkylaryl being optionally substituted at one or more positions with one or more of lower alkyl, —CN, halogen, —COOR$^{54}$, and —CH$_2$OR$^{54}$, wherein R$^{54}$ is alkyl or —H;
R$^{52}$ is lower alkyl or —H;
R$^{53}$ is H, alkyl, cycloalkyl, —COOR$^{55}$, —N(R$^{55}$)(R$^{56}$), —CH$_2$OH, —CN, —CONH$_2$, —CH$_2$OR$^{55}$ or —CONR$^{55}$R$^{56}$, wherein R$^{55}$ is independently selected from the group consisting of alkyl, —H, —C(O)-aryl, —C(O)-alkyl, or —C(O)-heteroaryl, and R$^{56}$ is selected from the group consisting of H, alkyl, —C(O)-aryl, —C(O)-alkyl, —C(O)-heteroaryl, alkylaryl and alkylheteroaryl, and wherein said aryl, heteroaryl, alkylaryl and alkyl-heteroaryl are optionally substituted at one or more positions with one or more of alkyl, —CN, halogen, —COOR$^{57}$, and —CH$_2$OR$^{57}$, wherein R$^{57}$ is lower alkyl or —H, or R$^{55}$ and R$^{56}$ taken together with the atom to which they are attached form a ring;

m is an integer selected from 0 to 2;

v is an integer selected from 0 to 4;

and pharmaceutically-acceptable salts and/or pharmaceutically-acceptable esters thereof.

Unless otherwise indicated, the following definitions are set forth to illustrate and define the meaning and scope of the various terms used to describe the invention herein.

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower alkyl", alone or in combination with other groups, refers to a branched or straight-chain monovalent alkyl radical of one to six carbon atoms, preferably one to four carbon atoms. This term is further exemplified by such radicals as methyl, ethyl, n-propyl, isopropyl, n-butyl, s-butyl, t-butyl and the like.

The term "lower alkenyl", alone or in combination, signifies a straight-chain or branched hydrocarbon residue comprising an olefinic bond and 2 to 8, preferably 2 to 6, particularly preferred 2 to 4 carbon atoms. Examples of alkenyl groups are ethenyl, 1-propenyl, 2-propenyl, isopropenyl, 1-butenyl, 2-butenyl, 3-butenyl, 3-methyl-but-2-enyl and isobutenyl.

The term "lower alkynyl", alone or in combination with other groups, stands for a straight-chain or branched hydrocarbon residue comprising a triple bond and up to 7, preferably up to 4 carbon atoms, such as e.g. 2-propinyl or ethinyl.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl.

The term "aryl" refers to either an aromatic monocyclic system containing six carbon atoms or an aromatic bicyclic system containing 10 carbon atoms. For example, the term aryl includes a phenyl or naphthyl ring system, preferably the phenyl group. The term "alkylaryl" refers to an aryl group which is bound via an alkyl group, e.g. benzyl.

The term "heteroaryl" refers to an aromatic 5- or 6-membered ring which can comprise 1-4 heteroatoms selected from nitrogen, oxygen and/or sulphur, such as furyl, pyridyl, pyridazinyl, pyrimidinyl, pyrazinyl, thienyl, isoxazolyl, oxazolyl, imidazolyl, or pyrrolyl. The term "heteroaryl" also includes a heteroaryl as defined above fused to one or more other cycle be it a heterocycle, aryl, or heteroaryl, for example benzothiazolyl. The term "alkylheteroaryl" refers to a heteroaryl group which is bound via an alkyl group.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, p-toluenesulphonic acid and the like, which are non toxic to living organisms.

Preferred salts are phosphates, citrates, fumarates, formates, hydrochlorides, hydrobromides and methanesulfonic acid salts.

The term "pharmaceutically acceptable esters" embraces esters of the compounds of formula (I), in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

Preferred are compounds of formula (I) wherein each of $X^1$, $X^2$, $X^3$, and $X^4$ are carbon. Also preferred are compounds of formula (I), wherein $X^1$ is nitrogen and each of $X^2$, $X^3$, and $X^4$ is carbon.

In another embodiment, compounds of formula (I) are preferred wherein n is 1, $X^2$ is carbon and $R^1$ is directly attached to the $X^2$ carbon. Compounds wherein $R^1$ is selected from the group consisting of halogen, preferably Cl, cyano, nitro, SO$_2$Me, lower alkyl, and N(Me)$_2$ are more particulary preferred. Another preferred embodiment relates to compounds wherein $R^1$ is selected from the group consisting of halogen, cyano, nitro, SO$_2$Me, lower alkyl, N(Me)$_2$, NHMe and piperidinyl.

Also preferred are compounds according to formula (I), wherein $R^1$ is halogen. Particularly preferred are those compounds of formula (I), wherein $R^1$ is Cl.

Further preferred compounds of formula (I) are those, wherein n is 2.

In another embodiment, compounds of formula (I) are preferred wherein n is 2, and each $R^1$ is halogen. More preferably, $X^2$ is carbon, and one of the two $R^1$ groups is directly attached to the $X^2$ carbon.

In yet another preferred embodiment, compounds of formula (I) are preferred wherein k is 0 or 1, more preferably wherein k is 0. Compounds wherein k is 0 and wherein k is 1 individually constitute preferred embodiments.

In another preferred embodiment of the present invention, $R^3$ of formula (I) is H, halogen or methyl. Preferably, $R^3$ is F or methyl. F and methyl individually constitute preferred embodiments.

Another preferred embodiment relates to compounds as defined above, wherein $R^4$ is aryl or heteroaryl, all being optionally substituted with from one to five substituents independently selected from the group consisting of halogen, alkyl, —OR$^{41}$, lower alkynyl, and NR$^{42}$R$^{43}$, wherein R$^{41}$ is lower alkyl or —H, R$^{42}$ and R$^{43}$ independently from each other are hydrogen or alkyl, or NR$^{42}$R$^{43}$ is piperidinyl or pyrrolidinyl, or R$^4$ is lower alkyl Compounds as defined above, wherein $R^4$ is selected from the group consisting of napthyl, pyridinyl, methyl, phenyl or mono-or di-substituted phenyl, wherein the phenyl substituents are halogen, N(lower alkyl)$_2$ or OR$^{41}$, and wherein R$^{41}$ is defined as above, are also preferred.

Also preferred are those compounds of formula (I), wherein $R^4$ is aryl, heteroaryl, or lower alkyl.

Further preferred compounds of formula (I) are those, wherein $R^4$ is selected from the group consisting of napthyl, pyridinyl, methyl, phenyl or mono-or di-substituted phenyl, wherein the phenyl substituents are halo or OR$^{41}$, and wherein R$^{41}$ is lower alkyl or hydrogen.

Further preferred compounds of the present invention are those wherein $R^4$ is aryl or heteroaryl which is optionally substituted at one or more positions with lower alkyl. More particularly, compounds wherein $R^4$ is selected from the group consisting of phenyl; mono-or di-substituted phenyl wherein the one or more substituents are halo or OR$^{41}$; naphthyl; pyridinyl; or methyl are preferred. More particularly, compounds of formula (I) are preferred wherein $R^4$ is phenyl, or mono- or di-substituted phenyl wherein the one or more substituents is halogen, more preferably $R^4$ is phenyl, 4-chlorophenyl, 3-fluorophenyl, or 3,4-difluorophenyl. Another preferred embodiment of the present invention relates to compounds as described above, wherein $R^4$ is phenyl, 3-bromophenyl or 3-dimethylaminophenyl.

In yet another preferred embodiment of compounds of formula (I) of the present invention, $R^5$ is selected from the group consisting of

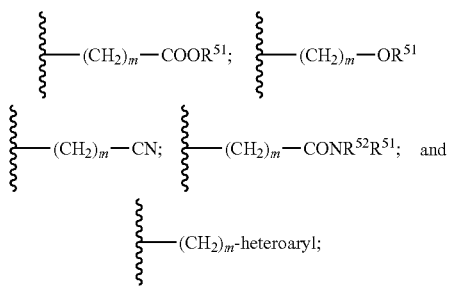

said heteroaryl being optionally substituted at one or more positions with one or more substituents independently selected from the group consisting of H, halogen, lower alkyl and $(CH_2)_v R^{53}$, wherein $R^{51}$ is selected from the group consisting of H, alkyl, and alkylaryl, said alkylaryl being optionally substituted at one or more positions with one or more of lower alkyl, —CN, halogen, —COOR$^{54}$, and —CH$_2$OR$^{54}$, wherein $R^{54}$ is alkyl or —H; $R^{52}$ is lower alkyl or —H; $R^{53}$ is H, alkyl, cycloalkyl, —COOR$^{55}$, —N(R$^{55}$)(R$^{56}$), —CH$_2$OH, —CN, —CONH$_2$, —CH$_2$OR$^{55}$ or —CONR$^{55}$R$^{56}$, wherein $R^{55}$ is independently selected from the group consisting of alkyl, —H, —C(O)-aryl, —C(O)-alkyl, or —C(O)-heteroaryl, and $R^{56}$ is selected from the group consisting of H, alkyl, —C(O)-aryl, —C(O)-alkyl, —C(O)-heteroaryl, alkylaryl and alkylheteroaryl, and wherein said aryl, heteroaryl, alkylaryl and alkyl-heteroaryl are optionally substituted at one or more positions with one or more of alkyl, —CN, halogen, —COOR$^{57}$, and —CH$_2$OR$^{57}$, wherein $R^{57}$ is lower alkyl or —H, or $R^{55}$ and $R^{56}$ taken together with the atom to which they are attached form a ring; m is an integer selected from 0 to 2; and v is an integer selected from 0 to 4. In a preferred embodiment, m is 0.

In yet another preferred embodiment of compounds of the present invention, $R^5$ is selected from the group consisting of

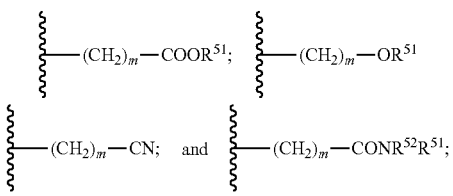

wherein $R^{51}$ is selected from the group consisting of H; alkyl; alkylaryl optionally mono- or di-substituted at with one or more of lower alkyl, —CN, halogen, or —COOR$^{54}$ wherein $R^{54}$ is alkyl or —H; and $R^{52}$ is lower alkyl or H and, wherein m is defined as before.

Alternatively, compounds of formula (I) wherein $R^5$ is selected from the group consisting of

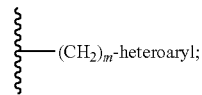

said heteroaryl being optionally substituted at one or more positions with one or more substituents independently selected from the group consisting of H, halogen, lower alkyl and $(CH_2)_v R^{53}$ are also preferred, wherein m, v and $R^{53}$ are defined as before. More preferably, the heteroaryl is selected from the group consisting of

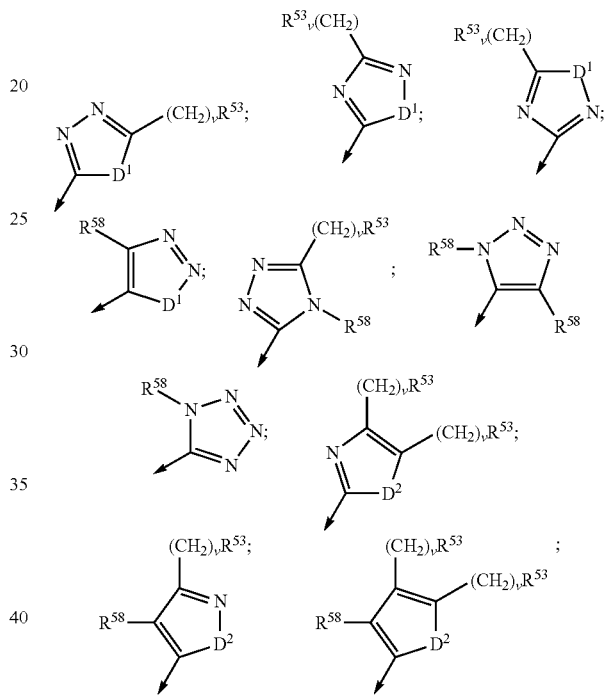

wherein v and $R^{53}$ are defined as before, $R^{58}$ is independently selected from H, halogen and lower alkyl, $D^1$ is O or S, and $D^2$ is O, S, or NR$^{58}$, and wherein, when said compound contains two $(CH_2)_v R^{53}$ groups, said groups may be optionally joined together along with the atoms to which they are attached to form a ring.

In an alternative preferred embodiment, preferred compounds of formula (I) are those wherein $R^5$ is selected from the group consisting of

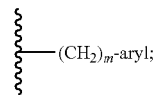

wherein aryl is selected from the group consisting of:

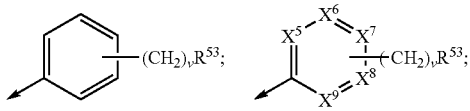

wherein $R^{53}$ is described as before, and wherein $X^5$, $X^6$, $X^7$, $X^8$ and $X^9$ are selected from carbon and nitrogen with the proviso that no more than two of $X^5$, $X^6$, $X^7$, $X^8$ and $X^9$ can be N at one time, and wherein m and v are defined as before. Preferably, m is 0. Preferably, aryl is phenyl substituted with —$(CH_2)_v R^{53}$, wherein $R^{53}$ and v are as described above.

Preferred compounds as defined above are those, wherein $R^5$ is a heteroaryl selected from the group consisting of oxadiazolyl, oxazolyl and benzothiazolyl, which heteroaryl is optionally substituted with lower alkyl, lower alkoxy carbonyl or phenyl, which phenyl is optionally substituted with carboxy, lower alkyl carbonyl, carbamoyl or di (lower alkyl) carbamoyl. More preferred are those compounds, wherein $R^5$ is 5-methyl-(1,3,4)oxadiazol-2-yl, 5-(4-benzoic acid methyl ester)-(1,3,4)oxadiazol-2-yl, 5-(4-benzoic acid)-(1,3,4)oxadiazol-2-yl, 5-(4-benzamide)-(1,3,4)oxadiazol-2-yl, 5-(4-dimethylbenzamide)-(1,3,4)oxadiazol-2-yl, 4-(carboxylic acid methyl ester)-oxazo-2-yl or benzothiazol-2-yl.

Preferred compounds of formula (I) are those of formula (Ia)

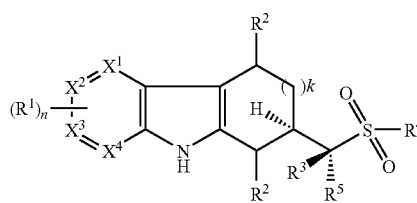

(Ia)

wherein $R^1$, $R^2$, $R^3$, $R^4$, $R^5$, n, k, $X^1$, $X^2$, $X^3$ and $X^4$ are defined as before. Preferably, $R^3$ is halogen or alkyl.

Further preferred compounds of formula (I) are those of formula (Ib)

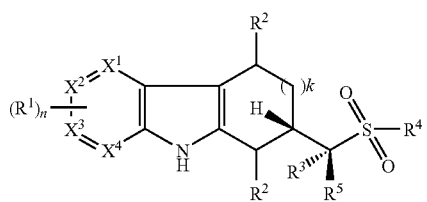

(Ib)

wherein $R^1$, $R^2$, $R^3$, $R^4$, $R^5$, n, k, $X^1$, $X^2$, $X^3$ and $X^4$ are defined as before. Preferably, $R^3$ is halogen or alkyl.

Particular preferred are those compounds of formula (I), wherein m is zero.

Preferred compounds of general formula (I) are those selected from the group consisting of
Benzenesulfonyl-(6-chloro-2,3,4,9-tetrahydro-1H-carbazol-2-yl)-acetic acid methyl ester;
Benzenesulfonyl-(6-fluoro-2,3,4,9-tetrahydro-1H-carbazol-2-yl)-acetic acid methyl ester;
(RS,SR)-2-Benzenesulfonyl-2-(6-chloro-2,3,4,9-tetrahydro-1H-carbazol-2-yl)-propionic acid methyl ester;
(RS,SR)-2-Benzenesulfonyl-2-(6-fluoro-2,3,4,9-tetrahydro-1H-carbazol-2-yl)-propionic acid methyl ester;
(RS,SR)-2-Benzenesulfonyl-2-(6-methyl-2,3,4,9-tetrahydro-1H-carbazol-2-yl)-propionic acid methyl ester;
(RS,SR)-2-Benzenesulfonyl-2-(6-nitro-2,3,4,9-tetrahydro-1H-carbazol-2-yl)-propionic acid methyl ester;
(RS,SR)-2-Benzenesulfonyl-2-(6-cyano-2,3,4,9-tetrahydro-1H-carbazol-2-yl)-propionic acid methyl ester;
(RS,SR)-2-Benzenesulfonyl-2-(2-chloro-6,7,8,9-tetrahydro-5H-pyrido[3,2-b]indol-7-yl)-propionic acid methyl ester;
(RS,SR)-2-Benzenesulfonyl-2-(2,3,4,9-tetrahydro-1H-carbazol-2-yl)-propionic acid methyl ester;
(RS,SR)-2-Benzenesulfonyl-2-(6-methanesulfonyl-2,3,4,9-tetrahydro-1H-carbazol-2-yl)-propionic acid methyl ester;
(RS,SR)-2-Benzenesulfonyl-2-(8-fluoro-2,3,4,9-tetrahydro-1H-carbazol-2-yl)-propionic acid methyl ester;
(RS,SR)-Benzenesulfonyl-(6-chloro-2,3,4,9-tetrahydro-1H-carbazol-2-yl)-fluoro-acetic acid methyl ester;
(RS,SR)-Benzenesulfonyl-fluoro-(6-methyl-2,3,4,9-tetrahydro-1H-carbazol-2-yl)-acetic acid methyl ester;
(RS,SR)-Benzenesulfonyl-(6-cyano-2,3,4,9-tetrahydro-1H-carbazol-2-yl)-fluoro-acetic acid methyl ester;
(RS,SR)-Benzenesulfonyl-(6-bromo-2,3,4,9-tetrahydro-1H-carbazol-2-yl)-fluoro-acetic acid methyl ester;
(RS,SR)-Benzenesulfonyl-(2-chloro-6,7,8,9-tetrahydro-5H-pyrido[3,2-b]indol-7-yl)-fluoro-acetic acid methyl ester;
(RS,SR)-Benzenesulfonyl-(6-bromo-7-fluoro-2,3,4,9-tetrahydro-1H-carbazol-2-yl)-fluoro-acetic acid methyl ester;
(RS,SR)-Benzenesulfonyl-(6-bromo-5-fluoro-2,3,4,9-tetrahydro-1H-carbazol-2-yl)-fluoro-acetic acid methyl ester;
(RS,SR)-2-Benzenesulfonyl-2-(7-chloro-1,2,3,4-tetrahydro-cyclopenta[b]indol-2-yl)-propionic acid methyl ester;
(RS,SR)-2-Benzenesulfonyl-2-(7-bromo-1,2,3,4-tetrahydro-cyclopenta[b]indol-2-yl)-propionic acid methyl ester;
(RS,SR)-2-Benzenesulfonyl-2-(7-cyano-1,2,3,4-tetrahydro-cyclopenta[b]indol-2-yl)-propionic acid methyl ester;
(RS,SR)-2-Benzenesulfonyl-2-(7-methyl-1,2,3,4-tetrahydro-cyclopenta[b]indol-2-yl)-propionic acid methyl ester;
(RS,SR)-Benzenesulfonyl-(7-chloro-1,2,3,4-tetrahydro-cyclopenta[b]indol-2-yl)-fluoro-acetic acid methyl ester;
(RS,SR)-Benzenesulfonyl-(7-bromo-1,2,3,4-tetrahydro-cyclopenta[b]indol-2-yl)-fluoro-acetic acid methyl ester;
(RS,SR)-Benzenesulfonyl-(5-chloro-1,2,3,8-tetrahydro-4,8-diaza-cyclopenta[a]inden-2-yl)-fluoro-acetic acid methyl ester;
(RS,SR)-Benzenesulfonyl-(7-bromo-6-fluoro-1,2,3,4-tetrahydro-cyclopenta[b]indol-2-yl)-fluoro-acetic acid methyl ester;
(RS,SR)-Benzenesulfonyl-(7-bromo-8-fluoro-1,2,3,4-tetrahydro-cyclopenta[b]indol-2-yl)-fluoro-acetic acid methyl ester;
(RS,SR)-2-(6-Chloro-2,3,4,9-tetrahydro-1H-carbazol-2-yl)-2-(naphthalene-1-sulfonyl)propionic acid methyl ester;
(RS,SR)-2-(6-Chloro-2,3,4,9-tetrahydro-1H-carbazol-2-yl)-2-(naphthalene-2-sulfonyl)propionic acid methyl ester;
(RS,SR)-2-(6-Chloro-2,3,4,9-tetrahydro-1H-carbazol-2-yl)-2-(3,4-dichloro-benzenesulfonyl)-propionic acid methyl ester;
(RS,SR)-2-(6-Chloro-2,3,4,9-tetrahydro-1H-carbazol-2-yl)-2-(toluene-3-sulfonyl)-propionic acid methyl ester;
(RS,SR)-2-(6-Chloro-2,3,4,9-tetrahydro-1H-carbazol-2-yl)-2-(3-methoxy-benzenesulfonyl)-propionic acid methyl ester;
(RS,SR)-2-(2-Chloro-benzenesulfonyl)-2-(6-chloro-2,3,4,9-tetrahydro-1H-carbazol-2-yl)-propionic acid methyl ester;
(RS,SR)-2-(6-Chloro-2,3,4,9-tetrahydro-1H-carbazol-2-yl)-2-(2-methoxy-benzenesulfonyl)-propionic acid methyl ester;
(RS,SR)-2-(6-Chloro-2,3,4,9-tetrahydro-1H-carbazol-2-yl)-2-(4-fluoro-benzenesulfonyl)-propionic acid methyl ester;
(RS,SR)-2-(3-Chloro-benzenesulfonyl)-2-(6-chloro-2,3,4,9-tetrahydro-1H-carbazol-2-yl)-propionic acid methyl ester;

(RS,SR)-(6-Chloro-2,3,4,9-tetrahydro-1H-carbazol-2-yl)-fluoro-(4-fluoro-benzenesulfonyl)-acetic acid methyl ester;
(RS,SR)-(3-Chloro-benzenesulfonyl)-(6-chloro-2,3,4,9-tetrahydro-1H-carbazol-2-yl)-fluoro-acetic acid methyl ester;
(RS,SR)-(6-Chloro-2,3,4,9-tetrahydro-1H-carbazol-2-yl)-fluoro-(3-fluoro-benzenesulfonyl)-acetic acid methyl ester;
(RS,SR)-(6-Chloro-2,3,4,9-tetrahydro-1H-carbazol-2-yl)-(3,4-difluoro-benzenesulfonyl)-fluoro-acetic acid methyl ester;
(RS,SR)-(6-Chloro-2,3,4,9-tetrahydro-1H-carbazol-2-yl)-fluoro-(pyridine-3-sulfonyl)-acetic acid methyl ester;
(RS,SR)-(7-Chloro-1,2,3,4-tetrahydro-cyclopenta[b]indol-2-yl)-fluoro-(3-methoxy-benzenesulfonyl)-acetic acid methyl ester;
(RS,SR)-(3-Chloro-benzenesulfonyl)-(7-chloro-1,2,3,4-tetrahydro-cyclopenta[b]indol-2-yl)-fluoro-acetic acid methyl ester;
(RS,SR)-(7-Chloro-1,2,3,4-tetrahydro-cyclopenta[b]indol-2-yl)-fluoro-(pyridine-2-sulfonyl)-acetic acid methyl ester;
(RS,SR)-(7-Chloro-1,2,3,4-tetrahydro-cyclopenta[b]indol-2-yl)-fluoro-(3-fluoro-benzenesulfonyl)-acetic acid methyl ester;
(RS,SR)-(7-Chloro-1,2,3,4-tetrahydro-cyclopenta[b]indol-2-yl)-(3,4-difluoro-benzenesulfonyl)-fluoro-acetic acid methyl ester;
(RS,SR)-(7-Chloro-1,2,3,4-tetrahydro-cyclopenta[b]indol-2-yl)-fluoro-(pyridine-3-sulfonyl)-acetic acid methyl ester;
(RS,SR)-2-(7-Chloro-1,2,3,4-tetrahydro-cyclopenta[b]indol-2-yl)-2-(pyridine-2-sulfonyl)-propionic acid methyl ester;
(RS,SR)-2-Benzenesulfonyl-2-(6-chloro-2,3,4,9-tetrahydro-1H-carbazol-2-yl)-propionic acid;
(RS,SR)-Benzenesulfonyl-(6-chloro-2,3,4,9-tetrahydro-1H-carbazol-2-yl)-fluoro-acetic acid;
(RS,SR)-2-(1-Benzenesulfonyl-2-methoxy-1-methyl-ethyl)-6-chloro-2,3,4,9-tetrahydro-1H-carbazole;
(RS,SR)-2-Benzenesulfonyl-2-(6-methyl-2,3,4,9-tetrahydro-1H-carbazol-2-yl)-propionitrile;
(RS,SR)-2-Benzenesulfonyl-2-(6-chloro-2,3,4,9-tetrahydro-1H-carbazol-2-yl)-propionitrile;
(RS,SR)-Benzenesulfonyl-(6-chloro-2,3,4,9-tetrahydro-1H-carbazol-2-yl)-fluoro-acetonitrile;
(RS,SR)-2-Benzenesulfonyl-2-(6-chloro-2,3,4,9-tetrahydro-1H-carbazol-2-yl)-2-fluoro-N-methyl-acetamide;
(RS,SR)-2-Benzenesulfonyl-2-(7-chloro-1,2,3,4-tetrahydro-cyclopenta[b]indol-2-yl)-2-fluoro-N-methyl-acetamide;
(RS,SR)-2-(6-Chloro-2,3,4,9-tetrahydro-1H-carbazol-2-yl)-2-fluoro-2-(3-fluoro-benzenesulfonyl)-N-methyl-acetamide;
(RS,SR)-2-(7-Chloro-1,2,3,4-tetrahydro-cyclopenta[b]indol-2-yl)-2-fluoro-2-(3-fluoro-benzenesulfonyl)-N-methyl-acetamide;
(RS,SR)-2-Benzenesulfonyl-2-(6-chloro-2,3,4,9-tetrahydro-1H-carbazol-2-yl)-2-fluoro-N,N-dimethyl-acetamide;
(RS,SR)-2-Benzenesulfonyl-2-(7-chloro-1,2,3,4-tetrahydro-cyclopenta[b]indol-2-yl)-2-fluoro-N,N-dimethyl-acetamide;
(RS,SR)-2-(6-Chloro-2,3,4,9-tetrahydro-1H-carbazol-2-yl)-2-fluoro-2-(3-fluoro-benzenesulfonyl)-N,N-dimethyl-acetamide;
(RS,SR)-2-(7-Chloro-1,2,3,4-tetrahydro-cyclopenta[b]indol-2-yl)-2-fluoro-2-(3-fluoro-benzenesulfonyl)-N,N-dimethyl-acetamide;
(RS,SR)-2-Benzenesulfonyl-N-benzyl-2-(6-chloro-2,3,4,9-tetrahydro-1H-carbazol-2-yl)-2-fluoro-N-methyl-acetamide;
(RS,SR)-2-Benzenesulfonyl-2-(6-chloro-2,3,4,9-tetrahydro-1H-carbazol-2-yl)-N-(4-cyano-benzyl)-2-fluoro-N-methyl-acetamide;
(RS,SR)-2-Benzenesulfonyl-N-(4-bromo-benzyl)-2-(6-chloro-2,3,4,9-tetrahydro-1H-carbazol-2-yl)-2-fluoro-N-methyl-acetamide;
(RS,SR)-2-Benzenesulfonyl-2-(6-chloro-2,3,4,9-tetrahydro-1H-carbazol-2-yl)-N-(3,5-difluoro-benzyl)-2-fluoro-N-methyl-acetamide;
(RS,SR)-4-({[2-Benzenesulfonyl-2-(6-chloro-2,3,4,9-tetrahydro-1H-carbazol-2-yl)-2-fluoro-acetyl]-methyl-amino}-methyl)-benzoic acid methyl ester;
(RS,SR)-3-({[2-Benzenesulfonyl-2-(6-chloro-2,3,4,9-tetrahydro-1H-carbazol-2-yl)-2-fluoro-acetyl]-methyl-amino}-methyl)-benzoic acid methyl ester;
(RS,SR)-2-Benzenesulfonyl-2-(6-chloro-2,3,4,9-tetrahydro-1H-carbazol-2-yl)-N-(2-cyano-benzyl)-2-fluoro-N-methyl-acetamide;
(RS,SR)-N-Allyl-2-benzenesulfonyl-2-(6-chloro-2,3,4,9-tetrahydro-1H-carbazol-2-yl)-2-fluoro-N-methyl-acetamide;
(RS,SR)-2-Benzenesulfonyl-2-(6-chloro-2,3,4,9-tetrahydro-1H-carbazol-2-yl)-N-(3-cyano-benzyl)-2-fluoro-N-methyl-acetamide;
(RS,SR)-3-({[2-Benzenesulfonyl-2-(6-chloro-2,3,4,9-tetrahydro-1H-carbazol-2-yl)-2-fluoro-acetyl]-methyl-amino}-methyl)-benzoic acid;
(RS,SR)-2-Benzenesulfonyl-2-(6-chloro-2,3,4,9-tetrahydro-1H-carbazol-2-yl)-2-fluoro-N-(3-hydroxymethyl-benzyl)-N-methyl-acetamide;
(RS,SR)-2-[Benzenesulfonyl-fluoro-(5-methyl-[1,3,4]oxadiazol-2-yl)-methyl]-7-chloro-1,2,3,4-tetrahydro-cyclopenta[b]indole;
(S)-2-[(R)-Benzenesulfonyl-fluoro-(5-methyl-[1,3,4]oxadiazol-2-yl)-methyl]-7-chloro-1,2,3,4-tetrahydro-cyclopenta[b]indole;
(R)-2-[(S)-Benzenesulfonyl-fluoro-(5-methyl-[1,3,4]oxadiazol-2-yl)-methyl]-7-chloro-1,2,3,4-tetrahydro-cyclopenta[b]indole;
(RS,SR)-2-[1-Benzenesulfonyl-1-(5-methyl-[1,3,4]oxadiazol-2-yl)-ethyl]-7-chloro-1,2,3,4-tetrahydro-cyclopenta[b]indole;
(RS,SR)-2-(Benzenesulfonyl-fluoro-[1,3,4]oxadiazol-2-yl-methyl)-7-chloro-1,2,3,4-tetrahydro-cyclopenta[b]indole;
(RS,SR)-2-[Benzenesulfonyl-(5-cyclopropyl-[1,3,4]oxadiazol-2-yl)-fluoro-methyl]-7-chloro-1,2,3,4-tetrahydro-cyclopenta[b]indole;
(RS,SR)-2-[Benzenesulfonyl-(5-cyclopropyl-[1,3,4]oxadiazol-2-yl)-fluoro-methyl]-6-chloro-2,3,4,9-tetrahydro-1H-carbazole;
(RS,SR)-{5-[Benzenesulfonyl-(7-chloro-1,2,3,4-tetrahydro-cyclopenta[b]indol-2-yl)-fluoro-methyl]-[1,3,4]oxadiazol-2-yl}-dimethyl-amine;
(RS,SR)-{5-[Benzenesulfonyl-(7-chloro-1,2,3,4-tetrahydro-cyclopenta[b]indol-2-yl)-fluoro-methyl]-[1,3,4]oxadiazol-2-yl}-dimethyl-amine;
(RS,SR)-2-[Benzenesulfonyl-fluoro-(3-methyl-[1,2,4]oxadiazol-5-yl)-methyl]-7-chloro-1,2,3,4-tetrahydro-cyclopenta[b]indole;

(RS,SR)-5-[Benzenesulfonyl-(7-chloro-1,2,3,4-tetrahydro-cyclopenta[b]indol-2-yl)-fluoro-methyl]-[1,2,4]oxadiazole-3-carboxylic acid methyl ester;
(RS,SR)-{5-[Benzenesulfonyl-(7-chloro-1,2,3,4-tetrahydro-cyclopenta[b]indol-2-yl)-fluoro-methyl]-[1,2,4]oxadiazol-3-yl}-methanol;
(RS,SR)-5-[Benzenesulfonyl-(7-chloro-1,2,3,4-tetrahydro-cyclopenta[b]indol-2-yl)-fluoro-methyl]-[1,2,4]oxadiazole-3-carboxylic acid;
(RS,SR)-5-[Benzenesulfonyl-(7-chloro-1,2,3,4-tetrahydro-cyclopenta[b]indol-2-yl)-fluoro-methyl]-[1,2,4]oxadiazole-3-carboxylic acid amide;
(RS,SR)-{5-[Benzenesulfonyl-(7-chloro-1,2,3,4-tetrahydro-cyclopenta[b]indol-2-yl)-fluoro-methyl]-[1,2,4]oxadiazol-3-yl}-dimethyl-amine;
(RS,SR)-7-Chloro-2-[(3-chloro-benzenesulfonyl)-fluoro-(3-methyl-[1,2,4]oxadiazol-5-yl)-methyl]-1,2,3,4-tetrahydro-cyclopenta[b]indole;
(RS,SR)-7-Chloro-2-[(3-chloro-benzenesulfonyl)-fluoro-(5-methyl-[1,3,4]oxadiazol-2-yl)-methyl]-1,2,3,4-tetrahydro-cyclopenta[b]indole;
(RS,SR)-2-{5-[Benzenesulfonyl-(7-chloro-1,2,3,4-tetrahydro-cyclopenta[b]indol-2-yl)-fluoro-methyl]-[1,2,4]oxadiazol-3-ylmethyl}-isoindole-1,3-dione;
(RS,SR)—C-{5-[Benzenesulfonyl-(7-chloro-1,2,3,4-tetrahydro-cyclopenta[b]indol-2-yl)-fluoro-methyl]-[1,2,4]oxadiazol-3-yl}-methylamine;
(RS,SR)-{5-[Benzenesulfonyl-(7-chloro-1,2,3,4-tetrahydro-cyclopenta[b]indol-2-yl)-fluoro-methyl]-[1,2,4]oxadiazol-3-ylmethyl}-dimethyl-amine;
(RS,SR)-{5-[Benzenesulfonyl-(7-chloro-1,2,3,4-tetrahydro-cyclopenta[b]indol-2-yl)-fluoro-methyl]-[1,2,4]oxadiazol-3-ylmethyl}-diethyl-amine;
(RS,SR)-{5-[Benzenesulfonyl-(7-chloro-1,2,3,4-tetrahydro-cyclopenta[b]indol-2-yl)-fluoro-methyl]-[1,2,4]oxadiazol-3-ylmethyl}-diethyl-amine;
(RS,SR)-2-(Benzenesulfonyl-benzooxazol-2-yl-fluoro-methyl)-7-chloro-1,2,3,4-tetrahydro-cyclopenta[b]indole;
(RS,SR)—N-{5-[Benzenesulfonyl-(7-chloro-1,2,3,4-tetrahydro-cyclopenta[b]indol-2-yl)-fluoro-methyl]-[1,2,4]oxadiazol-3-ylmethyl}-acetamide;
(RS,SR)—N-{5-[Benzenesulfonyl-(7-chloro-1,2,3,4-tetrahydro-cyclopenta[b]indol-2-yl)-fluoro-methyl]-[1,2,4]oxadiazol-3-ylmethyl}-benzamide;
(RS,SR)-2-Benzenesulfonyl-2-(6-bromo-2,3,4,9-tetrahydro-1H-carbazol-2-yl)-propionic acid methyl ester;
(RS,SR)-2-Benzenesulfonyl-2-(6-dimethylamino-2,3,4,9-tetrahydro-1H-carbazol-2-yl)-propionic acid methyl ester;
(6-Bromo-2,3,4,9-tetrahydro-1H-carbazol-2-yl)-methanesulfonyl-acetic acid methyl ester
(RS,SR)-2-(6-Bromo-2,3,4,9-tetrahydro-1H-carbazol-2-yl)-2-methanesulfonyl-propionic acid methyl ester;
(RS,SR)-2-(6-Dimethylamino-2,3,4,9-tetrahydro-1H-carbazol-2-yl)-2-methanesulfonyl-propionic acid methyl ester;
and pharmaceutically-acceptable salts and/or pharmaceutically-acceptable esters thereof.

Other preferred compounds of general formula (I) are those selected from the group consisting of
(3-bromo-benzenesulfonyl)-(7-chloro-1,2,3,4-tetrahydro-cyclopenta[b]indol-2-yl)-acetic acid methyl ester;
(RS, SR)-2-(3-bromo-benzenesulfonyl)-2-(7-chloro-1,2,3,4-tetrahydro-cyclopenta[b]indol-2-yl)-propionic acid methyl ester;
(RS, SR)-(7-chloro-1,2,3,4-tetrahydro-cyclopenta[b]indol-2-yl)-2-(3-pyrrolidin-1-yl-benzenesulfonyl)-propionic acid methyl ester;
(RS, SR) 2-[1-(3-bromo-benzenesulfonyl)-1-(5-methyl-[1,3,4]oxadiazol-2-yl)-ethyl]-7-chloro-1,2,3,4-tetrahydro-cyclopenta[b]indole;
(RS, SR)-2-[(3-bromo-benzenesulfonyl)-fluoro-(5-methyl-[1,3,4]oxadiazol-2-yl)-methyl]-7-chloro-1,2,3,4-tetrahydro-cyclopenta[b]indole;
(RS, SR) 2-[(5-benzyl-[1,3,4]oxadiazol-2-yl)-(3-bromo-benzenesulfonyl)-fluoro-methyl]-7-chloro-1,2,3,4-tetrahydro-cyclopenta[b]indole;
(RS, SR) {3-[(7-chloro-1,2,3,4-tetrahydro-cyclopenta[b]indol-2-yl)-fluoro-(5-methyl-[1,3,4]oxadiazol-2-yl)-methanesulfonyl]-phenyl}-dimethyl-amine;
(RS, SR)-7-chloro-2-[(3-ethynyl-benzenesulfonyl)-fluoro-(5-methyl-[1,3,4]oxadiazol-2-yl)-methyl]-1,2,3,4-tetrahydro-cyclopenta[b]indole;
(RS, SR)-2-[5-(4-benzyloxy-benzyl)-[1,3,4]oxadiazol-2-yl)-(3-bromo-benzenesulfonyl)-fluoro-methyl]-7-chloro-1,2,3,4-tetrahydro-cyclopenta[b]indole;
(RS, SR)-7-chloro-2-[(3-ethyl-benzenesulfonyl)-fluoro-(5-methyl-[1,3,4]oxadiazol-2-yl)-methyl]-1,2,3,4-tetrahydro-cyclopenta[b]indole;
(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzoic acid methyl ester;
(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzoic acid;
(RS, SR) (4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-phenyl)-methanol;
(RS, SR) 2-{benzenesulfonyl-fluoro-[5-(4-iodo-benzyl)-[1,3,4]oxadiazol-2-yl]-methyl}-7-chloro-1,2,3,4-tetrahydro-cyclopenta[b]indole;
(RS, SR) 4-{5-[(benzenesulfonyl)-(7-chloro-1,2,3,4-tetrahydro-cyclopenta[b]indol-2-yl)-fluoro-methyl]-[1,3,4]oxadiazol-2-yl}-benzoic acid;
(RS, SR) 4-{5-[benzenesulfonyl-(7-chloro-1,2,3,4-tetrahydro-cyclopenta[b]indol-2-yl)-fluoro-methyl]-[1,3,4]oxadiazol-2-ylmethyl}-benzoic acid;
(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzamide;
(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-N-methyl-benzamide;
(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-N,N-dimethyl-benzamide;
(RS,SR)-2-[-benzenesulfonyl-fluoro-(5-methyl-[1,3,4]oxadiazol-2-yl)-methyl]-7-bromo-1,2,3,4-tetrahydro-cyclopenta[b]indole;
(RS,SR)-2-[-benzenesulfonyl-fluoro-(5-methyl-[1,3,4]oxadiazol-2-yl)-methyl]-7-piperidin-1-yl-1,2,3,4-tetrahydro-cyclopenta[b]indole;
(RS,SR)—N-{2-[-benzenesulfonyl-fluoro-(5-methyl-[1,3,4]oxadiazol-2-yl)-methyl]-1,2,3,4-tetrahydro-cyclopenta[b]indol-7-yl}-N-methyl-amine;
2-[benzenesulfonyl-fluoro-(5-trifluoromethyl-[1,3,4]oxadiazol-2-yl)-methyl]-7-chloro-1,2,3,4-tetrahydro-cyclopenta[b]indole;
(RS,SR)-2-(1-benzenesulfonyl-2-methoxy-1-methyl-ethyl)-7-chloro-1,2,3,4-tetrahydro-cyclopenta[b]indole;
(RS,SR)-2-benzenesulfonyl-2-(-6-chloro-2,3,4,9-tetrahydro-1H-carbazol-2-yl)-2-fluoro-N-methyl-N-(3-methyl-but-2-enyl)-acetamide;

(RS,SR)-5-[-benzenesulfonyl-(-7-chloro-1,2,3,4-tetrahydro-cyclopenta[b]indol-2-yl)-fluoro-methyl]-[1,2,4]oxadiazole-3-carbonitrile;
(RS,SR)-{5-[-benzenesulfonyl-(-6-chloro-2,3,4,9-tetrahydro-1H-carbazol-2-yl)-fluoro-methyl]-[1,2,4]oxadiazol-3-yl}-dimethyl-amine;
(RS,SR)-4-[({5-[-benzenesulfonyl-(-7-chloro-1,2,3,4-tetrahydro-cyclopenta[b]indol-2-yl)-fluoro-methyl]-[1,2,4]oxadiazol-3-ylmethyl}-amino)-methyl]-benzoic acid methyl ester;
(RS,SR)-3-[({5-[-benzenesulfonyl-(-7-chloro-1,2,3,4-tetrahydro-cyclopenta[b]indol-2-yl)-fluoro-methyl]-[1,2,4]oxadiazol-3-ylmethyl}-amino)-methyl]-benzoic acid methyl ester;
(RS,SR)-{4-[({5-[-benzenesulfonyl-(-7-chloro-1,2,3,4-tetrahydro-cyclopenta[b]indol-2-yl)-fluoro-methyl]-[1,2,4]oxadiazol-3-ylmethyl}-amino)-methyl]-phenyl}-methanol;
(RS,SR)-2-(benzenesulfonyl-pyridin-2-yl-methyl)-7-chloro-1,2,3,4-tetrahydro-cyclopenta[b]indole;
(RS,SR)—N-{5-[(S)-benzenesulfonyl-((R)-7-chloro-1,2,3,4-tetrahydro-cyclopenta[b]indol-2-yl)-fluoro-methyl]-[1,2,4]oxadiazol-3-ylmethyl}-2,2,2-trifluoro-acetamide
2-[benzenesulfonyl-fluoro-(3-phenyl-[1,2,4]oxadiazol-5-yl)-methyl]-7-chloro-1,2,3,4-tetrahydro-cyclopenta[b]indole;
(RS,SR)-2-[-benzenesulfonyl-(-7-chloro-1,2,3,4-tetrahydro-cyclopenta[b]indol-2-yl)-fluoro-methyl]-oxazole-4-carboxylic acid methyl ester;
2-(benzenesulfonyl-benzothiazol-2-yl-fluoro-methyl)-7-chloro-1,2,3,4-tetrahydro-cyclopenta[b]indole;
(RS,SR)-2-[-benzenesulfonyl-(4,5-dimethyl-oxazol-2-yl)-methyl]-7-chloro-1,2,3,4-tetrahydro-cyclopenta[b]indole;
and pharmaceutically acceptable salts and/or pharmaceutically acceptable esters thereof.

Particularly preferred compounds of the general formula (I) are those selected from the group consisting of
(RS,SR)-2-Benzenesulfonyl-2-(6-chloro-2,3,4,9-tetrahydro-1H-carbazol-2-yl)-propionic acid methyl ester;
(RS,SR)-Benzenesulfonyl-(6-chloro-2,3,4,9-tetrahydro-1H-carbazol-2-yl)-fluoro-acetic acid methyl ester;
(RS,SR)-2-Benzenesulfonyl-2-(7-chloro-1,2,3,4-tetrahydro-cyclopenta[b]indol-2-yl)-propionic acid methyl ester;
(RS,SR)-Benzenesulfonyl-(7-chloro-1,2,3,4-tetrahydro-cyclopenta[b]indol-2-yl)-fluoro-acetic acid methyl ester;
(RS,SR)-Benzenesulfonyl-(7-bromo-8-fluoro-1,2,3,4-tetrahydro-cyclopenta[b]indol-2-yl)-fluoro-acetic acid methyl ester;
(RS,SR)-(3-Chloro-benzenesulfonyl)-(7-chloro-1,2,3,4-tetrahydro-cyclopenta[b]indol-2-yl)-fluoro-acetic acid methyl ester;
(RS,SR)-(7-Chloro-1,2,3,4-tetrahydro-cyclopenta[b]indol-2-yl)-fluoro-(3-fluoro-benzenesulfonyl)-acetic acid methyl ester;
(RS,SR)-(7-Chloro-1,2,3,4-tetrahydro-cyclopenta[b]indol-2-yl)-(3,4-difluoro-benzenesulfonyl)-fluoro-acetic acid methyl ester;
(RS,SR)-2-(6-Chloro-2,3,4,9-tetrahydro-1H-carbazol-2-yl)-2-fluoro-2-(3-fluoro-benzenesulfonyl)-N,N-dimethyl-acetamide;
(RS,SR)-2-[Benzenesulfonyl-fluoro-(5-methyl-[1,3,4]oxadiazol-2-yl)-methyl]-7-chloro-1,2,3,4-tetrahydro-cyclopenta[b]indole;
(S)-2-[(R)-Benzenesulfonyl-fluoro-(5-methyl-[1,3,4]oxadiazol-2-yl)-methyl]-7-chloro-1,2,3,4-tetrahydro-cyclopenta[b]indole;
(R)-2-[(S)-Benzenesulfonyl-fluoro-(5-methyl-[1,3,4]oxadiazol-2-yl)-methyl]-7-chloro-1,2,3,4-tetrahydro-cyclopenta[b]indole;
(RS,SR)-2-[Benzenesulfonyl-(5-cyclopropyl-[1,3,4]oxadiazol-2-yl)-fluoro-methyl]-7-chloro-1,2,3,4-tetrahydro-cyclopenta[b]indole;
(RS,SR)-{5-[Benzenesulfonyl-(7-chloro-1,2,3,4-tetrahydro-cyclopenta[b]indol-2-yl)-fluoro-methyl]-[1,3,4]oxadiazol-2-yl}-dimethyl-amine;
(RS,SR)-2-[Benzenesulfonyl-fluoro-(3-methyl-[1,2,4]oxadiazol-5-yl)-methyl]-7-chloro-1,2,3,4-tetrahydro-cyclopenta[b]indole;
(RS,SR)-{5-[Benzenesulfonyl-(7-chloro-1,2,3,4-tetrahydro-cyclopenta[b]indol-2-yl)-fluoro-methyl]-[1,2,4]oxadiazol-3-yl}-dimethyl-amine;
and pharmaceutically-acceptable salts and/or pharmaceutically-acceptable esters thereof.

Other particularly preferred compounds of the general formula (I) are those selected from the group consisting of
(RS, SR)-2-[(3-bromo-benzenesulfonyl)-fluoro-(5-methyl-[1,3,4]oxadiazol-2-yl)-methyl]-7-chloro-1,2,3,4-tetrahydro-cyclopenta[b]indole;
(RS, SR) {3-[(7-chloro-1,2,3,4-tetrahydro-cyclopenta[b]indol-2-yl)-fluoro-(5-methyl-[1,3,4]oxadiazol-2-yl)-methanesulfonyl]-phenyl}-dimethyl-amine;
(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzoic acid methyl ester;
(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzoic acid;
(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzamide;
(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-N,N-dimethyl-benzamide;
(RS,SR)-2-[-benzenesulfonyl-(-7-chloro-1,2,3,4-tetrahydro-cyclopenta[b]indol-2-yl)-fluoro-methyl]-oxazole-4-carboxylic acid methyl ester;
2-(benzenesulfonyl-benzothiazol-2-yl-fluoro-methyl)-7-chloro-1,2,3,4-tetrahydro-cyclopenta[b]indole;
and pharmaceutically-acceptable salts and/or pharmaceutically-acceptable esters thereof.

The compounds of formula (I) can contain several asymmetric centres and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluent).

The compounds of formula (I), the pharmaceutically acceptable salts of the compounds of formula (I) and the pharmaceutically acceptable esters of the compounds of formula (I) individually constitute preferred embodiments of the present invention. Particularly preferred are compounds of formula (I).

It will be appreciated that the compounds of the general formula (I) in this invention may be derivatized at functional groups to provide derivatives which are capable of conversion back to the parent compound in vivo.

The present invention also relates to a process for the manufacture of compounds of formula (I) as described above, the process comprising reacting a compound of formula (II)

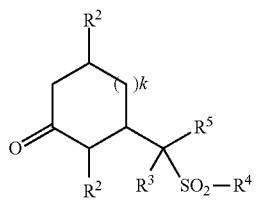

II wherein $R^2$, $R^3$, $R^4$, $R^5$, and k have the significances given above, with a compound of formula III

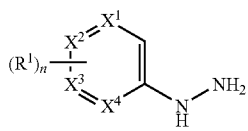

III wherein $R^1$, n, $X^1$, $X^2$, $X^3$, and $X^4$ have the significances given above, and optionally converting the compound of formula I to a pharmaceutically acceptable salt and/or a pharmaceutically acceptable ester.

Reactions of a compound of formula (II) with a hydrazine of formula (III) can be carried out by procedures known in the art and as described in Scheme 1 below. For example, when reacting a substituted aryl hydrazine with a compound of formula (II), pure acetic acid between RT and 40° C. when k is 1, and between RT and 75° C. when k is 0, can be employed in the modified Fischer-Indole synthesis. Alternatively, when reacting a heteroaryl hydrazine, reaction can take place at 120° C. in a sealed tube.

In another embodiment, when compounds of formula (I) contain an $R^5$ group that is a tertiary amide, compounds of formula I can be carried out by procedures known in the art and as described in Scheme 5 and Scheme 6 below.

The invention further relates to compounds of formula (I) as defined above, when manufactured according to a process as defined above.

As described above, the compounds of formula (I) of the present invention can be used as medicaments for the treatment and/or prevention of diseases which are modulated by LXRα and/or LXRβ agonists. Examples of such diseases are increased lipid and cholesterol levels, particularly low HDL-cholesterol, high LDL-cholesterol, atherosclerotic diseases, diabetes, particularly non-insulin dependent diabetes mellitus, metabolic syndrome, dyslipidemia, Alzheimer's disease, sepsis, inflammatory diseases such as colitis, pancreatitis, cholestasis/fibrosis of the liver, and diseases that have an inflammatory component such as Alzheimer's disease or impaired/improvable cognitive function. The use of compounds of formula (I) for in the treatment of atherosclerosis, low HDL cholesterol levels, non-insulin dependent diabetes mellitus, and metabolic syndrome is preferred. The compounds of formula (I) can further be used for treatment and prophylaxis of age-related macular degeneration.

The invention therefore also relates to pharmaceutical compositions comprising a compound of formula (I) as defined above and a pharmaceutically acceptable carrier and/or adjuvant.

Further, the invention relates to compounds as defined above for use as therapeutic active substances, particularly as therapeutic active substances for the treatment and/or prophylaxis of diseases which are modulated by LXRα and/or LXRβ agonists. Preferred examples of such diseases are atherosclerosis, increased lipid and cholesterol levels, particularly low HDL-cholesterol, high LDL-cholesterol, non-insulin dependent diabetes mellitus, metabolic syndrome, dyslipidemia, Alzheimer's disease, sepsis, and inflammatory diseases.

In another embodiment, the invention relates to a method for the treatment and/or prophylaxis of diseases which are modulated by LXRα and/or LXRβ agonists, such as e.g. atherosclerosis, increased lipid and cholesterol levels, particularly low HDL-cholesterol, high LDL-cholesterol, non-insulin dependent diabetes mellitus, metabolic syndrome, dyslipidemia, Alzheimer's disease, sepsis, and/or inflammatory diseases, the method comprising administering a compound of formula (I) to a human or animal.

Further preferred is a method for the treatment and/or prophylaxis of diseases which are modulated by LXRα and/or LXRβ agonists, the method comprising administering a compound as defined above to a human being or animal in particular, wherein said disease is selected from the group consisting of increased lipid and cholesterol levels, particularly low HDL-cholesterol and/or high LDL-cholesterol, atherosclerotic diseases, diabetes, particularly non-insulin dependent diabetes mellitus, metabolic syndrome, dyslipidemia, sepsis, inflammatory diseases including colitis, pancreatitis, cholestasis/fibrosis of the liver, and diseases that have an inflammatory component such as Alzheimer's disease or impaired/improvable cognitive function.

The invention further relates to the use of compounds as defined above for the treatment and/or prophylaxis of diseases which are modulated by LXRα and/or LXRβ agonists such as atherosclerosis, increased lipid and cholesterol levels, particularly low HDL-cholesterol, high LDL-cholesterol, non-insulin dependent diabetes mellitus, metabolic syndrome, dyslipidemia, Alzheimer's disease, sepsis, and/or inflammatory diseases.

In addition, the invention relates to the use of compounds as defined above for the preparation of medicaments for the treatment and/or prophylaxis of diseases which are modulated by LXRα and/or LXRβ agonists such as atherosclerosis, increased lipid and cholesterol levels, particularly low HDL-cholesterol, high LDL-cholesterol, non-insulin dependent diabetes mellitus, metabolic syndrome, dyslipidemia, Alzheimer's disease, sepsis, and/or inflammatory diseases.

The compounds of formula (I) can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art. In case it is not otherwise indicated all substituents mentioned in Schemes 1, 2a, 2b, 3, 4, 5, and 6 are defined as before. Substituent $R^2$ means hydrogen and is therefore not always mentioned.

Compounds of formula I can be prepared by the following Reaction Scheme 1:

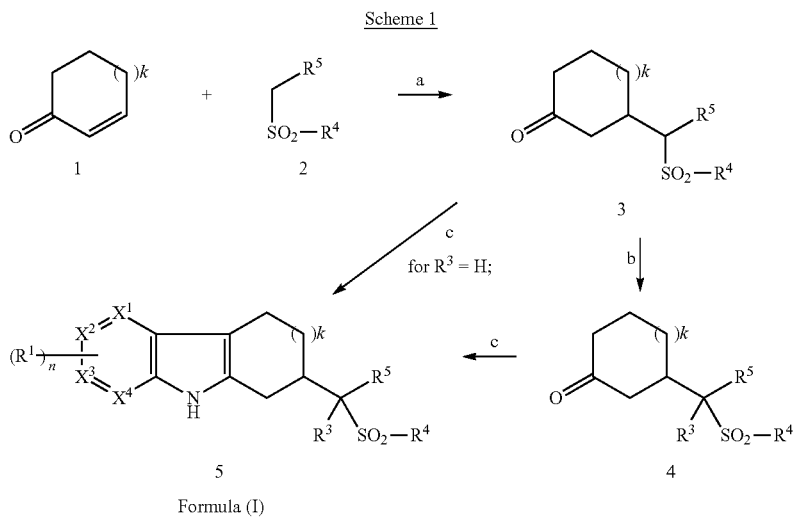

Formula (I)

wherein $R^1$, $R^3$, $R^4$, $R^5$, X, k, and n have the signifigances given above. $R^2$ means hydrogen and is therefore not mentioned in formula (I).

Michael addition of a sulfonyl derivative 2 to a cyclic 2-enone 1, at RT in MeOH containing 10-20% of NaOMe or in THF or acetonitrile in the presence of bases such as $K_2CO_3$ or $Cs_2CO_3$, leads to the corresponding 3-substituted cyclic ketone 3 (step a). The alkylation of 3 may be carried out with NaH in DMF at 0° C. followed by the addition of the electrophile $R^3$—X (MeI, N-fluorobenzenesulfonimide for example) to give 4 as a racemic mixture of diastereomers (step b). The two diastereomers (RS,SR) and (RR,SS) may be separated by column chromatography on silica gel at this stage. A modified Fischer-Indole synthesis is used to prepare compounds of formula (I). Reaction of the ketone 3 or 4 with the aryl hydrazine (substituted aryl hydrazine) in pure acetic acid between RT and 40° C. for k=1, and between RT and 75° C. for k=0, and at around 120° C. in a sealed tube for heteroaryl hydrazines leads to compounds of formula (I) (step c).

Functional groups present on $R^1$ and $R^4$ can be be transformed into other functional groups at this stage of the synthesis using standard procedures commonly known to those of the art. Typical examples are the replacement of an iodo- or bromo-substituent by an amino group using Buchwald coupling conditions or replacement of a iodo- or bromo-substituent by a 1-alkynylo-group using Sonogashira coupling conditions. These alkynyl moieties can be further modified to alkyl residues by hydrogenation. Functional groups present on $R^5$ may be converted to other residues by formations listed for $R^1$ and $R^4$ or by conversion of an alkoxycarbonyl group into a carboxyl group by hydrolysis in presence of LiOH or NaOH, of a carboxyl group into a aminocarbonyl group using a primary or secondary amine and a peptide coupling reagent such as e.g. EDCI, of an alkoxycarbonyl group into a hydroxyalkyl residue by reduction with $LiAlH_4$, or of an hydroxyalkyl residue into an ether moiety by alkylation. If required the nitrogen of the tetrahydrocarbazoles, 1,2,3,3a,4,8b-tetrahydro-cyclopenta[b]indoles and related heterocycles may be BOC- or Z-protected prior to these transformations.

For the preparation of the sulfonyl derivatives 2 needed for the Michael-Addition in Scheme 1 the following 2 different synthetic routes may be used. Scheme 2a describes the synthesis of the sulfonyl derivatives starting with the alkylation of thiols 1 with an electrophile of formula 2 in the presence of a base to give the sulfides 3. The preferred bases are either $K_2CO_3$ using acetone as solvent or NaH in DMF (step a). The sulfides 3 are subsequently oxidized to the corresponding sulfonyl derivatives 4 with either oxone (potassium peroxymonosulfate) in MeOH at RT over night, or with mCPBA in $CHCl_3$ or $CH_2Cl_2$ at RT (step b).

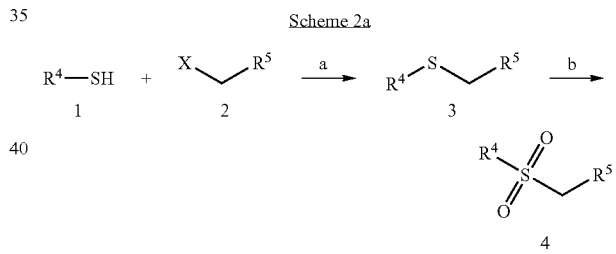

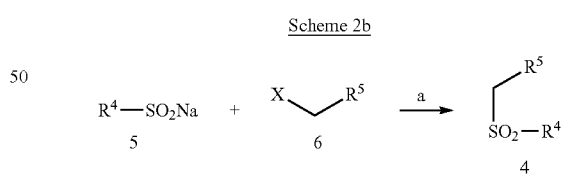

An alternative route to the sulfon derivatives is depicted in scheme 2b. The sulfinic acid sodium salt 5, either commercially available or prepared from the corresponding sulfinic acid and a base, may be treated with the electrophile 6 to afford sulfon derivatives 4 (e.g. Y. Nagao, S. Yamada, E. Fujita, *Tet. Lett.* 1983, 2291-2294).

If it is desired to produce compounds of formula I wherein the sulfonyl derivatives bear a $R^5$ substituted [1,3,4]-oxadiazole moiety, the process depicted in Scheme 3 may be used. Addition of hydrazine hydrate to the ester 1 (prepared as described in Scheme 2a, for $R^5$=X—$CH_2$—$(CH_2)_m CO_2Me$) in MeOH at RT leads to the hydrazide 2 (step a). The hydrazide 2 is acylated with acetic anhydride in acetic acid to the intermediate of formula 3 (step b), which is cyclised with POCl₃ in acetonitrile to 4 (step c). Alternatively, the oxadiazole 4 may be prepared by treatment of the hydrazide 2 in POCl₃ in the presence of a carboxylic acid $R_{53}$—$(CH_2)_v$—COOH at reflux (route d). An additional mode of preparation of derivatives 4 is the treatment of the hydrazide 2 in trimethyl orthoformate with POCl₃.

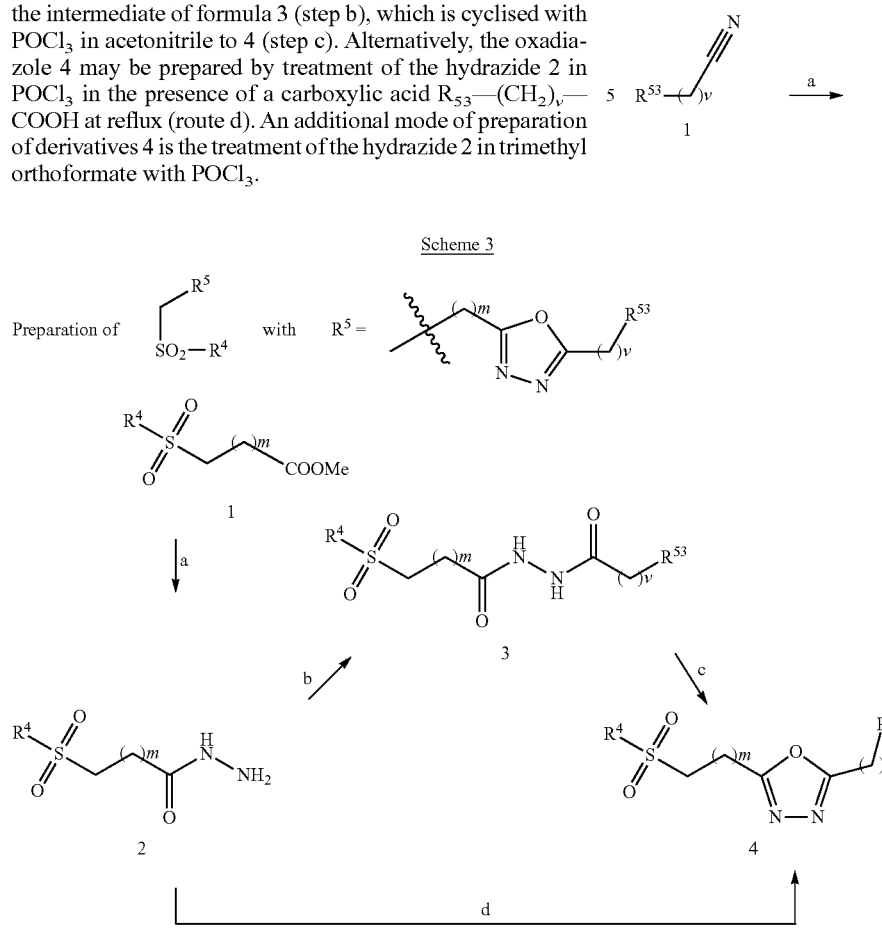

Scheme 3

The preparation of sulfonyl derivatives with a substituted [1,2,4]-oxadiazole moiety is depicted in Scheme 4 below (compounds 5). Treatment of nitrile derivatives 1 with hydroxylamine hydrochloride and NaOMe in MeOH at RT leads to amino-hydroxyimino derivatives 2 (step a), which are converted into the oxadiazoles 4 by reaction with compound 3 using one of the following methods (step b):

Method A) After treatment of 2 with NaH in THF at RT, the ester 3 is added and the reaction mixture is then stirred at 60° C. for 2 hours.

Method B) Alternatively, 2 is treated at RT in THF with 3 (for X=Cl) for 2 hours. After evaporation of the solvent, the mixture is refluxed in dioxane over night in the presence of molecular sieves.

The resulting sulfides 4 are oxidized to the sulfonyl derivatives of formula 5 with mCPBA at RT in CHCl₃ (step c).

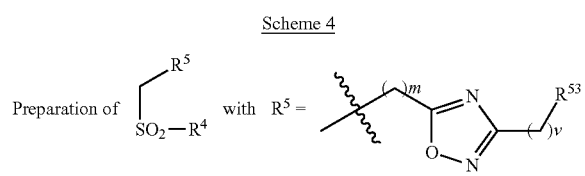

Scheme 4

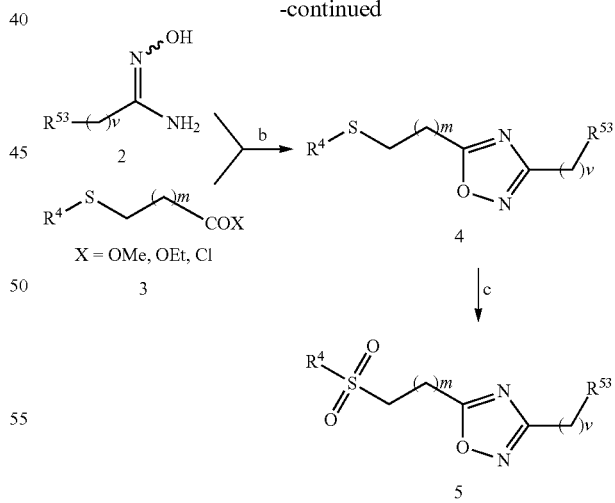

The preparation of compound of general formula (I) with $R^5$ being a tertiary amide is shown e.g. in Scheme 5. Esters of type 1 (prepared using the procedure described above) are converted to secondary amides 2 by reaction with a primary amine and KCN in a sealed tube (step a). Boc-protection using (Boc)₂O, DMAP, Et₃N, CH₂Cl₂ at RT leads to compounds 3 (step b), which are alkylated via deprotonation with NaH in THF and subsequent treatment with a range of electrophiles. TFA mediated deprotection in CH$_2$Cl$_2$ leads to the final compounds 4 (step c).

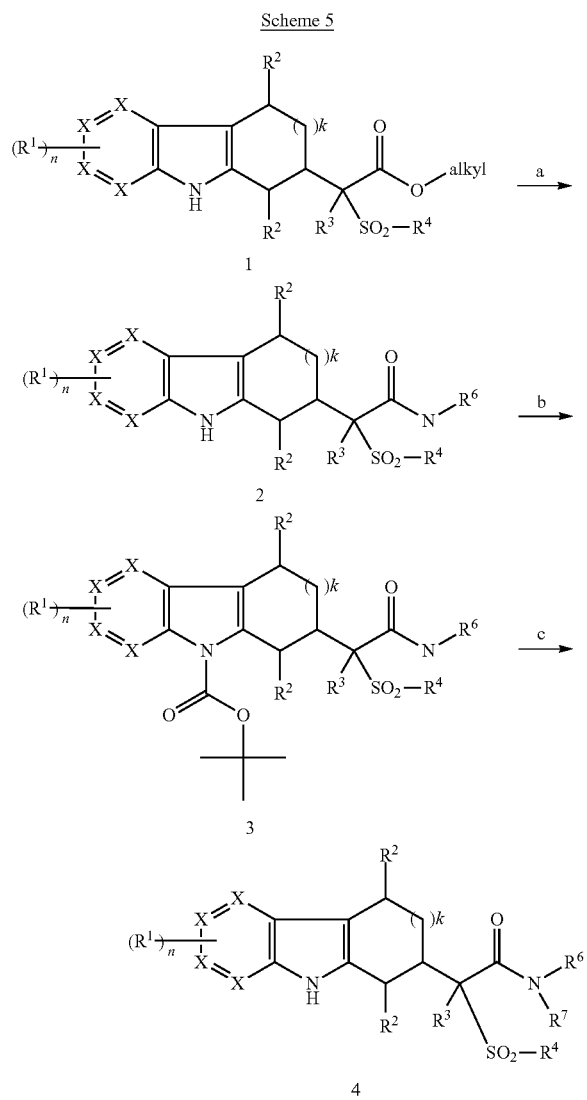

Scheme 5 alkyl is prefereably methyl or ethyl

Functional groups present on R$^4$ or R$^{53}$ can—if desired or required—be transformed into other functional groups at a suitable stage of the synthesis using standard procedures commonly known to those of the art. Typical examples are the transformation of an alkoxycarbonyl group into a carboxyl group by hydrolysis in presence of LiOH, of a carboxyl group into a aminocarbonyl group using a primary or secondary amine and a peptide coupling reagent such as e.g. EDCI, replacement of a iodo- or bromo-substituent by an amino group using Buchwald coupling conditions or replacement of a iodo- or bromo-substituent by a 1-alkynylo-group using Sonogashira coupling conditions. If required the nitrogen of the tetrahydrocarbazoles, 1,2,3,3a,4,8b-tetrahydro-cyclopenta[b]indoles and related heterocycles may be BOC- or Z-protected prior to these transformations.

The following tests were carried out in order to determine the activity of the compounds of formula (I) and their salts.

General Information

Background information on the performed assays can be found in: Nichols J S et al. "Development of a scintillation proximity assay for peroxisome proliferator-activated receptor gamma ligand binding domain", Anal Biochem. 1998, 257: 112-119.

Mammalian expression vectors were constructed to express full-length human LXRα and LXRβ. Bacterial expression vectors were constructed to produce glutathione-s-transferase (GST) fused to the ligand binding domains (LBD) of human LXRα (aa 164 to 447) and human LXRβ (aa 155 to 460). To accomplish this, the portions of the sequences encoding the LBDs were amplified from full-length clones by PCR and then subcloned into the plasmid vectors. Final clones were verified by DNA sequence analysis (Willy et al., Genes Dev. 1995, 9:1033-45; Song et al., Proc Natl Acad Sci USA. 1994, 91:10809-13).

Induction, expression, and purification of GST-LBD fusion proteins were performed in *E. coli* strain BL21(pLysS) cells by standard methods (Ref: Current Protocols in Molecular Biology, Wiley Press, edited by Ausubel et al).

Radioligand Binding Assay

LXRα and LXRβ receptor binding were assayed in buffer consisting of 50 mM HEPES, pH 7.4, 10 mM NaCl, 5 mM MgCl$_2$. For each 96-well reaction, 500 ng of GST-LXRα-LBD or 700 ng of GST-LXRβ-LBD fusion proteins were bound to 80 μg or 40 μg SPA beads (Pharmacia Amersham) respectively, in a final volume of 50 μl by shaking. The resulting slurry was incubated for 1 h at RT and centrifuged for 2 min at 1300×g. The supernatant containing unbound protein was removed, and the semi-dry pellet containing the receptor-coated beads was re-suspended in 50 μl of buffer. Radioligand (eg. 100,000 dpm of (N-(2,2,2-trifluoroethyl)-N-[4-(2,2,2-trifluoro-1-hydroxy-1-trifluoromethylethyl)-phenyl]-benzenesulfonamide)) was added, and the reaction incubated at RT for 1 h in the presence of test compounds, and then scintillation proximity counting was performed. All binding assays were performed in 96-well plates and the amount of bound ligand was measured on a Packard TopCount using Opti-Plates (Packard). Dose response curves were performed within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95% O2:5% CO$_2$ atmosphere. Cells were seeded in 6-well plates at a density of 10$^5$ Cells/well and then batch-transfected with either the full-length-LXRα or full-length-LXRβ expression plasmids plus a reporter plasmid expressing luceriferase under the control of LXR response elements. Transfection was accomplished with the Fugene 6 reagent (Roche Molecular Biochemicals) according to the suggested protocol. Six hours following transfection, the cells were harvested by trypsinization and seeded in 96-well plates at a density of 10$^4$ cells/well. After 24 hours to allow attachment of cells, the medium was removed and replaced with 100 μl of phenol red-free medium containing the test substances or control ligands (final DMSO concentration: 0.1%). Following incubation of the cells for 24 hours with substances, 50 μl of the supernatant was discarded and then 50 μl of Luciferase Constant—Light Reagent (Roche Molecular Biochemicals) was added to lyse the cells and initiate the luciferase reaction. Luminescence, as a measure of luciferase activity, was detected in a Packard TopCount. Transcriptional activation in the presence of a test substance was expressed as fold-change in luminescence compared to that of cells incubated in the absence of the substance. EC$_{50}$ values were calculated using the XLfit program (ID Business Solutions Ltd. UK).

The compounds according to formula (I) have an activity in at least one of the above assays (EC50 or IC50) of 0.1 nM to 100 μM, preferably 0.1 nM to 1 μM. (μM means micromolar).

For example, the following compounds exhibited the following IC50 values in the binding assay:

|  | LXRalpha Binding IC50 [μmol/l] | LXRbeta Binding IC50 [μmol/l] |
| --- | --- | --- |
| (RS,SR)-2-Benzenesulfonyl-2-(6-chloro-2,3,4,9-tetrahydro-1H-carbazol-2-yl)-propionic acid methyl ester. | 1.600 | 0.270 |
| (RS,SR)-Benzenesulfonyl-(7-chloro-1,2,3,4-tetrahydro-cyclopenta[b]indol-2-yl)-fluoro-acetic acid methyl ester. | 0.090 | 0.050 |
| (RS,SR) {3-[(7-chloro-1,2,3,4-tetrahydro-cyclopenta[b]indol-2-yl)-fluoro-(5-methyl-[1,3,4]oxadiazol-2-yl)-methanesulfonyl]-phenyl}-dimethyl-amine. | 0.043 | 0.006 |

The compounds of formula I and/or pharmaceutically-acceptable salts and/or pharmaceutically-acceptable esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

In a preferred embodiment, pharmaceutical preparations contain about 1-500 mg, more preferably 1-100 mg, of a compound of formula I.

The present invention will be better understood from the following examples, which are for purposes of illustration and are not intended to limit the invention defined in the claims, which follow thereafter.

EXAMPLES

Abbreviations:
BOC=t-butyloxycarbonyl, $CH_2Cl_2$=dichloromethane, $CCl_4$=tetrachloromethane, mCPBA=m-chloroperbenzoic acid, CuI=copper iodide, DMAP=4-dimethylaminopyridine, DMF=dimethylformamide, EDCI=1-(3-dimethylaminopropyl)-3-ethylcarbodiimide hydrochloride, EtOAc=ethylacetate, EtOH=ethanol, $Et_2O$=diethylether, $Et_3N$=triethylamine, eq=equivalent, Huenig's base=$iPr_2NEt$=N-ethyl diisopropylamine, $LiAlH_4$=lithium aluminum hydride, MeOH=methanol, NaH=sodium hydride, NaOtBu=sodium tert. butylate, NBS=N-bromosuccinimide, RT=room temperature, THF=tetrahydrofuran, $NaHCO_3$=sodium bicarbonate, $NH_4Cl$=ammonium chloride, TFA=trifluoroacetic acid, NaOH=sodium hydroxide.

General Remarks
All reactions were performed under argon.

Example 1 benzenesulfonyl-(6-chloro-2,3,4,9-tetrahydro-1H-carbazol-2-yl)-acetic acid methyl ester To a stirred solution of 9 g (0.042 mol) of methyl phenylsulfonylacetate in 90 mL of MeOH at 0° C., 1.56 mL (0.008 mol, 0.2 eq) of a solution of sodium methoxide (5.4 M in MeOH) were added. After 15 min, 4.04 g (0.02 mol) of 2-cyclohexen-1-one were added. The reaction mixture was allowed to reach RT within 4 hours, diluted with saturated aqueous $NH_4Cl$ and extracted with EtOAc. The combined organic phases were dried over $Na_2SO_4$, filtered and evaporated. Column chromatography on silica gel with heptane/EtOAc 1:1 yielded 11.50 g (88%) of benzenesulfonyl-(3-oxo-cyclohexyl)-acetic acid methyl ester as a racemic mixture of diastereomers, light yellow oil, MS: 311 ($MH^+$).

To 5 g (0.016 mol) of benzenesulfonyl-(3-oxo-cyclohexyl)-acetic acid methyl ester in glacial acetic acid (30 mL), 3.17 g (0.018 mol, 1.1 eq) of 4-chlorophenylhydrazine hydrochloride were added and the reaction mixture was stirred at 40° C. for 2 hours. An aqueous solution of $NaHCO_3$ was added until pH=7 was reached, and the mixture was extracted with EtOAc. The combined organic phases were dried over $Na_2SO_4$, filtered and evaporated. A column chromatography on silica gel followed by a trituration from $Et_2O$ yielded 4.3 g (64%) of benzenesulfonyl-(6-chloro-2,3,4,9-tetrahydro-1H-carbazol-2-yl)-acetic acid methyl ester as a racemic mixture of diastereomers, light brown crystals, MS: 418 ($MH^+$).

29

Example 2 benzenesulfonyl-(6-fluoro-2,3,4,9-tetrahydro-1H-carbazol-2-yl)-acetic acid methyl ester In analogy to example 1.2, from benzenesulfonyl-(3-oxo-cyclohexyl)-acetic acid methyl ester and (4-fluoro-phenyl)-hydrazine hydrochloride was prepared benzenesulfonyl-(6-fluoro-2,3,4,9-tetrahydro-1H-carbazol-2-yl)-acetic acid methyl ester as a racemic mixture of diastereomers, light yellow solid, MS: 402 (MH$^+$).

Example 3

(RS,SR)-2-benzenesulfonyl-2-(6-chloro-2,3,4,9-tetrahydro-1H-carbazol-2-yl)-propionic acid methyl ester 3.1
To a stirred solution of 2 g (6.44 mmol) of benzenesulfonyl-(3-oxo-cyclohexyl)-acetic acid methyl ester in 40 mL of DMF at 0° C., 283 mg (7.09 mmol, 1.1 eq) of NaH (60%) were added. The reaction mixture was stirred at this temperature for one hour, and 1.37 g (9.66 mmol, 1.5 eq) of methyliodide were added. After 2 hours at RT, the reaction mixture was poured into water and extracted with EtOAc. The combined organic phases were dried over Na$_2$SO$_4$, filtered and evaporated. The resulting two diastereomers were separated by column chromatography on silica gel with heptane/EtOAc 2:1, yielding 0.79 g (38%) of (RS,SR)-2-benzenesulfonyl-2-(3-oxo-cyclohexyl)-propionic acid methyl ester as a white solid, MS: 325 (MH$^+$) and 0.71 g (34%) of (RR,SS)-2-benzenesulfonyl-2-(3-oxo-cyclohexyl)-propionic acid methyl ester as a white solid, MS: 325 (MH$^+$).

3.2
To 0.14 g (0.43 mmol) (RS,SR)-2-benzenesulfonyl-2-(3-oxo-cyclohexyl)-propionic acid methyl ester in glacial acetic acid (3 mL), 88 mg (0.47 mmol, 1.1 eq) of (4-chloro-phenyl)-hydrazine hydrochloride were added and the reaction mixture was stirred at 40° C. over night. An aqueous solution of NaHCO$_3$ was added until pH=7 was reached, and the mixture was extracted with EtOAc. The combined organic phases were dried over Na$_2$SO$_4$, filtered and evaporated. A column chromatography on silica gel with heptane/EtOAc 2:1 followed by a trituration with Et$_2$O yielded 187 mg (65%) of (RS,SR)-2-benzenesulfonyl-2-(6-chloro-2,3,4,9-tetrahydro-1H-carbazol-2-yl)-propionic acid methyl ester as a white solid, MS: 432 (MH$^+$).

The enantiomers were separated by preparative chiral HPLC. Column: chiralpak AD, solvent: 20% isopropanol/heptane

Example 4

(RS,SR)-2-benzenesulfonyl-2-(6-fluoro-2,3,4,9-tetrahydro-1H-carbazol-2-yl)-propionic acid methyl ester In analogy to example 3.2, from (RS,SR)-2-benzenesulfonyl-2-(3-oxo-cyclohexyl)-propionic acid methyl ester and (4-fluoro-phenyl)-hydrazine hydrochloride was prepared (RS,SR)-2-benzenesulfonyl-2-(6-fluoro-2,3,4,9-tetrahydro-1H-carbazol-2-yl)-propionic acid methyl ester as a white solid, MS: 416 (MH$^+$).

30

Example 5

(RS,SR)-2-benzenesulfonyl-2-(6-methyl-2,3,4,9-tetrahydro-1H-carbazol-2-yl)-propionic acid methyl ester In analogy to example 3.2, from (RS,SR)-2-benzenesulfonyl-2-(3-oxo-cyclohexyl)-propionic acid methyl ester and (4-methyl-phenyl)-hydrazine hydrochloride was prepared (RS,SR)-2-benzenesulfonyl-2-(6-methyl-2,3,4,9-tetrahydro-1H-carbazol-2-yl)-propionic acid methyl ester as a white solid, MS: 412 (MH$^+$).

Example 6

(RS,SR)-2-benzenesulfonyl-2-(6-nitro-2,3,4,9-tetrahydro-1H-carbazol-2-yl)-propionic acid methyl ester Analogously to example 3.2, from (RS,SR)-2-benzenesulfonyl-2-(3-oxo-cyclohexyl)-propionic acid methyl ester and (4-nitro-phenyl)-hydrazine hydrochloride was prepared (RS,SR)-2-benzenesulfonyl-2-(6-nitro-2,3,4,9-tetrahydro-1H-carbazol-2-yl)-propionic acid methyl ester as a light yellow solid, MS: 460 (MNH$_4^+$).

Example 7

(RS,SR)-2-benzenesulfonyl-2-(6-cyano-2,3,4,9-tetrahydro-1H-carbazol-2-yl)-propionic acid methyl ester Analogously to example 3.2, from (RS,SR)-2-benzenesulfonyl-2-(3-oxo-cyclohexyl)-propionic acid methyl ester and (4-cyano-phenyl)-hydrazine hydrochloride was prepared (RS,SR)-2-benzenesulfonyl-2-(6-cyano-2,3,4,9-tetrahydro-1H-carbazol-2-yl)-propionic acid methyl ester as a light yellow solid, MS: 423 (MH$^+$).

Example 8

(RS,SR)-2-benzenesulfonyl-2-(2-chloro-6,7,8,9-tetrahydro-5H-pyrido[3,2-b]indol-7-yl)-propionic acid methyl ester 8.1
To 0.5 g (3.9 mmol) of 6-chloro-pyridin-3-ylamine in 6 mL of 12M HCl at −20° C. were added a solution of 0.36 g (5.2 mmol, 1.3 eq) of sodium nitrite dissolved in 2 mL of H$_2$0. The reaction mixture was stirred for 15 min, and 4.4 g (19.5 mmol, 5 eq) of tin chloride dihydrate dissolved in 2 mL of 12M HCl were added. The reaction mixture was allowed to reach 0° C. within 40 min, and the white precipitate was recovered by filtration and washed with Et$_2$O to yield 0.35 g (62%) of (6-chloro-pyridin-3-yl)-hydrazine hydrochloride as a white solid, MS: 144 (MH$^+$).

8.2
In a sealed tube, 50 mg (0.15 mmol) of (RS,SR)-2-benzenesulfonyl-2-(3-oxo-cyclohexyl)-propionic acid methyl ester in 4 mL of glacial acetic acid were treated with 27 mg (0.18 mmol, 1.2 eq) of (6-chloro-pyridin-3-yl)-hydrazine hydrochloride and stirred at 115° C. for 3 hours. An aqueous solution of NaHCO$_3$ was added until pH=7 was reached, and the mixture was extracted with EtOAc. The combined organic phases were dried over Na$_2$SO$_4$, filtered and evaporated. A column chromatography on silica gel with heptane/EtOAc 1:1 followed by trituration with Et$_2$O yielded 52 mg (76%) of (RS,SR)-2-benzenesulfonyl-2-(2-chloro-6,7,8,9-tetrahydro-5H-pyrido[3,2-b]indol-7-yl)-propionic acid methyl ester as a white solid, MS: 433 (MH$^+$).

Example 9

(RS,SR)-2-benzenesulfonyl-2-(2,3,4,9-tetrahydro-1H-carbazol-2-yl)-propionic acid methyl ester In analogy to example 3.2, from (RS,SR)-2-benzenesulfonyl-2-(3-oxo-cyclohexyl)-propionic acid methyl ester and phenyl-hydrazine hydrochloride was prepared (RS,SR)-2-benzenesulfonyl-2-(2,3,4,9-tetrahydro-1H-carbazol-2-yl)-propionic acid methyl ester as a light yellow solid, MS: 398 (MH$^+$).

Example 10

(RS,SR)-2-benzenesulfonyl-2-(6-methanesulfonyl-2,3,4,9-tetrahydro-1H-carbazol-2-yl)-propionic acid methyl ester In analogy to example 3.2, from (RS,SR)-2-benzenesulfonyl-2-(3-oxo-cyclohexyl)-propionic acid methyl ester and (4-methanesulfonyl-phenyl)-hydrazine hydrochloride was prepared (RS,SR)-2-benzenesulfonyl-2-(6-methanesulfonyl-2,3,4,9-tetrahydro-1H-carbazol-2-yl)-propionic acid methyl ester as a light yellow solid, MS: 476 (MH$^+$).

Example 11

(RS,SR)-2-benzenesulfonyl-2-(8-fluoro-2,3,4,9-tetrahydro-1H-carbazol-2-yl)-propionic acid methyl ester In analogy to example 3.2, from (RS,SR)-2-benzenesulfonyl-2-(3-oxo-cyclohexyl)-propionic acid methyl ester and (2-fluoro-phenyl)-hydrazine hydrochloride was prepared (RS,SR)-2-benzenesulfonyl-2-(8-fluoro-2,3,4,9-tetrahydro-1H-carbazol-2-yl)-propionic acid methyl ester as a light yellow solid, MS: 416 (MH$^+$).

Example 12

(RS,SR)-benzenesulfonyl-(6-chloro-2,3,4,9-tetrahydro-1H-carbazol-2-yl)-fluoro-acetic acid methyl ester 12.1
To a stirred solution of 10 g (0.032 mol) of benzenesulfonyl-(3-oxo-cyclohexyl)-acetic acid methyl ester in 110 mL of DMF at 0° C., 1.42 g (0.035 mol, 1.1 eq) of NaH (60%) were added. The reaction mixture was stirred at this temperature for one hour, and 15.71 g (0.048 mol, 1.5 eq) of N-fluorobenzenesulfonimide were added. After 2 hours at RT, the reaction mixture was poured into water and extracted with EtOAc. The combined organic phases were dried over Na$_2$SO$_4$, filtered and evaporated. The resulting two diastereomers were separated by column chromatography on silica gel with heptane/EtOAc 2:1, yielding 3.06 g (27%) of (RS,SR)-benzenesulfonyl-fluoro-(3-oxo-cyclohexyl)-acetic acid methyl ester as a white solid, MS: 329 (MH$^+$) and 3.2 g (28%) of (RR,SS)-benzenesulfonyl-fluoro-(3-oxo-cyclohexyl)-acetic acid methyl ester as a white solid, MS: 329 (MH$^+$).
12.2
To 1.70 g (5.2 mmol) (RS,SR)-benzenesulfonyl-fluoro-(3-oxo-cyclohexyl)-acetic acid methyl ester in glacial acetic acid (20 mL), 1.05 g (5.72 mmol, 1.1 eq) of (4-chloro-phenyl)-hydrazine hydrochloride were added and the reaction mixture was stirred at 40° C. over night. An aqueous solution of NaHCO$_3$ was added until pH=7 was reached, and the mixture was extracted with EtOAc. The combined organic phases were dried over Na$_2$SO$_4$, filtered and evaporated. A column chromatography on silica gel with heptane/EtOAc 2:1 followed by a trituration from Et$_2$O yielded 1.56 g (70%) of (RS,SR)-benzenesulfonyl-(6-chloro-2,3,4,9-tetrahydro-1H-carbazol-2-yl)-fluoro-acetic acid methyl ester as a white solid, MS: 436 (MH$^+$).

The enantiomers were separated by preparative chiral HPLC. Column: chiralpak AD, solvent: 20% isopropanol/heptane Example 13

(RS,SR)-benzenesulfonyl-fluoro-(6-methyl-2,3,4,9-tetrahydro-1H-carbazol-2-yl)-acetic acid methyl ester In analogy to example 12.2, from (RS,SR)-benzenesulfonyl-fluoro-(3-oxo-cyclohexyl)-acetic acid methyl ester and (4-methyl-phenyl)-hydrazine hydrochloride was prepared (RS,SR)-benzenesulfonyl-fluoro-(6-methyl-2,3,4,9-tetrahydro-1H-carbazol-2-yl)-acetic acid methyl ester as a light yellow solid, MS: 416 (MH$^+$).

Example 14

(RS,SR)-benzenesulfonyl-(6-cyano-2,3,4,9-tetrahydro-1H-carbazol-2-yl)-fluoro-acetic acid methyl ester In analogy to example 12.2, from (RS,SR)-benzenesulfonyl-fluoro-(3-oxo-cyclohexyl)-acetic acid methyl ester and (4-cyano-phenyl)-hydrazine hydrochloride was prepared (RS,SR)-benzenesulfonyl-(6-cyano-2,3,4,9-tetrahydro-1H-carbazol-2-yl)-fluoro-acetic acid methyl ester as a light yellow solid, MS: 427 (MH$^+$).

Example 15

(RS,SR)-benzenesulfonyl-(6-bromo-2,3,4,9-tetrahydro-1H-carbazol-2-yl)-fluoro-acetic acid methyl ester In analogy to example 12.2, from (RS,SR)-benzenesulfonyl-fluoro-(3-oxo-cyclohexyl)-acetic acid methyl ester and (4-bromo-phenyl)-hydrazine hydrochloride was prepared (RS,SR)-benzenesulfonyl-(6-bromo-2,3,4,9-tetrahydro-1H-carbazol-2-yl)-fluoro-acetic acid methyl ester as a white solid, MS: 480; 482 (MH$^+$).

Example 16

(RS,SR)-benzenesulfonyl-(2-chloro-6,7,8,9-tetrahydro-5H-pyrido[3,2-b]indol-7-yl)-fluoro-acetic acid methyl ester In analogy to example 8.2, from (RS,SR)-benzenesulfonyl-fluoro-(3-oxo-cyclohexyl)-acetic acid methyl ester and (6-chloro-pyridin-3-yl)-hydrazine hydrochloride (example 8.1) was prepared (RS,SR)-benzenesulfonyl-(2-chloro-6,7,8,9-tetrahydro-5H-pyrido[3,2-b]indol-7-yl)-fluoro-acetic acid methyl ester as a white solid, MS: 437 (MH$^+$).

Example 17-18

(RS,SR)-benzenesulfonyl-(6-bromo-7-fluoro-2,3,4,9-tetrahydro-1H-carbazol-2-yl)-fluoro-acetic acid methyl ester and (RS,SR)-benzenesulfonyl-(6-bromo-5-fluoro-2,3,4,9-tetrahydro-1H-carbazol-2-yl)-fluoro-acetic acid methyl ester In analogy to example 12.2, from (RS,SR)-benzenesulfonyl-fluoro-(3-oxo-cyclohexyl)-acetic acid methyl ester and (4-bromo-3-fluoro-phenyl)-hydrazine hydrochloride was prepared (RS,SR)-benzenesulfonyl-(6-bromo-7-fluoro-2,3,4,9-tetrahydro-1H-carbazol-2-yl)-fluoro-acetic acid methyl ester as a white solid, MS: 515; 517 ($MNH_4^+$); (example 17) and (RS,SR)-benzenesulfonyl-(6-bromo-5-fluoro-2,3,4,9-tetrahydro-1H-carbazol-2-yl)-fluoro-acetic acid methyl ester as a white solid, MS: 515; 517 ($MNH_4^+$); (example 18). The two regioisomers were obtained in a ratio of 1:1, and separated by column chromatography on silica gel with Heptane/EtOAc 2:1.

Example 19

(RS,SR)-2-benzenesulfonyl-2-(7-chloro-1,2,3,4-tetrahydro-cyclopenta[b]indol-2-yl)-propionic acid methyl ester 19.1
To a stirred solution of 1.26 g (5.9 mmol) of methyl phenylsulfonylacetate in 20 mL of MeOH at 0° C., 0.22 mL (1.17 mmol, 0.2 eq) of a solution of sodium methoxide (5.4 M in MeOH) were added. After 15 min, 0.53 g (6.5 mmol, 1.1 eq) of cyclopent-2-enone were added. The reaction mixture was allowed to reached RT within 4 hours, diluted with saturated aqueous $NH_4Cl$ and extracted with EtOAc. The combined organic phases were dried over $Na_2SO_4$, filtered and evaporated. Column chromatography on silica gel with heptane/EtOAc 1:1 yielded 1.34 g (77%) of benzenesulfonyl-(3-oxo-cyclopentyl)-acetic acid methyl ester as a racemic mixture of diastereomers, colorless oil, MS: 297 ($MH^+$).

19.2
To a stirred solution of 2.4 g (8.1 mmol) of benzenesulfonyl-(3-oxo-cyclopentyl)-acetic acid methyl ester in 15 mL of DMF at 0° C., 389 mg (8.9 mmol, 1.1 eq) of NaH (60%) were added. The reaction mixture was stirred at this temperature for one hour, and 1.72 g (12.1 mmol, 1.5 eq) of methyliodide were added. After 2 hours at RT, the reaction mixture was poured into water and extracted with EtOAc. The combined organic phases were dried over $Na_2SO_4$, filtered and evaporated. The resulting two diastereomers were separated by column chromatography on silica gel with heptane/EtOAc (from 2:1 to 2:1) yielded 0.78 g (31%) of (RS,SR)-2-benzenesulfonyl-2-(3-oxo-cyclopentyl)-propionic acid methyl ester as a white solid, MS: 311 ($MH^+$) and 0.53 g (21%) of (RR,SS)-2-benzenesulfonyl-2-(3-oxo-cyclopentyl)-propionic acid methyl ester as a white solid, MS: 311 ($MH^+$).

19.3
To 100 mg (0.32 mmol) of (RS,SR)-2-benzenesulfonyl-2-(3-oxo-cyclopentyl)-propionic acid methyl ester in glacial acetic acid (3 mL), 63 mg (0.35 mmol, 1.1 eq) of (4-chloro-phenyl)-hydrazine hydrochloride were added and the reaction mixture was heated at 70° C. for about 5 hours. Until completion, the reaction was monitored by HPLC and TLC. An aqueous solution of $NaHCO_3$ was added until pH=7 was reached, and the mixture was extracted with EtOAc. The combined organic phases were dried over $Na_2SO_4$, filtered and evaporated. A column chromatography on silica gel with heptane/EtOAc 1:1 followed by a trituration with $Et_2O$ yielded 45 mg (34%) of (RS,SR)-2-benzenesulfonyl-2-(7-chloro-1,2,3,4-tetrahydro-cyclopenta[b]indol-2-yl)-propionic acid methyl ester as a light yellow solid, MS: 418 ($MH^+$).

Example 20

(RS,SR)-2-benzenesulfonyl-2-(7-bromo-1,2,3,4-tetrahydro-cyclopenta[b]indol-2-yl)-propionic acid methyl ester In analogy to example 19.3, from (RS,SR)-2-benzenesulfonyl-2-(3-oxo-cyclopentyl)-propionic acid methyl ester and (4-bromo-phenyl)-hydrazine hydrochloride was prepared (RS,SR)-2-benzenesulfonyl-2-(7-bromo-1,2,3,4-tetrahydro-cyclopenta[b]indol-2-yl)-propionic acid methyl ester as a light yellow solid, MS: 461; 463 ($MH^+$).

Example 21

(RS,SR)-2-benzenesulfonyl-2-(7-cyano-1,2,3,4-tetrahydro-cyclopenta[b]indol-2-yl)-propionic acid methyl ester In analogy to example 19.3, from (RS,SR)-2-benzenesulfonyl-2-(3-oxo-cyclopentyl)-propionic acid methyl ester and (4-cyano-phenyl)-hydrazine hydrochloride was prepared (RS,SR)-2-benzenesulfonyl-2-(7-cyano-1,2,3,4-tetrahydro-cyclopenta[b]indol-2-yl)-propionic acid methyl ester as a light brown solid, MS: 409 ($MH^+$).

Example 22

(RS,SR)-2-benzenesulfonyl-2-(7-methyl-1,2,3,4-tetrahydro-cyclopenta[b]indol-2-yl)-propionic acid methyl ester In analogy to example 19.3, from (RS,SR)-2-benzenesulfonyl-2-(3-oxo-cyclopentyl)-propionic acid methyl ester and (4-methyl-phenyl)-hydrazine hydrochloride was prepared (RS,SR)-2-benzenesulfonyl-2-(7-methyl-1,2,3,4-tetrahydro-cyclopenta[b]indol-2-yl)-propionic acid methyl ester as a white solid, MS: 398 ($MH^+$).

Example 23

(RS,SR)-benzenesulfonyl-(7-chloro-1,2,3,4-tetrahydro-cyclopenta[b]indol-2-yl)-fluoro-acetic acid methyl ester 23.1
To a stirred solution of 1.34 g (4.5 mmol) of benzenesulfonyl-(3-oxo-cyclopentyl)-acetic acid methyl ester in 15 mL of DMF at 0° C., 199 mg (5.0 mmol, 1.1 eq) of NaH (60%) were added. The reaction mixture was stirred at this temperature for one hour, and 2.14 g (6.75 mmol, 1.5 eq) of N-fluorobenzenesulfonimide were added. After 2 hours at RT, the reaction mixture was poured into water and extracted with EtOAc. The combined organic phases were dried over $Na_2SO_4$, filtered and evaporated. The resulting two diastereomers were separated by column chromatography on silica gel with heptane/EtOAc (from 2:1 to 2:1) yielding 0.40 g (28%) of (RS,SR)-benzenesulfonyl-fluoro-(3-oxo-cyclopentyl)-acetic acid methyl ester as a white solid, MS: 332 (MNH$_4^+$) and 0.52 g (37%) of (RR,SS)-benzenesulfonyl-fluoro-(3-oxo-cyclopentyl)-acetic acid methyl ester as a white solid, MS: 332 (MNH$_4^+$).

23.2

In analogy to example 19.3, from (RS,SR)-benzenesulfonyl-fluoro-(3-oxo-cyclopentyl)-acetic acid methyl ester and (4-chloro-phenyl)-hydrazine hydrochloride was prepared (RS,SR)-benzenesulfonyl-(7-chloro-1,2,3,4-tetrahydro-cyclopenta[b]indol-2-yl)-fluoro-acetic acid methyl ester as a white solid, MS: 439 (MNH$_4^+$).

Example 24

(RS,SR)-benzenesulfonyl-(7-bromo-1,2,3,4-tetrahydro-cyclopenta[b]indol-2-yl)-fluoro-acetic acid methyl ester In analogy to example 19.3, from (RS,SR)-benzenesulfonyl-fluoro-(3-oxo-cyclopentyl)-acetic acid methyl ester and (4-bromo-phenyl)-hydrazine hydrochloride was prepared (RS,SR)-benzenesulfonyl-(7-bromo-1,2,3,4-tetrahydro-cyclopenta[b]indol-2-yl) -fluoro-acetic acid methyl ester as a white solid, MS: 466; 468 (MH$^+$).

Example 25

(RS,SR)-benzenesulfonyl-(5-chloro-1,2,3,8-tetrahydro-4,8-diaza-cyclopenta[a]inden-2-yl)-fluoro-acetic acid methyl ester In analogy to example 19.3, from (RS,SR)-benzenesulfonyl-fluoro-(3-oxo-cyclopentyl)-acetic acid methyl ester and (6-chloro-pyridin-3-yl)-hydrazine hydrochloride was prepared (RS,SR)-benzenesulfonyl-(5-chloro-1,2,3,8-tetrahydro-4,8-diaza-cyclopenta[a]inden-2-yl)-fluoro-acetic acid methyl ester as a white solid, MS: 423 (MH$^+$).

Example 26-27

(RS,SR)-benzenesulfonyl-(7-bromo-6-fluoro-1,2,3,4-tetrahydro-cyclopenta[b]indol-2-yl)-fluoro-acetic acid methyl ester and (RS,SR)-benzenesulfonyl-(7-bromo-8-fluoro-1,2,3,4-tetrahydro-cyclopenta[b]indol-2-yl)-fluoro-acetic acid methyl ester In analogy to example 19.3, from (RS,SR)-benzenesulfonyl-fluoro-(3-oxo-cyclopentyl)-acetic acid methyl ester and (4-bromo-3-fluoro-phenyl)-hydrazine hydrochloride was prepared (RS,SR)-benzenesulfonyl-(7-bromo-6-fluoro-1,2,3,4-tetrahydro-cyclopenta[b]indol-2-yl)-fluoro-acetic acid methyl ester as a light brown solid, MS: 484; 486 (MH$^+$); (example 26) and (RS,SR)-benzenesulfonyl-(7-bromo-8-fluoro-1,2,3,4-tetrahydro-cyclopenta[b]indol-2-yl)-fluoro-acetic acid methyl ester as a light brown solid, MS: 484; 486 (MH$^+$); (example 27). The two regioisomers were obtained in a ratio of 1:1 and separated by column chromatography on silica gel with heptane/EtOAc 2:1.

Example 28

(RS,SR)-2-(6-chloro-2,3,4,9-tetrahydro-1H-carbazol-2-yl)-2-(naphthalene-1-sulfonyl)-propionic acid methyl ester 28.1

To a stirred suspension of 3.1 g (0.019 mol) of naphthalene-1-thiol and 2.94 g (0.021 mol, 1.1 eq) of K$_2$CO$_3$ in 100 mL of propan-2-one cooled at 0° C., 3.15 g (0.029 mol, 1.5 eq) of chloro-acetic acid methyl ester were added in one portion. The ice bath was removed and the reaction mixture was stirred an additional 4 hours. The reaction was filtered, the solvent evaporated and the resulting residue was taken up in 100 mL of MeOH. 14.3 g (0.023 mol, 1.2 eq) of oxone (potassium peroxymonosulfate) were added and the reaction mixture was stirred over night at RT. The salts were filtered off, the solvent evaporated and the residue purified by column chromatography on silica gel with heptane/EtOAc (from 4:1 to 1:2) to afford 2.78 g (55%) of (naphthalene-1-sulfonyl)-acetic acid methyl ester as a light yellow oil, MS: 265 (MH$^+$).

28.2

To a stirred solution of 2.75 g (0.010 mol) of (naphthalene-1-sulfonyl)-acetic acid methyl ester in 100 mL of MeOH at RT, 0.19 mL (0.011 mol, 1.1 eq) of a solution of sodium methoxide (5.4 M in MeOH) were added. After 15 min, 1.1 g (0.011 mol, 1.1 eq) of 2-cyclohexen-1-one were added. The reaction mixture was stirred at RT for 3 hours followed by an additional 4 hours at 60° C., diluted with aqueous NH$_4$Cl and extracted with EtOAc. The combined organic phases were dried over Na$_2$SO$_4$, filtered and evaporated. Column chromatography on silica gel with heptane/EtOAc (from 4:1 to 1:2) yielded 1.78 g (48%) of (naphthalene-1-sulfonyl)-(3-oxo-cyclohexyl)-acetic acid methyl ester as a racemic mixture of diastereomers, light orange oil, MS: 361 (MH$^+$).

28.3

In analogy to example 3.1:1.74 g (4.8 mmol) of (naphthalene-1-sulfonyl)-(3-oxo-cyclohexyl)-acetic acid methyl ester was dissolved in 10 mL of DMF at 0° C. 232 mg (5.3 mmol, 1.1 eq) of NaH (60%) were added and the reaction mixture was stirred 30 minutes before the addition of 1.03 g (7.2 mmol, 1.5 eq) of methyliodide. The reaction was stirred over night, poured on water and extracted with EtOAc. The combined organic phases were dried over Na$_2$SO$_4$, filtered and evaporated. The resulting two diastereomers were separated by column chromatography on silica gel with AcOEt/heptane 2:1, yielded 0.30 g (17%) of (RS,SR)-2-(naphthalene-1-sulfonyl)-2-(3-oxocyclohexyl)-propionic acid methyl ester as a white foam MS: 375 (MH$^+$) and 0.42 g (23%) of (RR,SS)-2-(naphthalene-1-sulfonyl)-2-(3-oxocyclohexyl)-propionic acid methyl ester as a white solid MS: 375 (MH$^+$).

28.4

In analogy to example 3.2, from (RS,SR)-2-(naphthalene-1-sulfonyl)-2-(3-oxo-cyclohexyl)-propionic acid methyl ester and (4-chloro-phenyl)-hydrazine hydrochloride was prepared (RS,SR)-2-(6-chloro-2,3,4,9-tetrahydro-1H-carbazol-2-yl)-2-(naphthalene-1-sulfonyl)-propionic acid methyl ester as a brown solid, MS: 483 (MH$^+$).

Example 29

(RS,SR)-2-(6-chloro-2,3,4,9-tetrahydro-1H-carbazol-2-yl)-2-(naphthalene-2-sulfonyl)-propionic acid methyl ester 29.1

In analogy to example 28.1, from naphthalene-2-thiol and chloro-acetic acid methyl ester was prepared (naphthalene-2-sulfonyl)-acetic acid methyl ester as a white solid, MS: 265 (MH$^+$).

29.2

In analogy to example 28.2, from (naphthalene-2-sulfonyl)-acetic acid methyl ester and cyclohexen-1-one was prepared (naphthalene-2-sulfonyl)-(3-oxo-cyclohexyl)-acetic acid methyl ester as a racemic mixture of diastereomers, light orange oil, MS: 361 (MH$^+$).

29.3

In analogy to example 28.3, from (naphthalene-2-sulfonyl)-(3-oxo-cyclohexyl)-acetic acid methyl ester and methyliodide was prepared (RS,SR)-2-(naphthalene-2-sulfonyl)-2-(3-oxo-cyclohexyl)-propionic acid methyl ester as a white solid, MS: 375 (MH$^+$).

29.4

In analogy to example 3.2, from (RS,SR)-2-(naphthalene-2-sulfonyl)-2-(3-oxo-cyclohexyl)-propionic acid methyl ester and (4-chloro-phenyl)-hydrazine hydrochloride was prepared (RS,SR)-2-(6-chloro-2,3,4,9-tetrahydro-1H-carbazol-2-yl)-2-(naphthalene-2-sulfonyl)-propionic acid methyl ester as a light yellow solid, MS: 483 (MH$^+$).

Example 30

(RS,SR)-2-(6-chloro-2,3,4,9-tetrahydro-1H-carbazol-2-yl)-2-(3,4-dichloro-benzenesulfonyl)-propionic acid methyl ester 30.1

In analogy to example 28.1, from 3,4-dichloro-benzenethiol and chloro-acetic acid methyl ester was prepared (3,4-dichloro-benzenesulfonyl)-acetic acid methyl ester as a white solid, MS: 284 (MH$^+$).

30.2

In analogy to example 28.2, from (3,4-dichloro-benzenesulfonyl)-acetic acid methyl ester and cyclohexen-1-one was prepared (3,4-dichloro-benzenesulfonyl)-(3-oxo-cyclohexyl)-acetic acid methyl ester as a racemic mixture of diastereomers, light yellow solid, MS: 380 (MH$^+$).

30.3

In analogy to example 28.3, from (3,4-dichloro-benzenesulfonyl)-(3-oxo-cyclohexyl)-acetic acid methyl ester and methyliodide was prepared (RS,SR)-2-(3,4-dichloro-benzenesulfonyl)-2-(3-oxo-cyclohexyl)-propionic acid methyl ester as a white solid, MS: 394 (MH$^+$).

30.4

In analogy to example 3.2, from (RS,SR)-2-(3,4-dichloro-benzenesulfonyl)-2-(3-oxo-cyclohexyl)-propionic acid methyl ester and (4-chloro-phenyl)-hydrazine hydrochloride was prepared (RS,SR)-2-(6-chloro-2,3,4,9-tetrahydro-1H-carbazol-2-yl)-2-(3,4-dichloro-benzenesulfonyl)-propionic acid methyl ester as a light brown solid, MS: 501 (MH$^+$).

Example 31

(RS,SR)-2-(6-chloro-2,3,4,9-tetrahydro-1H-carbazol-2-yl)-2-(toluene-3-sulfonyl)-propionic acid methyl ester 31.1

In analogy to example 28.1, from 3-methyl-benzenethiol and chloro-acetic acid methyl ester was prepared (toluene-3-sulfonyl)-acetic acid methyl ester as a colorless oil, MS: 229 (MH$^+$).

31.2

In analogy to example 28.2, from (toluene-3-sulfonyl)-acetic acid methyl ester and cyclohexen-1-one was prepared (3-oxo-cyclohexyl)-(toluene-3-sulfonyl)-acetic acid methyl ester as a racemic mixture of diastereomers, light yellow oil, MS: 325 (MH$^+$).

31.3

In analogy to example 28.3, from (3-oxo-cyclohexyl)-(toluene-3-sulfonyl)-acetic acid methyl ester and methyliodide was prepared (RS,SR)-2-(3-oxo-cyclohexyl)-(toluene-3-sulfonyl)-propionic acid methyl ester as a white solid, MS: 339 (MH$^+$).

31.4

In analogy to example 3.2, from (RS,SR)-2-(3-oxo-cyclohexyl)-(toluene-3-sulfonyl)-propionic acid methyl ester and (4-chloro-phenyl)-hydrazine hydrochloride was prepared (RS,SR)-2-(6-chloro-2,3,4,9-tetrahydro-1H-carbazol-2-yl)-2-(toluene-3-sulfonyl)-propionic acid methyl ester as a light brown solid, MS: 446 (MH$^+$).

Example 32

(RS,SR)-2-(6-chloro-2,3,4,9-tetrahydro-1H-carbazol-2-yl)-2-(3-methoxy-benzenesulfonyl)-propionic acid methyl ester 32.1

In analogy to example 28.1, from 3-methoxy-benzenethiol and chloro-acetic acid methyl ester was prepared (3-methoxy-benzenesulfonyl)-acetic acid methyl ester as a light brown oil, MS: 245 (MH$^+$).

32.2

In analogy to example 28.2, from (3-methoxy-benzenesulfonyl)-acetic acid methyl ester and cyclohexen-1-one was prepared (3-methoxy-benzenesulfonyl)-(3-oxo-cyclohexyl)-acetic acid methyl ester as a racemic mixture of diastereomers, light orange oil, MS: 341 (MH$^+$).

32.3

In analogy to example 28.3, from (3-methoxy-benzenesulfonyl)-(3-oxo-cyclohexyl)-acetic acid methyl ester and methyliodide was prepared (RS,SR)-2-(3-methoxy-benzenesulfonyl)-2-(3-oxo-cyclohexyl)-propionic acid methyl ester as a colorless oil, MS: 355 (MH$^+$).

32.4

In analogy to example 3.2, from (RS,SR)-2-(3-methoxy-benzenesulfonyl)-2-(3-oxo-cyclohexyl)-propionic acid methyl ester and (4-chloro-phenyl)-hydrazine hydrochloride was prepared (RS,SR)-2-(6-chloro-2,3,4,9-tetrahydro-1H-carbazol-2-yl)-2-(3-methoxy-benzenesulfonyl)-propionic acid methyl ester as a light brown solid, MS: 462 (MH$^+$).

Example 33

(RS,SR)-2-(2-chloro-benzenesulfonyl)-2-(6-chloro-2,3,4,9-tetrahydro-1H-carbazol-2-yl)-propionic acid methyl ester 33.1

In analogy to example 28.1, from 2-chloro-benzenethiol and bromo-acetic acid methyl ester was prepared (2-chloro-benzenesulfonyl)-acetic acid methyl ester as a white solid, MS: 249 (MH$^+$).

33.2

In analogy to example 28.2, from (2-chloro-benzenesulfonyl)-acetic acid methyl ester and cyclohexen-1-one was prepared (2-chloro-benzenesulfonyl)-(3-oxo-cyclohexyl)-acetic acid methyl ester as a racemic mixture of diastereomers, colorless oil, MS: 345 (MH$^+$).

33.3

In analogy to example 28.3, from (2-chloro-benzenesulfonyl)-(3-oxo-cyclohexyl)-acetic acid methyl ester and methyliodide was prepared (RS,SR)-2-(2-chloro-benzenesulfonyl)-2-(3-oxo-cyclohexyl)-propionic acid methyl ester as white crystals, MS: 359 (MH$^+$).

33.4
In analogy to example 3.2, from (RS,SR)-2-(2-chloro-benzenesulfonyl)-2-(3-oxo-cyclohexyl)-propionic acid methyl ester and (4-chloro-phenyl)-hydrazine hydrochloride was prepared (RS,SR)-2-(2-chloro-benzenesulfonyl)-2-(6-chloro-2,3,4,9-tetrahydro-1H-carbazol-2-yl)-propionic acid methyl ester as a light brown solid, MS: 467 (MH$^+$).

Example 34

(RS,SR)-2-(6-chloro-2,3,4,9-tetrahydro-1H-carbazol-2-yl)-2-(2-methoxy-benzenesulfonyl)-propionic acid methyl ester 34.1
In analogy to example 28.1, from 2-methoxy-benzenethiol and chloro-acetic acid methyl ester was prepared (2-methoxy-benzenesulfonyl)-acetic acid methyl ester as white crystals, MS: 245 (MH$^+$).
34.2
In analogy to example 28.2, from (2-methoxy-benzenesulfonyl)-acetic acid methyl ester and cyclohexen-1-one was prepared (2-methoxy-benzenesulfonyl)-(3-oxo-cyclohexyl)-acetic acid methyl ester as a racemic mixture of diastereomers, light yellow oil, MS: 341 (MH$^+$).
34.3
In analogy to example 28.3, from (2-methoxy-benzenesulfonyl)-(3-oxo-cyclohexyl)-acetic acid methyl ester and methyliodide was prepared (RS,SR)-2-(2-methoxy-benzenesulfonyl)-2-(3-oxo-cyclohexyl)-propionic acid methyl ester as a light yellow solid, MS: 355 (MH$^+$).
34.4
In analogy to example 3.2, from (RS,SR)-2-(2-methoxy-benzenesulfonyl)-2-(3-oxo-cyclohexyl)-propionic acid methyl ester and (4-chloro-phenyl)-hydrazine hydrochloride was prepared (RS,SR)-2-(6-chloro-2,3,4,9-tetrahydro-1H-carbazol-2-yl)-2-(2-methoxy-benzenesulfonyl)-propionic acid methyl ester as a light brown solid, MS: 462 (MH$^+$).

Example 35

(RS,SR)-2-(6-chloro-2,3,4,9-tetrahydro-1H-carbazol-2-yl)-2-(4-fluoro-benzenesulfonyl)-propionic acid methyl ester 35.1
In analogy to example 28.1, from 4-fluoro-benzenethiol and bromo-acetic acid methyl ester was prepared (4-fluoro-benzenesulfonyl)-acetic acid methyl ester as a colorless oil, MS: 233 (MH$^+$).
35.2
In analogy to example 28.2, from (4-fluoro-benzenesulfonyl)-acetic acid methyl ester and cyclohexen-1-one was prepared (4-fluoro-benzenesulfonyl)-(3-oxo-cyclohexyl)-acetic acid methyl ester as a racemic mixture of diastereomers, white crystals, MS: 329 (MH$^+$).
35.3
In analogy to example 28.3, from (4-fluoro-benzenesulfonyl)-(3-oxo-cyclohexyl)-acetic acid methyl ester and methyliodide was prepared (RS,SR)-2-(4-fluoro-benzenesulfonyl)-2-(3-oxo-cyclohexyl)-propionic acid methyl ester as a light yellow solid, MS: 343 (MH$^+$).
35.4
In analogy to example 3.2, from (RS,SR)-2-(4-fluoro-benzenesulfonyl)-2-(3-oxo-cyclohexyl)-propionic acid methyl ester and (4-chloro-phenyl)-hydrazine hydrochloride was prepared (RS,SR)-2-(6-chloro-2,3,4,9-tetrahydro-1H-carbazol-2-yl)-2-(4-fluoro-benzenesulfonyl)-propionic acid methyl ester as a white solid, MS: 450 (MH$^+$).

Example 36

(RS,SR)-2-(3-chloro-benzenesulfonyl)-2-(6-chloro-2,3,4,9-tetrahydro-1H-carbazol-2-yl)-propionic acid methyl ester 36.1
In analogy to example 28.1, from 3-chloro-benzenethiol and bromo-acetic acid methyl ester was prepared (3-chloro-benzenesulfonyl)-acetic acid methyl ester as a colorless oil, MS: 249 (MH$^+$).
36.2
In analogy to example 28.2, from (3-chloro-benzenesulfonyl)-acetic acid methyl ester and cyclohexen-1-one was prepared (3-chloro-benzenesulfonyl)-(3-oxo-cyclohexyl)-acetic acid methyl ester as a racemic mixture of diastereomers, light yellow oil, MS: 345 (MH$^+$).
36.3
In analogy to example 28.3, from (3-chloro-benzenesulfonyl)-(3-oxo-cyclohexyl)-acetic acid methyl ester and methyliodide was prepared (RS,SR)-2-(3-chloro-benzenesulfonyl)-2-(3-oxo-cyclohexyl)-propionic acid methyl ester as white solid, MS: 359 (MH$^+$).
36.4
In analogy to example 3.2, from (RS,SR)-2-(3-chloro-benzenesulfonyl)-2-(3-oxo-cyclohexyl)-propionic acid methyl ester and (4-chloro-phenyl)-hydrazine hydrochloride was prepared (RS,SR)-2-(3-chloro-benzenesulfonyl)-2-(6-chloro-2,3,4,9-tetrahydro-1H-carbazol-2-yl)-propionic acid methyl ester as a white solid, MS: 467 (MH$^+$).

Example 37

(RS,SR)-(6-chloro-2,3,4,9-tetrahydro-1H-carbazol-2-yl)-fluoro-(4-fluoro-benzenesulfonyl)-acetic acid methyl ester 37.1
In analogy to example 12.1, from (4-fluoro-benzenesulfonyl)-(3-oxo-cyclohexyl)-acetic acid methyl ester and N-fluorobenzenesulfonimide was prepared (RS,SR)-fluoro-(4-fluoro-benzenesulfonyl)-(3-oxo-cyclohexyl)-acetic acid methyl ester as a colorless oil, MS: 347 (MH$^+$).
37.2
In analogy to example 12.2, from (RS,SR)-fluoro-(4-fluoro-benzenesulfonyl)-(3-oxo-cyclohexyl)-acetic acid methyl ester and (4-chloro-phenyl)-hydrazine hydrochloride was prepared (RS,SR)-(6-chloro-2,3,4,9-tetrahydro-1H-carbazol-2-yl)-fluoro-(4-fluoro-benzenesulfonyl)-acetic acid methyl ester as a white solid, MS: 454 (MH$^+$).

Example 38

(RS,SR)-(3-chloro-benzenesulfonyl)-(6-chloro-2,3,4,9-tetrahydro-1H-carbazol-2-yl)-fluoro-acetic acid methyl ester 38.1
In analogy to example 12.1, from (3-chloro-benzenesulfonyl)-(3-oxo-cyclohexyl)-acetic acid methyl ester and N-fluorobenzenesulfonimide was prepared (RS,SR)-(3-chloro-benzenesulfonyl)-fluoro-(3-oxo-cyclohexyl)-acetic acid methyl ester as a white solid, MS: 363 (MH$^+$).

38.2

In analogy to example 12.2, from (RS,SR)-(3-chloro-benzenesulfonyl)-fluoro-(3-oxo-cyclohexyl)-acetic acid methyl and (4-chloro-phenyl)-hydrazine hydrochloride was prepared (RS,SR)-(3-chloro-benzenesulfonyl)-(6-chloro-2,3,4,9-tetrahydro-1H-carbazol-2-yl)-fluoro-acetic acid methyl ester as a white solid, MS: 471 (MH$^+$).

Example 39

(RS,SR)-(6-chloro-2,3,4,9-tetrahydro-1H-carbazol-2-yl)-fluoro-(3-fluoro-benzenesulfonyl)-acetic acid methyl ester 39.1

In analogy to example 28.1, from 3-fluoro-benzenethiol and chloro-acetic acid methyl ester was prepared (3-fluoro-benzenesulfonyl)-acetic acid methyl ester as a colorless oil, MS: 233 (MH$^+$).

39.2

In analogy to example 28.2, from (3-fluoro-benzenesulfonyl)-acetic acid methyl ester and cyclohexen-1-one was prepared (3-fluoro-benzenesulfonyl)-(3-oxo-cyclohexyl)-acetic acid methyl ester as a racemic mixture of diastereomers, light yellow oil, MS: 329 (MH$^+$).

39.3

In analogy to example 12.1, from (3-fluoro-benzenesulfonyl)-(3-oxo-cyclohexyl)-acetic acid methyl ester and N-fluorobenzenesulfonimide was prepared (RS,SR)-fluoro-(3-fluoro-benzenesulfonyl)-(3-oxo-cyclohexyl)-acetic acid methyl ester as a white solid, MS: 347 (MH$^+$).

39.4

In analogy to example 12.2, from (RS,SR)-fluoro-(3-fluoro-benzenesulfonyl)-(3-oxo-cyclohexyl)-acetic acid methyl and (4-chloro-phenyl)-hydrazine hydrochloride was prepared (RS,SR)-(6-chloro-2,3,4,9-tetrahydro-1H-carbazol-2-yl)-fluoro-(3-fluoro-benzenesulfonyl)-acetic acid methyl ester as a white solid, MS: 454 (MH$^+$).

Example 40

(RS,SR)-(6-chloro-2,3,4,9-tetrahydro-1H-carbazol-2-yl)-(3,4-difluoro-benzenesulfonyl)-fluoro-acetic acid methyl ester 40.1

In analogy to example 28.1, from 3,4-difluoro-benzenethiol and chloro-acetic acid methyl ester was prepared (3,4-difluoro-benzenesulfonyl)-acetic acid methyl ester as a colorless oil, MS: 251 (MH$^+$).

40.2

In analogy to example 28.2, from (3,4-difluoro-benzenesulfonyl)-acetic acid methyl ester and cyclohexen-1-one was prepared (3,4-difluoro-benzenesulfonyl)-(3-oxo-cyclohexyl)-acetic acid methyl ester as a racemic mixture of diastereomers, light yellow oil, MS: 347 (MH$^+$).

40.3

In analogy to example 12.1, from (3,4-difluoro-benzenesulfonyl)-(3-oxo-cyclohexyl)-acetic acid methyl ester and N-fluorobenzenesulfonimide was prepared (RS,SR)-(3,4-difluoro-benzenesulfonyl)-fluoro-(3-oxo-cyclohexyl)-acetic acid methyl ester as a white solid, MS: 365 (MH$^+$).

40.4

In analogy to example 12.2, from (RS,SR)-(3,4-difluoro-benzenesulfonyl)-fluoro-(3-oxo-cyclohexyl)-acetic acid methyl ester and (4-chloro-phenyl)-hydrazine hydrochloride was prepared (RS,SR)-(6-chloro-2,3,4,9-tetrahydro-1H-carbazol-2-yl)-(3,4-difluoro-benzenesulfonyl)-fluoro-acetic acid methyl ester as a white solid, MS: 472 (MH$^+$).

Example 41

(RS,SR)-(6-chloro-2,3,4,9-tetrahydro-1H-carbazol-2-yl)-fluoro-(pyridine-3-sulfonyl)-acetic acid methyl ester 41.1

In analogy to example 28.1, from pyridine-3-thiol and chloro-acetic acid methyl ester was prepared (pyridine-3-sulfonyl)-acetic acid methyl ester as a yellow oil, MS: 216 (MH$^+$).

41.2

In analogy to example 28.2, from (pyridine-3-sulfonyl)-acetic acid methyl ester and cyclohexen-1-one was prepared (3-oxo-cyclohexyl)-(pyridine-3-sulfonyl)-acetic acid methyl ester as a racemic mixture of diastereomers, yellow oil, MS: 312 (MH$^+$).

41.3

In analogy to example 12.1, from (3-oxo-cyclohexyl)-(pyridine-3-sulfonyl)-acetic acid methyl ester and N-fluorobenzenesulfonimide was prepared (RS,SR)-fluoro-(3-oxo-cyclohexyl)-(pyridine-3-sulfonyl)-acetic acid methyl ester as white crystals, MS: 330 (MH$^+$).

41.4

In analogy to example 12.2, from (RS,SR)-fluoro-(3-oxo-cyclohexyl)-(pyridine-3-sulfonyl)-acetic acid methyl ester and (4-chloro-phenyl)-hydrazine hydrochloride was prepared (RS,SR)-(6-chloro-2,3,4,9-tetrahydro-1H-carbazol-2-yl)-fluoro-(pyridine-3-sulfonyl)-acetic acid methyl ester as a light yellow solid, MS: 437 (MH$^+$).

Example 42

(RS,SR)-(7-chloro-1,2,3,4-tetrahydro-cyclopenta[b]indol-2-yl)-fluoro-(3-methoxy-benzenesulfonyl)-acetic acid methyl ester 42.1

In analogy to example 19.1, from (3-methoxy-benzenesulfonyl)-acetic acid methyl ester and cyclopent-2-enone was prepared (3-methoxy-benzenesulfonyl)-(3-oxo-cyclopentyl)-acetic acid methyl ester as a racemic mixture of diastereomers, white solid, MS: 327 (MH$^+$).

42.2

In analogy to example 23.1, from (3-methoxy-benzenesulfonyl)-(3-oxo-cyclopentyl)-acetic acid methyl ester and N-fluorobenzenesulfonimide was prepared (RS,SR)-fluoro-(3-methoxy-benzenesulfonyl)-(3-oxo-cyclopentyl)-acetic acid methyl ester as a white solid, MS: 345 (MH$^+$).

42.3

In analogy to example 23.2, from (RS,SR)-fluoro-(3-methoxy-benzenesulfonyl)-(3-oxo-cyclopentyl)-acetic acid methyl ester and (4-chloro-phenyl)-hydrazine hydrochloride was prepared (RS,SR)-(7-chloro-1,2,3,4-tetrahydro-cyclopenta[b]indol-2-yl)-fluoro-(3-methoxy-benzenesulfonyl)-acetic acid methyl ester as a white solid, MS: 452 (MH$^+$).

Example 43

(RS,SR)-(3-chloro-benzenesulfonyl)-(7-chloro-1,2,3,4-tetrahydro-cyclopenta[b]indol-2-yl)-fluoro-acetic acid methyl ester 43.1
In analogy to example 19.1, from (3-chloro-benzenesulfonyl)-acetic acid methyl ester and cyclopent-2-enone was prepared (3-chloro-benzenesulfonyl)-(3-oxo-cyclopentyl)-acetic acid methyl ester as a racemic mixture of diastereomers, colorless oil, MS: 348 ($MNH_4^+$).

43.2
In analogy to example 23.1, from (3-chloro-benzenesulfonyl)-(3-oxo-cyclopentyl)-acetic acid methyl ester and N-fluorobenzenesulfonimide was prepared (RS,SR)-(3-chloro-benzenesulfonyl)-fluoro-(3-oxo-cyclopentyl)-acetic acid methyl ester as a white solid, MS: 366 ($MNH_4^+$).

43.3
In analogy to example 23.2, from (RS,SR)-(3-chloro-benzenesulfonyl)-fluoro-(3-oxo-cyclopentyl)-acetic acid methyl ester and (4-chloro-phenyl)-hydrazine hydrochloride was prepared (RS,SR)-(3-chloro-benzenesulfonyl)-(7-chloro-1,2,3,4-tetrahydro-cyclopenta[b]indol-2-yl)-fluoro-acetic acid methyl ester as a light brown solid, MS: 457 ($MH^+$).

Example 44

(RS,SR)-(7-chloro-1,2,3,4-tetrahydro-cyclopenta[b]indol-2-yl)-fluoro-(pyridine-2-sulfonyl)-acetic acid methyl ester 44.1
In analogy to example 28.1, from pyridine-2-thiol and chloro-acetic acid methyl ester was prepared (pyridine-2-sulfonyl)-acetic acid methyl ester as a colorless oil, MS: 216 ($MH^+$).

44.2
In analogy to example 19.1, from (pyridine-2-sulfonyl)-acetic acid methyl ester and cyclopent-2-enone was prepared (3-oxo-cyclopentyl)-(pyridine-2-sulfonyl)-acetic acid methyl ester as a racemic mixture of diastereomers, colorless oil, MS: 298 ($MH^+$).

44.3
In analogy to example 23.1, from (3-oxo-cyclopentyl)-(pyridine-2-sulfonyl)-acetic acid methyl ester and N-fluorobenzenesulfonimide was prepared (RS,SR)-fluoro-(3-oxo-cyclopentyl)-(pyridine-2-sulfonyl)-acetic acid methyl ester as a white solid, MS: 316 ($MH^+$).

44.4
In analogy to example 23.2, from (RS,SR)-fluoro-(3-oxo-cyclopentyl)-(pyridine-2-sulfonyl)-acetic acid methyl ester and (4-chloro-phenyl)-hydrazine hydrochloride was prepared (RS,SR)-(7-chloro-1,2,3,4-tetrahydro-cyclopenta[b]indol-2-yl)-fluoro-(pyridine-2-sulfonyl)-acetic acid methyl ester as a white solid, MS: 423 ($MH^+$).

Example 45

(RS,SR)-(7-chloro-1,2,3,4-tetrahydro-cyclopenta[b]indol-2-yl)-fluoro-(3-fluoro-benzenesulfonyl)-acetic acid methyl ester 45.1
In analogy to example 19.1, from (3-fluoro-benzenesulfonyl)-acetic acid methyl ester and cyclopent-2-enone was prepared (3-fluoro-benzenesulfonyl)-(3-oxo-cyclopentyl)-acetic acid methyl ester as a racemic mixture of diastereomers, colorless oil, MS: 315 ($MH^+$).

45.2
In analogy to example 23.1, from (3-fluoro-benzenesulfonyl)-(3-oxo-cyclopentyl)-acetic acid methyl ester and N-fluorobenzenesulfonimide was prepared (RS,SR)-fluoro-(3-fluoro-benzenesulfonyl)-(3-oxo-cyclopentyl)-acetic acid methyl ester as a white solid, MS: 333 ($MH^+$).

45.3
In analogy to example 23.2, from (RS,SR)-fluoro-(3-fluoro-benzenesulfonyl)-(3-oxo-cyclopentyl)-acetic acid methyl ester and (4-chloro-phenyl)-hydrazine hydrochloride was prepared (RS,SR)-(7-chloro-1,2,3,4-tetrahydro-cyclopenta[b]indol-2-yl)-fluoro-(3-fluoro-benzenesulfonyl)-acetic acid methyl ester as a light brown solid, MS: 440 ($MH^+$).

Example 46

(RS,SR)-(7-chloro-1,2,3,4-tetrahydro-cyclopenta[b]indol-2-yl)-(3,4-difluoro-benzenesulfonyl)-fluoro-acetic acid methyl ester 46.1
In analogy to example 19.1, from (3,4-difluoro-benzenesulfonyl)-acetic acid methyl ester and cyclopent-2-enone was prepared (3,4-difluoro-benzenesulfonyl)-(3-oxo-cyclopentyl)-acetic acid methyl ester as a racemic mixture of diastereomers, colorless oil, MS: 333 ($MH^+$).

46.2
In analogy to example 23.1, from (3,4-difluoro-benzenesulfonyl)-(3-oxo-cyclopentyl)-acetic acid methyl ester and N-fluorobenzenesulfonimide was prepared (RS,SR)-(3,4-difluoro-benzenesulfonyl)-fluoro-(3-oxo-cyclopentyl)-acetic acid methyl ester as a white solid, MS: 351 ($MH^+$).

46.3
In analogy to example 23.2, from (RS,SR)-(3,4-difluoro-benzenesulfonyl)-fluoro-(3-oxo-cyclopentyl)-acetic acid methyl ester and (4-chloro-phenyl)-hydrazine hydrochloride was prepared (RS,SR)-(7-chloro-1,2,3,4-tetrahydro-cyclopenta[b]indol-2-yl)-(3,4-difluoro-benzenesulfonyl)-fluoro-acetic acid methyl ester as a light brown solid, MS: 458 ($MH^+$).

Example 47

(RS,SR)-(7-chloro-1,2,3,4-tetrahydro-cyclopenta[b]indol-2-yl)-fluoro-(pyridine-3-sulfonyl)-acetic acid methyl ester 47.1
In analogy to example 19.1, from (pyridine-3-sulfonyl)-acetic acid methyl ester and cyclopent-2-enone was prepared (pyridine-3-sulfonyl)-(3-oxo-cyclopentyl)-acetic acid methyl ester as a racemic mixture of diastereomers, yellow oil, MS: 298 ($MH^+$).

47.2
In analogy to example 23.1, from (pyridine-3-sulfonyl)-(3-oxo-cyclopentyl)-acetic acid methyl ester and N-fluorobenzenesulfonimide was prepared (RS,SR)-fluoro-(3-oxo-cyclopentyl)-(pyridine-3-sulfonyl)-acetic acid methyl ester as white crystals, MS: 333 ($MNH_4^+$).

47.3
In analogy to example 23.2, from (RS,SR)-fluoro-(3-oxo-cyclopentyl)-(pyridine-3-sulfonyl)-acetic acid methyl ester and (4-chloro-phenyl)-hydrazine hydrochloride was prepared (RS,SR)-(7-chloro-1,2,3,4-tetrahydro-cyclopenta[b]

indol-2-yl)-fluoro-(pyridine-3-sulfonyl)-acetic acid methyl ester as a light brown solid, MS: 423 (MH$^+$).

Example 48

(RS,SR)-2-(7-chloro-1,2,3,4-tetrahydro-cyclopenta [b]indol-2-yl)-2-(pyridine-2-sulfonyl)-propionic acid methyl ester 48.1
In analogy to example 19.2, from (3-oxo-cyclopentyl)-(pyridine-2-sulfonyl)-acetic acid methyl ester (example 44.2) and methyliodide was prepared (RS,SR)-2-(3-oxo-cyclopentyl)-2-(pyridine-2-sulfonyl)-propionic acid methyl ester as a white solid, MS: 312 (MH$^+$).
48.2
In analogy to example 19.3, from (RS,SR)-2-(3-oxo-cyclopentyl)-2-(pyridine-2-sulfonyl)-propionic acid methyl ester and (4-chloro-phenyl)-hydrazine hydrochloride was prepared (RS,SR)-2-(7-chloro-1,2,3,4-tetrahydro-cyclopenta[b] indol-2-yl)-2-(pyridine-2-sulfonyl)-propionic acid methyl ester as a white solid, MS: 419 (MH$^+$).

Example 49

(RS,SR)-2-benzenesulfonyl-2-(6-chloro-2,3,4,9-tetrahydro-1H-carbazol-2-yl)-propionic acid To 50 mg (0.115 mmol) of (RS,SR)-2-benzenesulfonyl-2-(6-chloro-2,3,4,9-tetrahydro-1H-carbazol-2-yl)-propionic acid methyl ester (example 3) in 4 mL of THF/MeOH 1:1, 0.29 mL of 2M NaOH (0.58 mmol, 5 eq) were added. The reaction mixture was stirred at 60° C. for 3 hours, acidified to pH=6 with aqueous NH$_4$Cl and extracted with EtOAc. The combined organic phases were dried over Na$_2$SO$_4$, filtered and evaporated. Column chromatography on silica gel with CH$_2$Cl$_2$/MeOH 3:1 yielded 40 mg (82%) of (RS,SR)-2-benzenesulfonyl-2-(6-chloro-2,3,4,9-tetrahydro-1H-carbazol-2-yl)-propionic acid as a white solid, MS: 435 (MNH$_4^+$).

Example 50

(RS,SR)-benzenesulfonyl-(6-chloro-2,3,4,9-tetrahydro-1H-carbazol-2-yl)-fluoro-acetic acid In analogy to example 49, from (RS,SR)-benzenesulfonyl-(6-chloro-2,3,4,9-tetrahydro-1H-carbazol-2-yl)-fluoro-acetic acid methyl ester was prepared (RS,SR)-benzenesulfonyl-(6-chloro-2,3,4,9-tetrahydro-1H-carbazol-2-yl)-fluoro-acetic acid as a white solid, MS: 420 (M–H)$^-$.

Example 51

(RS,SR)-2-(1-benzenesulfonyl-2-methoxy-1-methylethyl)-6-chloro-2,3,4,9-tetrahydro-1H-carbazole 51.1
350 mg (0.81 mmol) of (RS,SR)-2-benzenesulfonyl-2-(6-chloro-2,3,4,9-tetrahydro-1H-carbazol-2-yl)-propionic acid methyl ester (from example 3) in 10 mL of THF at 0° C., were treated with 39 mg (0.89 mmol, 1.1 eq) of NaH (55% in oil) portionwise within 30 min. 0.10 mL (1.22 mmol, 1.5 eq) of 1-chloro-2-methoxy-ethane was added and the ice bath removed. After 2 hours, the reaction was quenched by addition of aqueous NH$_4$Cl sat., extracted with EtOAc and the organic phases dried over Na$_2$SO$_4$. Evaporation of the solvent afforded (RS,SR)-2-benzenesulfonyl-2-(6-chloro-9-methoxymethyl-2,3,4,9-tetrahydro-1H-carbazol-2yl)-propionic acid methyl ester as yellow solid, MS: 493 (MNH$_4$'). The crude material was used in the next step without further purification.
51.2
To 402 mg (0.84 mmol) of (RS,SR)-2-benzenesulfonyl-2-(6-chloro-9-methoxymethyl-2,3,4,9-tetrahydro-1H-carbazol-2yl)-propionic acid methyl ester in 6 mL of THF, 1.0 mL (1.0 mmol, 1.2 eq) of LiAlH$_4$ in THF was added at RT. After 30 min, the reaction mixture was poured into water and extracted with EtOAc, dried over Na$_2$SO4, and evaporation of the solvent afforded (RS,SR)-2-benzenesulfonyl-2-(6-chloro-9-methoxymethyl-2,3,4,9-tetrahydro-1H-carbazol-2-yl)-propan-1-ol as a colorless oil, MS: 465 (MNH$_4^+$). The crude material was used in the next step without further purification.
51.3
130 mg (0.29 mmol) of (RS,SR)-2-benzenesulfonyl-2-(6-chloro-9-methoxymethyl-2,3,4,9-tetrahydro-1H-carbazol-2-yl)-propan-1-ol in 5 mL of THF at 0° C. were treated with 14 mg (0.32 mmol, 1.1 eq) of NaH (55% in oil) portionwise within 30 min. 30 μL (0.43 mmol, 1.5 eq) of MeI were added and the reaction mixture was stirred an additional 2 hours, partitioned between EtOAc and a saturated aqueous solution of NH$_4$Cl. The organic phase was washed with brine, dried over Na$_2$SO$_4$, and evaporated. Column chromatography with heptane/EtOAc 1:2 gave 96 mg (72%) of (RS,SR)-2-(1-benzenesulfonyl-2-methoxy-1-methyl-ethyl)-6-chloro-9-methoxymethyl-2,3,4,9-tetrahydro-1H-carbazole as a white solid, MS: 479 (MNH$_4^+$).
51.4
95 mg (0.20 mmol) of (RS,SR)-2-(1-benzenesulfonyl-2-methoxy-1-methyl-ethyl)-6-chloro-9-methoxymethyl-2,3,4, 9-tetrahydro-1H-carbazole were dissolved in 8 mL of MeOH/THF 1:1, and 5 drops of HCl 12M were added. The temperature was raised to 55° C. and the solution was stirred for 6 hours. By adding 2M NaHCO$_3$ the solution was neutralized to pH=7, and the mixture was extracted with EtOAc. Column chromatography on silica gel with heptane/EtOAc 2:1 yielded 11 mg (13%) of (RS,SR)-2-(1-benzenesulfonyl-2-methoxy-1-methyl-ethyl)-6-chloro-2,3,4,9-tetrahydro-1H-carbazole as a white solid, MS: 418 (MH$^+$).

Example 52

(RS,SR)-2-benzenesulfonyl-2-(6-methyl-2,3,4,9-tetrahydro-1H-carbazol-2-yl)-propionitrile 52.1
To 9.4 g (0.052 mol) of benzenesulfonyl-acetonitrile in 200 mL of DME at −50° C., 7.8 mL (0.052 mol, 1 eq) of TMEDA and 32.4 mL (0.052 mL, 1 eq) of nBuLi (1.6M in hexane) were added and stirring was continued for 45 min. To the resulting white suspension, 4.98 g (0.052 mol, 1 eq) of cyclohex-2-enone were added and the temperature was raised to −10° C. within 4 hours. The reaction mixture was poured into 180 mL of 1M HCl, extracted with EtOAc, and the combined organic phases dried over Na$_2$SO$_4$. Evaporation of the solvent and recrystallisation from AcOEt/Et$_2$O yielded 8.25 g (57%) of benzenesulfonyl-(3-oxo-cyclohexyl)-acetonitrile as a racemic mixture of diastereomers, white crystals, MS: 278 (MH$^+$) (in analogy to: E. Hatzigrigoriou, L. Wartski, Synth. Comm., 1983, 14(4), 319-235).
52.2
4.0 g (0.014 mol) of benzenesulfonyl-(3-oxo-cyclohexyl)-acetonitrile in 40 mL of DMF were treated with 0.69 g (0.016 mol, 1.1 eq) of NaH (55% in oil) portionwise within 30 min at 0° C. 3.07 g (0.022 mol, 1.5 eq) of methyliodide were added, and the ice bath was removed. After 2 hours, the reaction mixture was poured into water and extracted with EtOAc. The combined organic phases were dried over $Na_2SO_4$, filtered and evaporated. Column chromatography over silica gel with AcOEt/heptane 1:1 afforded 4 g (98%) of 2-benzenesulfonyl-2-(3-oxo-cyclohexyl)-propionitrile as a racemic mixture of diastereomers, white solid, MS: 292 ($MH^+$).

52.3

To 322 mg (1.10 mmol) of 2-benzenesulfonyl-2-(3-oxo-cyclohexyl)-propionitrile in 10 mL of glacial acetic acid, 193 mg (1.21 mmol, 1.1 eq) of (4-methyl-phenyl)-hydrazine hydrochloride were added and stirring was continued at RT over night. An aqueous solution of $NaHCO_3$ was added until pH=7, and the product was extracted with EtOAc, the organic phase was dried over $Na_2SO_4$, filtered and evaporated. The resulting two diastereomers were separated by column chromatography on silica gel with AcOEt/heptane 1:4, and triturated with $Et_2O$. 158 mg (38%) of (RR,SS)-2-benzenesulfonyl-2-(6-methyl-2,3,4,9-tetrahydro-1H-carbazol-2-yl)-propionitrile and 123 mg (29%) of (RS,SR)-2-benzenesulfonyl-2-(6-methyl-2,3,4,9-tetrahydro-1H-carbazol-2-yl)-propionitrile were isolated as light yellow solids, MS: 379 ($MH^+$).

Example 53

(RS,SR)-2-benzenesulfonyl-2-(6-chloro-2,3,4,9-tetrahydro-1H-carbazol-2-yl)-propionitrile In analogy to example 53.3, from 2-benzenesulfonyl-2-(3-oxo-cyclohexyl)-propionitrile and (4-chloro-phenyl)-hydrazine hydrochloride was prepared (RR,SS)-2-benzenesulfonyl-2-(6-chloro-2,3,4,9-tetrahydro-1H-carbazol-2-yl)-propionitrile and (RS,SR)-2-benzenesulfonyl-2-(6-chloro-2,3,4,9-tetrahydro-1H-carbazol-2-yl)-propionitrile as a white solid, MS: 397 $(M-H)^-$.

Example 54

(RS,SR)-benzenesulfonyl-(6-chloro-2,3,4,9-tetrahydro-1H-carbazol-2-yl)-fluoro-acetonitrile 54.1

3.85 g (0.014 mol) of benzenesulfonyl-(3-oxo-cyclohexyl)-acetonitrile in 40 mL of DMF were treated with 0.68 g (0.016 mol, 1.1 eq) of NaH (55% in oil) portionwise within 30 min at 0° C. 4.81 g (0.015 mol, 1.1 eq) of N-fluorobenzenesulfonimide were added, and the ice bath was removed. After 2 hours, the reaction mixture was poured into water, extracted with EtOAc. The combined organic phases were dried over $Na_2SO_4$, filtered and evaporated, yielding 4 g of a crude oil, consisting of a mixture of the racemic diastereomer of benzenesulfonyl-fluoro-(3-oxo-cyclohexyl)-acetonitrile, which was used in the next step without further purification.

54.2

In analogy to example 52.3, from benzenesulfonyl-fluoro-(3-oxo-cyclohexyl)-acetonitrile and (4-chloro-phenyl)-hydrazine hydrochloride was prepared (RR,SS)-benzenesulfonyl-(6-chloro-2,3,4,9-tetrahydro-1H-carbazol-2-yl)-fluoro-acetonitrile and (RS,SR)-benzenesulfonyl-(6-chloro-2,3,4,9-tetrahydro-1H-carbazol-2-yl)-fluoro-acetonitrile as a light yellow solid, MS: 402 (M).

Example 55

(RS,SR)-2-benzenesulfonyl-2-(6-chloro-2,3,4,9-tetrahydro-1H-carbazol-2-yl)-2-fluoro-N-methyl-acetamide To 400 mg (0.92 mmol) of (RS,SR)-benzenesulfonyl-(6-chloro-2,3,4,9-tetrahydro-1H-carbazol-2-yl)-fluoro-acetic acid methyl ester (from example 12) in a sealed tube were added 20 mL of methylamine (33% wt. solution in EtOH) and 13 mg (0.27 mmol, 0.3 eq) of sodium cyanide. The reaction mixture was stirred at 90° C. for 2 hours, and the solvent was evaporated. Column chromatography on silica gel with EtOAc yielded 340 mg (86%) of (RS,SR)-2-benzenesulfonyl-2-(6-chloro-2,3,4,9-tetrahydro-1H-carbazol-2-yl)-2-fluoro-N-methyl-acetamide as a white solid, MS: 435 ($MH^+$).

Example 56

(RS,SR)-2-benzenesulfonyl-2-(7-chloro-1,2,3,4-tetrahydro-cyclopenta[b]indol-2-yl)-2-fluoro-N-methyl-acetamide In analogy to example 55, from (RS,SR)-benzenesulfonyl-(7-chloro-1,2,3,4-tetrahydro-cyclopenta[b]indol-2-yl)-fluoro-acetic acid methyl ester (from example 23) was prepared (RS,SR)-2-benzenesulfonyl-2-(7-chloro-1,2,3,4-tetrahydro-cyclopenta[b]indol-2-yl)-2-fluoro-N-methyl-acetamide as a white solid, MS 438 ($MNH_4^+$).

Example 57

(RS,SR)-2-(6-chloro-2,3,4,9-tetrahydro-1H-carbazol-2-yl)-2-fluoro-2-(3-fluoro-benzenesulfonyl)-N-methyl-acetamide In analogy to example 55, from (RS,SR)-(6-chloro-2,3,4,9-tetrahydro-1H-carbazol-2-yl)-fluoro-(3-fluoro-benzenesulfonyl)-acetic acid methyl ester (from example 39) was prepared (RS,SR)-2-(6-chloro-2,3,4,9-tetrahydro-1H-carbazol-2-yl)-2-fluoro-2-(3-fluoro-benzenesulfonyl)-N-methyl-acetamide as a white solid, MS: 470 ($MNH_4^+$).

Example 58

(RS,SR)-2-(7-chloro-1,2,3,4-tetrahydro-cyclopenta[b]indol-2-yl)-2-fluoro-2-(3-fluoro-benzenesulfonyl)-N-methyl-acetamide In analogy to example 55, from (RS,SR)-(7-chloro-1,2,3,4-tetrahydro-cyclopenta[b]indol-2-yl)-fluoro-(3-fluoro-benzenesulfonyl)-acetic acid methyl ester (from example 45) was prepared (RS,SR)-2-(7-chloro-1,2,3,4-tetrahydro-cyclopenta[b]indol-2-yl)-2-fluoro-2-(3-fluoro-benzenesulfonyl)-N-methyl-acetamide as a white solid, MS: 439 ($MH^+$).

Example 59

(RS,SR)-2-benzenesulfonyl-2-(6-chloro-2,3,4,9-tetrahydro-1H-carbazol-2-yl)-2-fluoro-N,N-dimethyl-acetamide 59.1

To 950 mg (2.18 mmol) of (RS,SR)-2-benzenesulfonyl-2-(6-chloro-2,3,4,9-tetrahydro-1H-carbazol-2-yl)-2-fluoro-N-methyl-acetamide (from example 56) in 10 mL of $CH_2Cl_2$ at RT were added 0.60 mL (4.36 mmol, 2 eq) of $Et_3N$, 27 mg (0.22 mmol, 0.1 eq) of DMAP and 571 mg (2.62 mmol, 1.2 eq) of carbonic acid di-tert-butyl ester. The reaction mixture was stirred at RT for 2 hours and extracted with 1M HCl. The organic phases were dried over $Na_2SO_4$, filtered and evaporated. Column chromatography afforded 682 mg (59%) of (RS,SR)-2-(benzenesulfonyl-fluoro-methylcarbamoyl-methyl)-6-chloro-1,2,3,4-tetrahydro-carbazole-9-carboxylic acid tert-butyl ester as white solid, MS: 552 ($MNH_4^+$).

59.2

680 mg (1.27 mmol) of (RS,SR)-2-(benzenesulfonyl-fluoro-methylcarbamoyl-methyl)-6-chloro-1,2,3,4-tetrahydro-carbazole-9-carboxylic acid tert-butyl ester in 10 mL of DMF were treated with 83 mg (1.90 mmol, 1.5 eq) of NaH (55% in oil) portionwise within 30 min at 0° C. 217 mg (1.52 mmol, 1.2 eq) of methyliodide were added and the reaction was stirred an additional 30 min, and then poured into water and extracted with EtOAc. The crude material was dissolved in 10 mL of $CH_2Cl_2$, and 1 mL of TFA was added at RT. Aqueous $Na_2CO_3$ was added until pH=7 was reached, and the organic phases were dried on $Na_2SO_4$, filtered and evaporated. Column chromatography on silica gel with heptane/EtOAc 1:1 yielded 420 mg (65%) of (RS,SR)-2-benzenesulfonyl-2-(6-chloro-2,3,4,9-tetrahydro-1H-carbazol-2-yl)-2-fluoro-N,N-dimethyl-acetamide as a white solid, MS: 449 ($MH^+$).

Example 60

(RS,SR)-2-benzenesulfonyl-2-(7-chloro-1,2,3,4-tetrahydro-cyclopenta[b]indol-2-yl)-2-fluoro-N,N-dimethyl-acetamide In analogy to example 59, from (RS,SR)-2-benzenesulfonyl-2-(7-chloro-1,2,3,4-tetrahydro-cyclopenta[b]indol-2-yl)-2-fluoro-N-methyl-acetamide (from example 57) was prepared (RS,SR)-2-benzenesulfonyl-2-(7-chloro-1,2,3,4-tetrahydro-cyclopenta[b]indol-2-yl)-2-fluoro-N,N-dimethyl-acetamide as a white solid, MS: 452 ($MNH_4^+$).

Example 61

(RS,SR)-2-(6-chloro-2,3,4,9-tetrahydro-1H-carbazol-2-yl)-2-fluoro-2-(3-fluoro-benzenesulfonyl)-N,N-dimethyl-acetamide In analogy to example 59, from (RS,SR)-2-(6-chloro-2,3,4,9-tetrahydro-1H-carbazol-2-yl)-2-fluoro-2-(3-fluoro-benzenesulfonyl)-N-methyl-acetamide (from example 58) was prepared (RS,SR)-2-(6-chloro-2,3,4,9-tetrahydro-1H-carbazol-2-yl)-2-fluoro-2-(3-fluoro-benzenesulfonyl)-N,N-dimethyl-acetamide as a white solid, MS: 467 (MH).

Example 62

(RS,SR)-2-(7-chloro-1,2,3,4-tetrahydro-cyclopenta[b]indol-2-yl)-2-fluoro-2-(3-fluoro-benzenesulfonyl)-N,N-dimethyl-acetamide In analogy to example 59, from (RS,SR)-2-(7-chloro-1,2,3,4-tetrahydro-cyclopenta[b]indol-2-yl)-2-fluoro-(3-fluoro-benzenesulfonyl)-N-methyl-acetamide (from example 58) was prepared (RS,SR)-2-(7-chloro-1,2,3,4-tetrahydro-cyclopenta[b]indol-2-yl)-2-fluoro-2-(3-fluoro-benzenesulfonyl)-N,N-dimethyl-acetamide as a white solid, MS: 453 ($MH^+$).

Example 63

(RS,SR)-2-benzenesulfonyl-N-benzyl-2-(6-chloro-2,3,4,9-tetrahydro-1H-carbazol-2-yl)-2-fluoro-N-methyl-acetamide 60 mg (0.112 mmol) of (RS,SR)-2-(benzenesulfonyl-fluoro-methylcarbamoyl-methyl)-6-chloro-1,2,3,4-tetrahydro-carbazole-9-carboxylic acid tert-butyl ester (from example 59.1) in 3 mL of THF were treated with 7 mg (0.168 mmol, 1.5 eq) of NaH (55% in oil) at 0° C. over 40 min. 38 mg (0.224 mmol, 2eq) of bromomethly-benzene were added and the reaction mixture was stirred over night at RT. The solvent was evaporated, the residue was dissolved in 3 mL of $CH_2Cl_2$, 1 mL of TFA was added, and the reaction mixture was stirred over night at RT. Evaporation of the solvent and purification of the residue by preparative HPLC (C18 column) yielded 35 mg (60%) of (RS,SR)-2-benzenesulfonyl-N-benzyl-2-(6-chloro-2,3,4,9-tetrahydro-1H-carbazol-2-yl)-2-fluoro-N-methyl-acetamide as a white solid, MS: 525 ($MH^+$).

Example 64

(RS,SR)-2-benzenesulfonyl-2-(6-chloro-2,3,4,9-tetrahydro-1H-carbazol-2-yl)-N-(4-cyano-benzyl)-2-fluoro-N-methyl-acetamide In analogy to example 63, from (RS,SR)-2-(benzenesulfonyl-fluoro-methylcarbamoyl-methyl)-6-chloro-1,2,3,4-tetrahydro-carbazole-9-carboxylic acid tert-butyl ester and 4-bromomethyl-benzonitrile was prepared (RS,SR)-2-benzenesulfonyl-2-(6-chloro-2,3,4,9-tetrahydro-1H-carbazol-2-yl)-N-(4-cyano-benzyl)-2-fluoro-N-methyl-acetamide as a white solid, MS: 551 ($MH^+$).

Example 65

(RS,SR)-2-benzenesulfonyl-N-(4-bromo-benzyl)-2-(6-chloro-2,3,4,9-tetrahydro-1H-carbazol-2-yl)-2-fluoro-N-methyl-acetamide In analogy to example 63, from (RS,SR)-2-(benzenesulfonyl-fluoro-methylcarbamoyl-methyl)-6-chloro-1,2,3,4-tetrahydro-carbazole-9-carboxylic acid tert-butyl ester and 1-bromo-4-bromomethyl-benzene was prepared (RS,SR)-2-benzenesulfonyl-N-(4-bromo-benzyl)-2-(6-chloro-2,3,4,9-tetrahydro-1H-carbazol-2-yl)-2-fluoro-N-methyl-acetamide as a white solid, MS: 603;605 ($MH^+$).

Example 66

RS,SR)-2-benzenesulfonyl-2-(6-chloro-2,3,4,9-tetrahydro-1H-carbazol-2-yl)-N-(3,5-difluoro-benzyl)-2-fluoro-N-methyl-acetamide In analogy to example 63, from (RS,SR)-2-(benzenesulfonyl-fluoro-methylcarbamoyl-methyl)-6-chloro-1,2,3,4-tetrahydro-carbazole-9-carboxylic acid tert-butyl ester and 1-bromomethyl-3,5-difluoro-benzene was prepared (RS,SR)-2-benzenesulfonyl-2-(6-chloro-2,3,4,9-tetrahydro-1H-carbazol-2-yl)-N-(3,5-difluoro-benzyl)-2-fluoro-N-methyl-acetamide as a light brown solid, MS: 561 (M).

Example 67

(RS,SR)-4-({[2-benzenesulfonyl-2-(6-chloro-2,3,4,9-tetrahydro-1H-carbazol-2-yl)-2-fluoro-acetyl]-methyl-amino}-methyl)-benzoic acid methyl ester In analogy to example 63, from (RS,SR)-2-(benzenesulfonyl-fluoro-methylcarbamoyl-methyl)-6-chloro-1,2,3,4-tetrahydro-carbazole-9-carboxylic acid tert-butyl ester and 4-bromomethyl-benzoic acid methyl ester was prepared (RS,SR)-4-({[2-benzenesulfonyl-2-(6-chloro-2,3,4,9-tetrahydro-1H-carbazol-2-yl)-2-fluoro-acetyl]-methyl-amino}-methyl)-benzoic acid methyl ester as a light brown solid, MS: 583 (M).

Example 68

(RS,SR)-3-({[2-benzenesulfonyl-2-(6-chloro-2,3,4,9-tetrahydro-1H-carbazol-2-yl)-2-fluoro-acetyl]-methyl-amino}-methyl)-benzoic acid methyl ester In analogy to example 63, from (RS,SR)-2-(benzenesulfonyl-fluoro-methylcarbamoyl-methyl)-6-chloro-1,2,3,4-tetrahydro-carbazole-9-carboxylic acid tert-butyl ester and 3-bromomethyl-benzoic acid methyl ester was prepared (RS,SR)-3-({[2-benzenesulfonyl-2-(6-chloro-2,3,4,9-tetrahydro-1H-carbazol-2-yl)-2-fluoro-acetyl]-methyl-amino}-methyl)-benzoic acid methyl ester as a white solid, MS: 583 (M).

Example 69

(RS,SR)-2-benzenesulfonyl-2-(6-chloro-2,3,4,9-tetrahydro-1H-carbazol-2-yl)-N-(2-cyano-benzyl)-2-fluoro-N-methyl-acetamide In analogy to example 63, from (RS,SR)-2-(benzenesulfonyl-fluoro-methylcarbamoyl-methyl)-6-chloro-1,2,3,4-tetrahydro-carbazole-9-carboxylic acid tert-butyl ester and 2-bromomethyl-benzonitrile was prepared (RS,SR)-2-benzenesulfonyl-2-(6-chloro-2,3,4,9-tetrahydro-1H-carbazol-2-yl)-N-(2-cyano-benzyl)-2-fluoro-N-methyl-acetamide as a white solid, MS: 550 (M).

Example 70

(RS,SR)-N-allyl-2-benzenesulfonyl-2-(6-chloro-2,3,4,9-tetrahydro-1H-carbazol-2-yl)-2-fluoro-N-methyl-acetamide In analogy to example 63, from (RS,SR)-2-(benzenesulfonyl-fluoro-methylcarbamoyl-methyl)-6-chloro-1,2,3,4-tetrahydro-carbazole-9-carboxylic acid tert-butyl ester and 3-bromo-propene was prepared (RS,SR)-N-allyl-2-benzenesulfonyl-2-(6-chloro-2,3,4,9-tetrahydro-1H-carbazol-2-yl)-2-fluoro-N-methyl-acetamide as a white solid, MS: 475 (MH$^+$).

Example 71

(RS,SR)-2-benzenesulfonyl-2-(6-chloro-2,3,4,9-tetrahydro-1H-carbazol-2-yl)-N-(3-cyano-benzyl)-2-fluoro-N-methyl-acetamide In analogy to example 63, from (RS,SR)-2-(benzenesulfonyl-fluoro-methylcarbamoyl-methyl)-6-chloro-1,2,3,4-tetrahydro-carbazole-9-carboxylic acid tert-butyl ester and 3-bromomethyl-benzonitrile was prepared (RS,SR)-2-benzenesulfonyl-2-(6-chloro-2,3,4,9-tetrahydro-1H-carbazol-2-yl)-N-(3-cyano-benzyl)-2-fluoro-N-methyl-acetamide as a white solid, MS: 550 (M).

Example 72

(RS,SR)-3-({[2-benzenesulfonyl-2-(6-chloro-2,3,4,9-tetrahydro-1H-carbazol-2-yl)-2-fluoro-acetyl]-methyl-amino}-methyl)-benzoic acid To 88 mg (0.151 mmol) of (RS,SR)-3{[2-benzenesulfonyl-2-(6-chloro-2,3,4,9-tetrahydro-1H-carbazol-2-yl)-2-fluoro-acetyl]-methyl-amino}-benzoic acid methyl ester (from example 69) in 5 mL of THF/MeOH 1:1, 1 mL of 1M NaOH was added and the reaction mixture was stirred over night at RT. Aqueous NH$_4$Cl was added until pH=7 was reached, the product was extracted with EtOAc, dried over Na$_2$SO$_4$, filtered and solvent evaporated. Recrystallisation in Et$_2$O yielded 66 mg (77%) of (RS,SR)-3-({[2-benzenesulfonyl-2-(6-chloro-2,3,4,9-tetrahydro-1H-carbazol-2-yl)-2-fluoro-acetyl]-methyl-amino}-methyl)-benzoic acid as a white solid, MS: 570 (MH$^+$).

Example 73

(RS,SR)-2-benzenesulfonyl-2-(6-chloro-2,3,4,9-tetrahydro-1H-carbazol-2-yl)-2-fluoro-N-(3-hydroxymethyl-benzyl)-N-methyl-acetamide To 61 mg (0.107 mmol) of (RS,SR)-3-({[2-benzenesulfonyl-2-(6-chloro-2,3,4,9-tetrahydro-1H-carbazol-2-yl)-2-fluoro-acetyl]-methyl-amino}-methyl)-benzoic acid (from example 73) in 3 mL of THF at 0° C., 160 µL (0.107 mmol, 1 eq) of BH$_3$.THF (1M in THF) were added, and the reaction mixture stirred for an additional hour, and then partitioned between EtOAc and water. The organic layer was dried over Na$_2$SO$_4$, filtered and evaporated. Column chromatography on silica gel with EtOAc/heptane 2:1 yielded 50 mg (84%) of (RS,SR)-2-benzenesulfonyl-2-(6-chloro-2,3,4,9-tetrahydro-1H-carbazol-2-yl)-2-fluoro-N-(3-hydroxymethyl-benzyl)-N-methyl-acetamide as a white solid, MS: 555 (M).

Example 74

(RS,SR)-2-[benzenesulfonyl-fluoro-(5-methyl-[1,3,4]oxadiazol-2-yl)-methyl]-7-chloro-1,2,3,4-tetrahydro-cyclopenta[b]indole 74.1
To a stirred solution of 5.0 g (0.023 mol) of benzenesulfonyl-acetic acid methyl ester in 10 mL of MeOH at RT, 3.50 g (0.070 mol, 3 eq) of hydrazine hydrate were added. After one hour, the solvent and the excess of hydrazine were removed under reduced pressure, yielding 4.90 g (quantitative) of benzenesulfonyl-acetic acid hydrazide as a colorless oil, MS: 232 (MNH$_4^+$).

74.2
To a stirred solution of 1.50 g (7.0 mmol) of benzenesulfonyl-acetic acid hydrazide in 5 mL of acetic acid, 1.44 g (14.0 mmol, 2 eq) of acetic anhydride were added, and the solution was heated at reflux for 1 hour. The reaction mixture was diluted with water, extracted with EtOAc, the organic phase dried over Na$_2$SO$_4$, filtered and evaporated, to afford 1.40 g (78%) of acetic acid N'-(2-benzenesulfonyl-acetyl)-hydrazide as a white solid, MS: 274 (MNH$_4^+$).

74.3

To a stirred solution of 1.40 g (5.5 mmol) of acetic acid N'-(2-benzenesulfonyl-acetyl)-hydrazide in 50 mL of acetonitrile, 1.02 g (6.5 mmol, 1.2 eq) of phosphorus oxychloride were added, and the solution heated at reflux for 3 hours. The reaction mixture was diluted with water, extracted with EtOAc, the organic phase dried over $Na_2SO_4$, filtered and evaporated. Column chromatography on silica gel with EtOAc yielded 0.90 g (70%) of 2-benzenesulfonylmethyl-5-methyl-[1,3,4]oxadiazole as a white solid, MS: 239 ($MH^+$).

74.4

To 650 mg (2.73 mmol) of 2-benzenesulfonylmethyl-5-methyl-[1,3,4]oxadiazole in 35 mL of MeOH at 0° C., 50 μL (0.27 mmol, 0.1 eq) of a solution of sodium methoxide (5.4 M in MeOH) were added. After 15 min, 246 mg (3.0 mmol, 1.1 eq) of cyclopent-2-enone were added. The reaction mixture was stirred at 0° C. and was allowed to reach RT within 4 hours, diluted with saturated aqueous $NH_4Cl$ and extracted with EtOAc. The combined organic phases were dried over $Na_2SO_4$, filtered and evaporated. Column chromatography on silica gel with EtOAc gave 750 mg (86%) of 3-[benzenesulfonyl-(5-methyl-[1,3,4]oxadiazol-2-yl)-methyl]-cyclopentanone as a racemic mixture of diastereomers, white solid, MS: 321 ($MH^+$).

74.5

375 mg (1.17 mmol) of 3-[benzenesulfonyl-(5-methyl-[1,3,4]oxadiazol-2-yl)-methyl]-cyclopentanone in 10 mL of DMF, were treated with 52 mg (1.29 mmol, 1.1 eq) of NaH (55% in oil) over 30 min. 554 mg (1.75 mmol, 1.5 eq) of N-fluorobenzenesulfonimide were added, and after 2 hours, the reaction mixture was diluted with saturated aqueous $NH_4Cl$ and extracted with EtOAc. The combined organic phases were dried over $Na_2SO_4$, filtered and evaporated. The resulting two diastereomers were separated by column chromatography on silica gel with EtOAc/heptane 2:1 yielding 80 mg (20%) of (RS,SR)-3-[benzenesulfonyl-fluoro-(5-methyl-[1,3,4]oxadiazol-2-yl)-methyl]-cyclopentanone as a colorless oil, MS: 339 ($MH^+$) and 75 mg (19%) of (RR,SS)-3-[benzenesulfonyl-fluoro-(5-methyl-[1,3,4]oxadiazol-2-yl)-methyl]-cyclopentanone as a white solid, MS: 339 ($MH^+$).

74.6

In analogy to example 23.2, from 80 mg (0.23 mmol) of (RS,SR)-3-[benzenesulfonyl-fluoro-(5-methyl-[1,3,4]oxadiazol-2-yl)-methyl]-cyclopentanone and 49 mg (0.26 mmol, 1.15 eq) of (4-chloro-phenyl)-hydrazine hydrochloride was prepared 38 mg (36%) of (RS,SR)-2-[benzenesulfonyl-fluoro-(5-methyl-[1,3,4]oxadiazol-2-yl)-methyl]-7-chloro-1,2,3,4-tetrahydro-cyclopenta[b]indole as light orange crystals, MS: 446 ($MH^+$).

The enantiomers were separated by preparative chiral HPLC. Column: chiralpak AD, solvent: 20%isopropanol/heptane to give (S)-2-[(R)-Benzenesulfonyl-fluoro-(5-methyl-[1,3,4]oxadiazol-2-yl)-methyl]-7-chloro-1,2,3,4-tetrahydro-cyclopenta[b]indole and (R)-2-[(S)-Benzenesulfonyl-fluoro-(5-methyl-[1,3,4]oxadiazol-2-yl)-methyl]-7-chloro-1,2,3,4-tetrahydro-cyclopenta[b]indole.

Example 75

(RS,SR)-2-[1-benzenesulfonyl-1-(5-methyl-[1,3,4]oxadiazol-2-yl)-ethyl]-7-chloro-1,2,3,4-tetrahydro-cyclopenta[b]indole

75.1

375 mg (1.17 mmol) of 3-[benzenesulfonyl-(5-methyl-[1,3,4]oxadiazol-2-yl)-methyl]-cyclopentanone in 10 mL of DMF, were treated with 52 mg (1.29 mmol, 1.1 eq) of NaH (55% in oil) over 30 min. 300 mg (2.32 mmol, 1.8 eq) of methyliodide were added, and after 2 hours, the reaction mixture was diluted with saturated aqueous $NH_4Cl$ and extracted with EtOAc. The combined organic phases were dried over $Na_2SO_4$, filtered and evaporated. The resulting two diastereomers were separated by column chromatography on silica gel with EtOAc/heptane 1:2, yielding 95 mg (24%) of (RS,SR)-3-[1-benzenesulfonyl-1-(5-methyl-[1,3,4]oxadiazol-2-yl)-ethyl]-cyclopentanone as a white solid, MS: 335 ($MH^+$) and 90 mg (23%) of (RR,SS)-3-[1-benzenesulfonyl-1-(5-methyl-[1,3,4]oxadiazol-2-yl)-ethyl]-cyclopentanone as a white solid, MS: 335 ($MH^+$).

75.2

In analogy to example 19.3, from 90 mg (0.27 mmol) of (RS,SR)-3-[1-benzenesulfonyl-1-(5-methyl-[1,3,4]oxadiazol-2-yl)-ethyl]-cyclopentanone and 58 mg (0.33 mmol, 1.2 eq) of (4-chloro-phenyl)-hydrazine hydrochloride was prepared 35 mg (30%) of (RS,SR)-2-[1-benzenesulfonyl-1-(5-methyl-[1,3,4]oxadiazol-2-yl)-ethyl]-7-chloro-1,2,3,4-tetrahydro-cyclopenta[b]indole as a light yellow solid, MS: 442 ($MH^+$).

Example 76

(RS,SR)-2-(benzenesulfonyl-fluoro-[1,3,4]oxadiazol-2-yl-methyl)-7-chloro-1,2,3,4-tetrahydro-cyclopenta[b]indole

76.1

To 1.73 g (8.07 mmol) of benzenesulfonyl-acetic acid hydrazide were added 20 mL of trimethyl orthoformate and 1.26 g (8.07 mmol, 1 eq) of phosphorous oxychloride. The reaction mixture was stirred one hour at RT, and concentrated under reduced pressure. Column chromatography on silica gel with EtOAc/hexane 2:1 yielded 930 mg (52%) of 2-benzenesulfonylmethyl-[1,3,4]oxadiazole as a white solid, MS: 225 ($MH^+$).

76.2

In analogy to example 74.4, from 2-benzenesulfonylmethyl-[1,3,4]oxadiazole and cyclopent-2-enone was prepared 3-(benzenesulfonyl-[1,3,4]oxadiazol-2-yl-methyl)-cyclopentanone as a racemic mixture of diastereomers. The product was used directly in the next step without further characterisation.

76.3

In analogy to example 74.5, from 3-(benzenesulfonyl-[1,3,4]oxadiazol-2-yl-methyl)-cyclopentanone and N-fluorobenzenesulfonimide were prepared (RS,SR)-3-(benzenesulfonyl-fluoro-[1,3,4]oxadiazol-2-yl)-methyl)-cyclopentanone as a white solid, MS: 342 ($MNH_4^+$) and (RR,SS)-3-(benzenesulfonyl-fluoro-[1,3,4]oxadiazol-2-yl)-methyl)-cyclopentanone as a white solid, MS: 342 ($MNH_4^+$).

76.4

In analogy to example 74.6, from (RS,SR)-3-(benzenesulfonyl-fluoro-[1,3,4]oxadiazol-2-yl)-methyl)-cyclopentanone and (4-chloro-phenyl)-hydrazine hydrochloride was prepared (RS,SR)-2-(benzenesulfonyl-fluoro-[1,3,4]oxadiazol-2-yl-methyl)-7-chloro-1,2,3,4-tetrahydro-cyclopenta[b]indole as light yellow solid, MS: 449 ($MNH_4^+$).

Example 77

(RS,SR)-2-[benzenesulfonyl-(5-cyclopropyl-[1,3,4]
oxadiazol-2-yl)-fluoro-methyl]-7-chloro-1,2,3,4-
tetrahydro-cyclopenta[b]indole 77.1

To 3.0 g (14.0 mmol) of benzenesulfonyl-acetic acid hydrazide in 30 mL of phosphorus oxychloride, 1.47 g (17.0 mmol, 1.2 eq) of cyclopropanecarboxylic acid were added, and heated at reflux for 2 hours. The reaction mixture was very carefully poured onto ice, extracted with EtOAc, filtered and evaporated. Column chromatography on silica gel with EtOAc/heptane 2:1 yielded 1.49g (41%) of 2-benzenesulfonylmethyl-5-cyclopropyl-[1,3,4]oxadiazole as a white solid, MS: 265 (MH$^+$).

77.2

In analogy to example 74.4, from 2-benzenesulfonylmethyl-5-cyclopropyl-[1,3,4]oxadiazole and cyclopent-2-enone was prepared 3-[benzenesulfonyl-(5-cyclopropyl-[1,3,4]oxadiazol-2-yl)-methyl]-cyclopentanone as a racemic mixture of diastereomers, white solid, MS: 347 (MH$^+$).

77.3

In analogy to example 74.5, from 3-[benzenesulfonyl-(5-cyclopropyl-[1,3,4]oxadiazol-2-yl)-methyl]-cyclopentanone and N-fluorobenzenesulfonimide were prepared (RS,SR)-3-[benzenesulfonyl-(5-cyclopropyl-[1,3,4]oxadiazol-2-yl)-fluoro-methyl]-cyclopentanone as a white solid, MS: 365 (MH$^+$) and (RR,SS)-3-[benzenesulfonyl-(5-cyclopropyl-[1,3,4]oxadiazol-2-yl)-fluoro-methyl]-cyclopentanone as a white solid, MS: 365 (MH$^+$).

77.4

In analogy to example 74.6, from (RS,SR)-3-[benzenesulfonyl-(5-cyclopropyl-[1,3,4]oxadiazol-2-yl)-fluoro-methyl]-cyclopentanone and (4-chloro-phenyl)-hydrazine hydrochloride was prepared (RS,SR)-2-[benzenesulfonyl-(5-cyclopropyl-[1,3,4]oxadiazol-2-yl)-fluoro-methyl]-7-chloro-1,2,3,4-tetrahydro-cyclopenta[b]indole as light brown solid, MS: 472 (MH$^+$).

Example 78

(RS,SR)-2-[benzenesulfonyl-(5-cyclopropyl-[1,3,4]
oxadiazol-2-yl)-fluoro-methyl]-6-chloro-2,3,4,9-
tetrahydro-1H-carbazole 78.1

To 2.47 g (9.3 mmol) of 2-benzenesulfonylmethyl-5-cyclopropyl-[1,3,4]oxadiazole in 25 mL of MeOH at 0° C., 170 μL (0.93 mmol, 0.1 eq) of a solution of sodium methoxyde (5.4 M in MeOH) were added. After 15 min, 895 mg (9.3 mmol, 1 eq) of cyclohex-2-enone were added. The reaction mixture was stirred from 0° C. to RT over 4 hours, diluted with saturated aqueous NH$_4$Cl and extracted with EtOAc. The combined organic phases were dried over Na$_2$SO$_4$, filtered and evaporated. Column chromatography on silica gel with EtOAc/heptane 2:1 gave 1.48 g (44%) of 3-[benzenesulfonyl-(5-cyclopropyl-[1,3,4]oxadiazol-2-yl)-methyl]-cyclohexanone as a racemic mixture of diastereomers, white solid, MS: 361 (MH$^+$).

78.2

In analogy to example 74.5, from 3-[benzenesulfonyl-(5-cyclopropyl-[1,3,4]oxadiazol-2-yl)-methyl]-cyclohexanone and N-fluorobenzenesulfonimide were prepared (RS,SR)-3-[benzenesulfonyl-(5-cyclopropyl-[1,3,4]oxadiazol-2-yl)-fluoro-methyl]-cyclohexanone as a white solid, MS: 379 (MH$^+$) and (RR,SS)-3-[benzenesulfonyl-(5-cyclopropyl-[1,3,4]oxadiazol-2-yl)-fluoro-methyl]-cyclohexanone as a white solid, MS: 379 (MH$^+$).

78.3

In analogy to example 12.2, from (RS,SR)-3-[benzenesulfonyl-(5-cyclopropyl-[1,3,4]oxadiazol-2-yl)-fluoro-methyl]-cyclohexanone and (4-chloro-phenyl)-hydrazine hydrochloride was prepared (RS,SR)-2-[benzenesulfonyl-(5-cyclopropyl-[1,3,4]oxadiazol-2-yl)-fluoro-methyl]-6-chloro-2,3,4,9-tetrahydro-1H-carbazole as a yellow solid, MS: 486 (MH$^+$).

Example 79

(RS,SR)-{15-[benzenesulfonyl-(7-chloro-1,2,3,4-
tetrahydro-cyclopenta[b]indol-2-yl)-fluoro-methyl]-
[1,3,4]oxadiazol-2-yl}-dimethyl-amine 79.1

To 3.0 g (14.0 mmol) of benzenesulfonyl-acetic acid hydrazide in 100 mL of CHCl$_3$, 3.41 g (21.0 mmol, 1.5 eq) of dichloromethylene-dimethyl-ammonium chloride and 3.90 mL (28.0 mmol, 2 eq) of triethyl-amine were added. The solution was stirred at reflux for 1 hour, partitioned between aqueous NaOH 0.5M and EtOAc. The combined organic phases were dried over Na$_2$SO$_4$, filtered, evaporated, and column chromatography on silica gel with CH$_2$Cl$_2$/MeOH 100:1 afforded 0.59 g /15%) of (5-benzenesulfonylmethyl-[1,3,4]oxadiazol-2-yl)-dimethyl-amine as a white solid, MS: 268 (MH$^+$).

79.2

In analogy to example 74.4, from (5-benzenesulfonylmethyl-[1,3,4]oxadiazol-2-yl)-dimethyl-amine and cyclopent-2-enone was prepared 3-[benzenesulfonyl-(5-dimethylamino-[1,3,4]oxadiazol-2-yl)-methyl]-cyclopentanone as a racemic mixture of diastereomers, light yellow solid, MS: 350 (MH$^+$).

79.3

In analogy to example 74.5, from 3-[benzenesulfonyl-(5-dimethylamino-[1,3,4]oxadiazol-2-yl)-methyl]-cyclopentanone and N-fluorobenzenesulfonimide were prepared (RS,SR)-3-[benzenesulfonyl-(5-dimethylamino-[1,3,4]oxadiazol-2-yl)-fluoro-methyl]-cyclopentanone as a white solid, MS: 368 (MH$^+$) and (RR,SS)-3-[benzenesulfonyl-(5-dimethylamino-[1,3,4]oxadiazol-2-yl)-fluoro-methyl]-cyclopentanone as a white solid, MS: 368 (MH$^+$).

79.4

In analogy to example 74.6, from (RS,SR)-3-[benzenesulfonyl-(5-dimethylamino-[1,3,4]oxadiazol-2-yl)-fluoro-methyl]-cyclopentanone and (4-chloro-phenyl)-hydrazine hydrochloride was prepared (RS,SR)-{5-[benzenesulfonyl-(7-chloro-1,2,3,4-tetrahydro-cyclopenta[b]indol-2-yl)-fluoro-methyl]-[1,3,4]oxadiazol-2-yl}-dimethyl-amine as a white solid, MS: 475 (MH$^+$).

Example 80

(RS,SR)-{5-[benzenesulfonyl-(7-chloro-1,2,3,4-
tetrahydro-cyclopenta[b]indol-2-yl)-fluoro-methyl]-
[1,3,4]oxadiazol-2-yl}-dimethyl-amine; HCl salt To 15 mg (0.031 mmol) of (RS,SR)-{5-[benzenesulfonyl-(7-chloro-1,2,3,4-tetrahydro-cyclopenta[b]indol-2-yl)-fluoro-methyl]-[1,3,4]oxadiazol-2-yl}-dimethylamine in 5 mL of Et$_2$O/EtOAc 3:1, HCl gas was bubbled into the solution until a white precipitate was formed. The solvent was removed, and the solid dried under vacuo, yielded 14 mg (87%) of (RS,SR)-{5-[benzenesulfonyl-(7-chloro-1,2,3,4-tetrahydro-cyclopenta[b]indol-2-yl)-fluoro-methyl]-[1,3,4]oxadiazol-2-yl}-dimethyl-amine; HCl salt as a white solid, MS: 475 (MH$^+$).

Example 81

(RS,SR)-2-[benzenesulfonyl-fluoro-(3-methyl-[1,2,4]oxadiazol-5-yl)-methyl]-7-chloro-1,2,3,4-tetrahydro-cyclopenta[b]indole 81.1

10.8 g (0.098 mol) of benzenethiol in 70 mL of DMF at 0° C., were treated with 4.31 g (0.108 mol, 1.1 eq) of NaH (55% in oil) over 40 min. 17.19 g (0.103 mol, 1.05 eq) of bromoacetic acid ethyl ester were added, and stirring was continued over night. The reaction mixture was partitioned between aqueous NH$_4$Cl and EtOAc, dried over Na$_2$SO$_4$, filtered and evaporated, to afford 15.4 g (80%) of phenylsulfanyl-acetic acid ethyl ester as a colorless oil, MS: 197 (MH$^+$).

81.2

565 mg (7.65 mmol, 1.5 eq) of N-hydroxy-acetamidine in 50 ml of THF were treated at RT with 306 mg (7.65 mmol, 1.5 eq) of NaH portionwise within 30 min. 1.0 g (5.1 mmol) of phenylsulfanyl-acetic acid ethyl ester was added in a THF solution, and stirring was continued for 1 hour at 60° C. The reaction mixture was diluted with saturated aqueous NH$_4$Cl, extracted with EtOAc, filtered and evaporated. Column chromatography on silica gel with EtOAc/heptane 1:1 yielded 480 mg (46%) of 3-methyl-5-phenylsulfanylmethyl-[1,2,4]oxadiazole as a colorless oil.

81.3

To 450 mg (2.2 mmol) of 3-methyl-5-phenylsulfanylmethyl-[1,2,4]oxadiazole in 50 mL of CHCl$_3$ at RT, 1.08 g (4.4 mmol, 2 eq) of mCPBA were added, and stirred 2 hours. The reaction mixture was washed with an aqueous solution of NaHCO$_3$ and the organic phase dried over Na$_2$SO$_4$, filtered and evaporated. Column chromatography on silica gel with EtOAc/heptane 1:1 afforded 385 mg (74%) of 5-benzenesulfonylmethyl-3-methyl-[1,2,4]oxadiazole as a white solid, MS: 239 (MH$^+$).

81.4

In analogy to example 74.4, from 5-benzenesulfonylmethyl-3-methyl-[1,2,4]oxadiazole and cyclopent-2-enone was prepared 3-[benzenesulfonyl-(3-methyl-[1,2,4]oxadiazol-5-yl)-methyl]-cyclopentanone as a racemic mixture of diastereomers, white solid, MS: 321 (MH$^+$).

81.5

In analogy to example 74.5, from 3-[benzenesulfonyl-(3-methyl-[1,2,4]oxadiazol-5-yl)-methyl]-cyclopentanone and N-fluorobenzenesulfonimide were prepared (RS,SR)-3-[benzenesulfonyl-fluoro-(3-methyl-[1,2,4]oxadiazol-5-yl)-methyl]-cyclopentanone as a white solid, MS: 339 (MH$^+$) and (RR,SS)-3-[benzenesulfonyl-fluoro-(3-methyl-[1,2,4]oxadiazol-5-yl)-methyl]-cyclopentanone as a white solid, MS: 339 (MH$^+$).

81.6

In analogy to example 74.6, from (RS,SR)-3-[benzenesulfonyl-fluoro-(3-methyl-[1,2,4]oxadiazol-5-yl)-methyl]-cyclopentanone and (4-chloro-phenyl)-hydrazine hydrochloride was prepared (RS,SR)-2-[benzenesulfonyl-fluoro-(3-methyl-[1,2,4]oxadiazol-5-yl)-methyl]-7-chloro-1,2,3,4-tetrahydro-cyclopenta[b]indole as a light brown solid, MS: 446 (MH$^+$).

Example 82

(RS,SR)-5-[benzenesulfonyl-(7-chloro-1,2,3,4-tetrahydro-cyclopenta[b]indol-2-yl)-fluoro-methyl]-[1,2,4]oxadiazole-3-carboxylic acid methyl ester 82.1

To a stirred suspension of 10.0 g (0.117 mol) of nitriloacetic acid methyl ester and 8.17 g of (0.117 mol, 1 eq) of hydroxylamine.hydrochloride in 250 mL of MeOH at RT, 21.8 mL (0.117 mol, 1 eq) of a solution of sodium methoxide (5.4 M in MeOH) were added. Stirring was continued for 3 hours, and the reaction was filtered and concentrated under vacuum. The resulting yellow gum was extracted several times with CH$_2$Cl$_2$, and the organic phase filtrated over decalite, and evaporated, to afford 1.1 g (8%) of amino-hydroxyimino-acetic acid methyl ester as a white solid.

82.2

300 mg (2.54 mmol) of amino-hydroxyimino-acetic acid methyl ester and 428 mg (2.29 mmol, 0.9 eq) of phenylsulfanyl-acetyl chloride were stirred in 10 mL of THF at RT for 1 hour. The solvent was evaporated, the residue dissolved in dioxane, and the reaction mixture was heated at reflux over night in the presence of molecular sieves. Filtration, concentration under vacuum and column chromatography over silica gel with EtOAc/heptane 1:1 yielded 310 mg (49%) of 5-phenylsulfanylmethyl-[1,2,4]oxadiazole-3-carboxylic acid methyl ester as light yellow oil, MS: 268 (MNH$_4^+$).

82.3

In analogy to example 81.3, from 5-phenylsulfanylmethyl-[1,2,4]oxadiazole-3-carboxylic acid methyl ester was prepared 5-benzenesulfonylmethyl-[1,2,4]oxadiazole-3-carboxylic acid methyl ester as a white solid, MS: 283 (MH$^+$).

82.4

In analogy to example 74.4, from 5-benzenesulfonylmethyl-[1,2,4]oxadiazole-3-carboxylic acid methyl ester and cyclopent-2-enone was prepared 5-[benzenesulfonyl-(3-oxo-cyclopentyl)-methyl]-[1,2,4]oxadiazole-3-carboxylic acid methyl ester as a racemic mixture of diastereomers, colorless oil, MS: 382 (MNH$_4^+$).

82.5

In analogy to example 74.5, from 5-[benzenesulfonyl-(3-oxo-cyclopentyl)-methyl]-[1,2,4]oxadiazole-3-carboxylic acid methyl ester and N-fluorobenzenesulfonimide were prepared (RS,SR)-5-[benzenesulfonyl-fluoro-(3-oxo-cyclopentyl)-methyl]-[1,2,4]oxadiazole-3-carboxylic acid methyl ester as a white solid, MS: 400 (MNH$_4^+$) and (RR,SS)-5-[benzenesulfonyl-fluoro-(3-oxo-cyclopentyl)-methyl]-[1,2,4]oxadiazole-3-carboxylic acid methyl ester as a white solid, MS: 400 (MNH$_4^+$).

82.6

In analogy to example 74.6, from (RS,SR)-5-[benzenesulfonyl-fluoro-(3-oxo-cyclopentyl)-methyl]-[1,2,4]oxadiazole-3-carboxylic acid methyl ester and (4-chloro-phenyl)-hydrazine hydrochloride was prepared (RS,SR)-5-[benzenesulfonyl-(7-chloro-1,2,3,4-tetrahydro-cyclopenta[b]indol-2-yl)-fluoro-methyl]-[1,2,4]oxadiazole-3-carboxylic acid methyl ester as a light orange solid, MS: 490 (MH$^+$).

Example 83

(RS,SR)-{5-[benzenesulfonyl-(7-chloro-1,2,3,4-tetrahydro-cyclopenta[b]indol-2-yl)-fluoro-methyl]-[1,2,4]oxadiazol-3-yl}-methanol To a stirred solution of 80 mg (0.16 mmol) of (RS,SR)-5-[benzenesulfonyl-(7-chloro-1,2,3,4-tetrahydro-cyclopenta

[b]indol-2-yl)-fluoro-methyl]-[1,2,4]oxadiazole-3-carboxylic acid methyl ester (from example 83) in 10 mL of THF at RT, 180 μL (0.17 mmol, 1.1 eq) of LiAlH$_4$ (1M in THF) were added. After 1 hour, the reaction mixture was partitioned between aqueous NH$_4$Cl and EtOAc. The organic phase was dried over Na$_2$SO$_4$, filtered and evaporated. Column chromatography on silica gel with EtOAc/heptane 1:1 gave 19 mg (25%) of (RS,SR)-{5-[benzenesulfonyl-(7-chloro-1,2,3,4-tetrahydro-cyclopenta[b]indol-2-yl-fluoro-methyl]-[1,2,4]oxadiazol-3-yl}-methanol as a light yellow solid, MS: 462 (MH$^+$).

Example 84

(RS,SR)-5-[benzenesulfonyl-(7-chloro-1,2,3,4-tetrahydro-cyclopenta[b]indol-2-yl)-fluoro-methyl]-[1,2,4]oxadiazole-3-carboxylic acid To a stirred solution of 600 mg (1.22 mmol) of (RS,SR)-5-[benzenesulfonyl-(7-chloro-1,2,3,4-tetrahydro-cyclopenta[b]indol-2-yl)-fluoro-methyl]-[1,2,4]oxadiazole-3-carboxylic acid methyl ester in 5 mL of MeOH/THF 1:1, were added 980 mg (24.5 mmol, 20 eq) of NaOH in solution in 3 mL of water. After 2 hours at RT, aqueous NH$_4$Cl was added until pH=7 was reached, the product was extracted with EtOAc, dried over Na$_2$SO$_4$, filtered and solvent evaporated. Column chromatography on silica gel with CH$_2$Cl$_2$/MeOH 8:2 yielded 300 mg (52%) of (RS,SR)-5-[benzenesulfonyl-(7-chloro-1,2,3,4-tetrahydro-cyclopenta[b ]indol-2-yl)-fluoro-methyl]-[1,2,4]oxadiazole-3-carboxylic acid as a white solid, MS: 430 (M-COOH).

Example 85

(RS,SR)-5-[benzenesulfonyl-(7-chloro-1,2,3,4-tetrahydro-cyclopenta[b]indol-2-yl)-fluoro-methyl]-[1,2,4]oxadiazole-3-carboxylic acid amide To a stirred solution of 70 mg (0.14 mmol) of (RS,SR)-5-[benzenesulfonyl-(7-chloro-1,2,3,4-tetrahydro-cyclopenta[b]indol-2-yl)-fluoro-methyl]-[1,2,4]oxadiazole-3-carboxylic acid methyl ester in 3 mL of EtOH, were added 0.5 mL of an ammonium hydroxide solution (25% in water) and stirred over night. The reaction mixture was partitioned between EtOAc and water. The organic phase was dried over Na$_2$SO$_4$, filtered and evaporated. Recrystallisation in Et$_2$O afforded 60 mg (86%) of (RS,SR)-5-[benzenesulfonyl-(7-chloro-1,2,3,4-tetrahydro-cyclopenta[b]indol-2-yl)-fluoro-methyl]-[1,2,4]oxadiazole-3-carboxylic acid amide as a light orange crystals, MS: 475 (MH$^+$).

Example 86

(RS,SR)-{5-[benzenesulfonyl-(7-chloro-1,2,3,4-tetrahydro-cyclopenta[b]indol-2-yl)-fluoro-methyl]-[1,2,4]oxadiazol-3-yl}-dimethyl-amine 86.1
In analogy to example 82.1, from dimethyl-cyanamide and hydroxylamine hydrochloride was prepared amino-hydroxyimino-dimethyl amine as a light orange solid and used directly in the next step without purification and characterisation. In analogy to example 82.2, from this derivative and phenylsulfanyl-acetic acid ethyl ester was prepared dimethyl-(5-phenylsulfanylmethyl-[1,2,4]oxadiazol-3-yl)-amine as a colorless oil, MS: 236 (MH$^+$).

86.2
In analogy to example 81.3, from dimethyl-(5-phenylsulfanylmethyl-[1,2,4]oxadiazol-3-yl)-amine and mCPBA was prepared (5-benzenesulfonylmethyl-[1,2,4]oxadiazol-3-yl)-dimethyl-amine as a white solid, MS: 268 (MH$^+$).

86.3
In analogy to example 74.4, from (5-benzenesulfonylmethyl-[1,2,4]oxadiazol-3-yl)-dimethyl-amine and cyclopent-2-enone was prepared 3-[benzenesulfonyl-(3-dimethylamino-[1,2,4]oxadiazol-5-yl)-methyl]-cyclopentanone as a racemic mixture of diastereomers, yellow solid, MS: 350 (MH$^+$).

86.4
In analogy to example 74.5, from 3-[benzenesulfonyl-(3-dimethylamino-[1,2,4]oxadiazol-5-yl)-methyl]-cyclopentanone and N-fluorobenzenesulfonimide were prepared (RS,SR)-3-[benzenesulfonyl-(3-dimethylamino-[1,2,4]oxadiazol-5-yl)-fluoro-methyl]-cyclopentanone as a white solid, MS: 368 (MH$^+$) and (RR,SS)-3-[benzenesulfonyl-(3-dimethylamino-[1,2,4]oxadiazol-5-yl)-fluoro-methyl]-cyclopentanone as a white solid, MS: 368 (MH$^+$).

86.5
In analogy to example 74.6, from (RS,SR)-3-[benzenesulfonyl-(3-dimethylamino-[1,2,4]oxadiazol-5-yl)-fluoro-methyl]-cyclopentanone and (4-chloro-phenyl)-hydrazine hydrochloride was prepared (RS,SR)-{5-[benzenesulfonyl-(7-chloro-1,2,3,4-tetrahydro-cyclopenta[b]indol-2-yl)-fluoro-methyl]-[1,2,4]oxadiazol-3-yl}-dimethyl-amine as a white solid, MS: 475 (MH$^+$).

Example 87

(RS,SR)-7-chloro-2-[(3-chloro-benzene sulfonyl)-fluoro-(3-methyl-[1,2,4]oxadiazol-5-yl)-methyl]-1,2,3,4-tetrahydro-cyclopenta[b]indole 87.1
In analogy to example 81.1, 4.34 g (0.030 mol) of 3-chloro-benzenethiol in 50 mL of DMF at 0° C. were treated with 1.32 g (0.033 mol, 1.1 eq) of NaH (55% in oil) over 45 min. 4.82 g (0.032 g, 1.05 eq) of bromo-acetic acid ethyl ester were added, and stirring was continued for 2 hours. Workup and purification gave 5.9 g (91%) of (3-chloro-phenylsulfanyl)-acetic acid methyl ester as a colorless oil.

87.2
In analogy to example 81, from (3-chloro-phenylsulfanyl)-acetic acid methyl ester and N-hydroxy-acetamidine was prepared 5-(3-chloro-phenylsulfanylmethyl)-3-methyl-[1,2,4]oxadiazole as a colorless oil, MS: 241 (MH$^+$).

87.3
In analogy to example 81.3, from 5-(3-chloro-phenylsulfanylmethyl)-3-methyl-[1,2,4]oxadiazole and mCPBA was prepared 5-(3-chloro-benzenesulfonylmethyl)-3-methyl-[1,2,4]oxadiazole as a white solid, MS: 273 (MH$^+$).

87.4
In analogy to example 81.4, from 5-(3-chloro-benzenesulfonylmethyl)-3-methyl-[1,2,4]oxadiazole and cyclopent-2-enone was prepared 3-[(3-chloro-benzenesulfonyl)-(3-methyl-[1,2,4]oxadiazol-5-yl)-methyl]-cyclopentanone as a racemic mixture of diastereomers, light yellow oil, MS: 355 (MH+).

87.5
In analogy to example 81.5, from 3-[(3-chloro-benzenesulfonyl)-(3-methyl-[1,2,4]oxadiazol-5-yl)-methyl]-cyclopentanone and N-fluorobenzenesulfonimide were prepared (RS,SR)-3-[(3-chloro-benzenesulfonyl)-fluoro-(3-methyl-[1,2,4]oxadiazol-5-yl)-methyl]-cyclopentanone as a white solid and (RR,SS)-3-[(3-chloro-benzenesulfonyl)-fluoro-(3-methyl-[1,2,4]oxadiazol-5-yl)-methyl]-cyclopentanone as a white solid.

87.6

In analogy to example 81.6, from (RS,SR)-3-[(3-chloro-benzenesulfonyl)-fluoro-(3-methyl-[1,2,4]oxadiazol-5-yl)-methyl]-cyclopentanone and (4-chloro-phenyl)-hydrazine hydrochloride was prepared (RS,SR)-7-chloro-2-[(3-chloro-benzenesulfonyl)-fluoro-(3-methyl-[1,2,4]oxadiazol-5-yl)-methyl]-1,2,3,4-tetrahydro-cyclopenta[b]indole as a white solid, MS: 480 (MH$^+$).

Example 88

(RS,SR)-7-chloro-2-[(3-chloro-benzenesulfonyl)-fluoro-(5-methyl-[1,3,4]oxadiazol-2-yl)-methyl]-1,2,3,4-tetrahydro-cyclopenta[b]indole 88.1

In analogy to example 81.3, from (3-chloro-phenylsulfanyl)-acetic acid methyl ester and mCPBA was prepared (3-chloro-phenylsulfonyl)-acetic acid methyl ester as a colorless oil, MS: 256 (MNH$_4^+$).

88.2

In analogy to example 74.1, from (3-chloro-phenylsulfonyl)-acetic acid methyl ester and hydrazine hydrate was prepared (3-chloro-phenylsulfonyl)-acetic acid hydrazide as a white solid, MS: 249 (MH$^+$).

88.3

In analogy to example 74.2, from (3-chloro-phenylsulfonyl)-acetic acid hydrazide and acetic anhydride was prepared acetic acid N'-(2-benzenesulfonyl-acetyl)-hydrazide as a white solid, MS: 291 (MH$^+$).

88.4

In analogy to example 74.3, from acetic acid N'-(2-benzenesulfonyl-acetyl)-hydrazide and phosphorus oxychloride was prepared 2-(3-chloro-benzenesulfonylmethyl)-5-methyl-[1,3,4]oxadiazole as viscous oil, MS: 273 (MH$^+$).

88.5

In analogy to example 74.4, from 2-(3-chloro-benzenesulfonylmethyl)-5-methyl-[1,3,4]oxadiazole and cyclopent-2-enone was prepared 3-[(3-chloro-benzenesulfonyl)-(5-methyl-[1,3,4]oxadiazol-2-yl)-methyl]-cyclopentanone as a racemic mixture of diastereomers, white solid, MS: 355 (MH$^+$).

88.6

In analogy to example 74.5, from 3-[(3-chloro-benzenesulfonyl)-(5-methyl-[1,3,4]oxadiazol-2-yl)-methyl]-cyclopentanone and N-fluorobenzenesulfonimide were prepared (RS,SR)-3-[(3-chloro-benzenesulfonyl)-fluoro-(5-methyl-[1,3,4]oxadiazol-2-yl)-methyl]-cyclopentanone as a white solid, MS: 373 (MH$^+$) and (RR,SS)-3-[(3-chloro-benzenesulfonyl)-fluoro-(5-methyl-[1,3,4]oxadiazol-2-yl)-methyl]-cyclopentanone as a white solid, MS: 373 (MH$^+$).

88.7

In analogy to example 74.6, from (RS,SR)-3-[(3-chloro-benzenesulfonyl)-fluoro-(5-methyl-[1,3,4]oxadiazol-2-yl)-methyl]-cyclopentanone and (4-chloro-phenyl)-hydrazine hydrochloride was prepared (RS,SR)-7-chloro-2-[(3-chloro-benzenesulfonyl)-fluoro-(5-methyl-[1,3,4]oxadiazol-2-yl)-methyl]-1,2,3,4-tetrahydro-cyclopenta[D]indole as a light brown solid, MS: 480 (MH$^+$).

Example 89

(RS,SR)-2-{5-[benzenesulfonyl-(7-chloro-1,2,3,4-tetrahydro-cyclopenta[b]indol-2-yl)-fluoro-methyl]-[1,2,4]oxadiazol-3-ylmethyl}-isoindole-1,3-dione 89.1

32 g (0.217 mol) of isoindole-1,3-dione in 160 mL of DMF were treated with 11.75 g (0.294 mol, 1.35 eq) of NaH (60% in oil) over 45 min at 0° C. 22.17 g (0.294 mol, 1.35 eq) of chloro-acetonitrile were added, and the reaction was stirred over night. The reaction mixture was poured into 1.5 L of water, and the precipitate was collected by filtration, washed with Et$_2$O and dried under high vacuum to afford 36.1 g (89%) of (1,3-dioxo-1,3-dihydro-isoindol-2-yl)-acetonitrile as a white solid, MS: 187 (MH$^+$).

89.2

To a mixture of 35.4 g (0.190 mol) of (1,3-dioxo-1,3-dihydro-isoindol-2-yl)-acetonitrile and 14.78 g (0.213 mol, 1.12 eq) of hydroxylamine hydrochloride in 100 mL of DMF, were added 38.7 mL (0.209 mol, 1.1 eq) of a solution of sodium methoxide (5.4 M in MeOH) dropwise at RT. After 2 hours, the reaction mixture was poured into 1 L of cold water, and the precipitate was collected by filtration and dried under high vacuum. This gave 37.7 g (90%) of 2-(1,3-dioxo-1,3-dihydro-isoindol-2-yl)-N-hydroxy-acetamidine as a white solid, MS: 220 (MH$^+$).

89.3

To 10 g (0.046 mol) of 2-(1,3-dioxo-1,3-dihydro-isoindol-2-yl)-N-hydroxy-acetamidine dissolved in 500 mL of DMF, 1.84 g (0.046 mol, 1 eq) of magnesium oxide were added. After 15 min, 8.5 g (0.046 mol, 1 eq) of phenylsulfanyl-acetyl chloride were added, and the temperature was raised to 105° C. and the solution was stirred overnight. The reaction mixture was partitioned between aqueous NH$_4$Cl and EtOAc, dried over Na$_2$SO$_4$. Column chromatography on silica gel with EtOAc/Heptane 1:1 yielded 8.7 g (55%) of 2-(5-phenylsulfanylmethyl-[1,2,4]oxadiazol-3-ylmethyl)-isoindole-1,3-dione as a light yellow solid, MS: 352 (MH$^+$).

89.4

In analogy to example 81.3, from 2-(5-phenylsulfanylmethyl-[1,2,4]oxadiazol-3-ylmethyl)-isoindole-1,3-dione was prepared 2-(5-benzenesulfonylmethyl-[1,2,4]oxadiazol-3-ylmethyl)-isoindole-1,3-dione as a white solid, MS: 384 (MH$^+$).

89.5

In analogy to example 74.4, from 2-(5-benzenesulfonylmethyl-[1,2,4]oxadiazol-3-ylmethyl)-isoindole-1,3-dione and cyclopent-2-enone was prepared 2-{5-[benzenesulfonyl-(3-oxo-cyclopentyl)-methyl]-[1,2,4]oxadiazol-3-ylmethyl}-isoindole-1,3-dione as a racemic mixture of diastereomers, white solid, MS: 452 (MH$^+$).

89.6

In analogy to example 74.5, from 2-{5-[benzenesulfonyl-(3-oxo-cyclopentyl)-methyl]-[1,2,4]oxadiazol-3-ylmethyl}-isoindole-1,3-dione and N-fluorobenzenesulfonimide was prepared 2-{5-[benzenesulfonyl-fluoro-(3-oxo-cyclopentyl)-methyl]-[1,2,4]oxadiazol-3-ylmethyl}-isoindole-1,3-dione as a racemic mixture of diastereomers, white solid, MS: 484 (MH$^+$).

89.7

To 1.90 g (3.92 mmol) of 2-{5-[benzenesulfonyl-fluoro-(3-oxo-cyclopentyl)-methyl]-[1,2,4]oxadiazol-3-ylmethyl}-isoindole-1,3-dione (as mixture of diastereomers) in 50 mL of glacial acetic acid, 870 mg (4.70 mmol, 1.2 eq) of (4-chloro-phenyl)-hydrazine hydrochloride were added. The reaction mixture was heated from 50 to 75° C. over 2 hours. The solvent was removed under vacuum, and an aqueous solution of NaHCO3 was added until ph=7, and the product was extracted with EtOAc. The combined organic phases were dried over $Na_2SO_4$, filtered and evaporated. A column chromatography on silica gel with EtOAc/Heptane 1:2 yielded 530 mg (23%) of (RR,SS)-2-{5-[benzenesulfonyl-(7-chloro-1,2,3,4-tetrahydro-cyclopenta[b]indol-2-yl)-fluoro-methyl]-[1,2,4]oxadiazol-3-ylmethyl}-isoindole-1,3-dione as a light yellow solid, MS: 608 ($MNH_4^+$), and 417 mg (18%) of (RS,SR)-2-{5-[benzenesulfonyl-(7-chloro-1,2,3,4-tetrahydro-cyclopenta[b]indol-2-yl)-fluoro-methyl]-[1,2,4]oxadiazol-3-ylmethyl}-isoindole-1,3-dione as a light yellow solid, MS: 608 ($MNH_4^+$).

Example 90

(RS,SR)-C-{5-[benzenesulfonyl-(7-chloro-1,2,3,4-tetrahydro-cyclopenta[b]indol-2-yl)-fluoro-methyl]-[1,2,4]oxadiazol-3-yl}-methylamine To a stirred suspension of 420 mg (0.71 mmol) of (RS,SR)-2-{5-[benzenesulfonyl-(7-chloro-1,2,3,4-tetrahydro-cyclopenta[b]indol-2-yl)-fluoro-methyl]-[1,2,4]oxadiazol-3-ylmethyl}-isoindole-1,3-dione in 50 mL of EtOH, was added 0.10 mL (2.13 mmol, 3 eq) of hydrazine hydrate. The reaction mixture was heated to 80° C. for 3 hours, before it was partitioned between EtOAc and aqueous HCl 1N. The organic phases were dried over $Na_2SO_4$, filtered and evaporated. Column chromatography on silica gel with $CH_2Cl_2$/MeOH 95:5 afforded 210 mg (64%) of (RS,SR)-C-{5-[benzenesulfonyl-(7-chloro-1,2,3,4-tetrahydro-cyclopenta[b]indol-2-yl)-fluoro-methyl]-[1,2,4]oxadiazol-3-yl}-methylamine light brown solid, MS: 461 ($MH^+$).

Example 91

(RS,SR)-{5-[benzenesulfonyl-(7-chloro-1,2,3,4-tetrahydro-cyclopenta[b]indol-2-yl)-fluoro-methyl]-[1,2,4]oxadiazol-3-ylmethyl}-dimethyl-amine To a stirred solution of 41 mg (0.089 mmol) of (RS,SR)-C-{5-[benzenesulfonyl-(7-chloro-1,2,3,4-tetrahydro-cyclopenta[b]indol-2-yl)-fluoro-methyl]-[1,2,4]oxadiazol-3-yl}-methylamine in MeOH (5 mL), was added 0.07 mL of a formaldehyde solution in water (36%, 0.89 mmol, 10 eq), 12 mg (0.18 mmol, 2 eq) and 1 drop of AcOH. After one hour, the reaction mixture was diluted with water and extracted with EtOAc. The organic phase was dried over $Na_2SO_4$, filtered, and evaporated. Column chromatography on silica gel with EtOAc afforded 9 mg (21%) of (RS,SR)-{5-[benzenesulfonyl-(7-chloro-1,2,3,4-tetrahydro-cyclopenta[b]indol-2-yl)-fluoro-methyl]-[1,2,4]oxadiazol-3-ylmethyl}-dimethyl-amine as a white solid, MS: 489 ($MH^+$).

Example 92

(RS,SR)-{5-[benzenesulfonyl-(7-chloro-1,2,3,4-tetrahydro-cyclopenta[b]indol-2-yl)-fluoro-methyl]-[1,2,4]oxadiazol-3-ylmethyl}-diethyl-amine In analogy to example 91, from (RS,SR)-C-{5-[benzenesulfonyl-(7-chloro-1,2,3,4-tetrahydro-cyclopenta[b]indol-2-yl)-fluoro-methyl]-[1,2,4]oxadiazol-3-yl}-methylamine was prepared (RS,SR)-{5-[benzenesulfonyl-(7-chloro-1,2,3,4-tetrahydro-cyclopenta[b]indol-2-yl)-fluoro-methyl]-[1,2,4]oxadiazol-3-ylmethyl}-diethyl-amine as a white solid, MS: 518 ($MH^+$).

Example 93

(RS,SR)-{5-[benzenesulfonyl-(7-chloro-1,2,3,4-tetrahydro-cyclopenta[b]indol-2-yl)-fluoro-methyl]-[1,2,4]oxadiazol-3-ylmethyl}-diethyl-amine; HCl salt In analogy to example 80, from (RS,SR)-{5-[benzenesulfonyl-(7-chloro-1,2,3,4-tetrahydro-cyclopenta[b]indol-2-yl)-fluoro-methyl]-[1,2,4]oxadiazol-3-ylmethyl}-diethyl-amine was prepared (RS,SR)-{5-[benzenesulfonyl-(7-chloro-1,2,3,4-tetrahydro-cyclopenta[b]indol-2-yl)-fluoro-methyl]-[1,2,4]oxadiazol-3-ylmethyl}-diethyl-amine; HCl salt as a white solid, MS: 518 ($MH^+$).

Example 94

(RS,SR)-2-(benzenesulfonyl-benzooxazol-2-yl-fluoro-methyl)-7-chloro-1,2,3,4-tetrahydro-cyclopenta[b]indole 94.1
A solution of 35 g (0.263 mol) of 2-methyl-benzooxazole in $CCl_4$ (300 mL) was treated with 47 g (0.263, 1 eq) of NBS and 1 g of benzoyl peroxide. The mixture was refluxed (100° C.) over night then cooled. Succinimide was filtered off and the mixture was evaporated to dryness. Column chromatography yielded 9.2 g (17%) of 2-bromomethyl-benzooxazole as a light yellow oil, MS: 210, 212 ($MH^+$). (H. Uno, M. Kurokawa, Y. Masuda, Chem. Pharm. Bull., 1981, 29, 2359).
94.2
To 9.1 g (0.043 mol) of 2-bromomethyl-benzooxazole in $CH_3CN$ (300 mL) were added 7.39 g (0.045 mol, 1.05 eq) of benzenesulfinic acid sodium salt and 2.27 g (8.6 mmol, 0.2 eq) of 18-crown-6. Stirring was continued overnight, solvent evaporated and a column chromatography afforded 8.1 g (70%) of 2-benzenesulfonylmethyl-benzooxazole as a white solid, MS: 274 ($H^+$). (Y. Nagao, S. Yamada, E. Fujita, Tet. Lett., 1983, 24, 2291)
94.3
In analogy to example 74.4, from 2-benzenesulfonylmethyl-benzooxazole and cyclopent-2-enone was prepared 3-(benzenesulfonyl-benzooxazol-2-yl-methyl)-cyclopentanone as a racemic mixture of diastereomers, light yellow oil, MS: 356 ($MH^+$).
94.4
In analogy to example 74.5, from 3-(benzenesulfonyl-benzooxazol-2-yl-methyl)-cyclopentanone and N-fluorobenzenesulfonimide was prepared 3-(benzenesulfonyl-benzooxazol-2-yl-fluoro-methyl)-cyclopentanone as a racemic mixture of diastereomers, white solid, MS: 374 ($MH^+$).
94.5
In analogy to example 89.7, from 3-(benzenesulfonyl-benzooxazol-2-yl-fluoro-methyl)-cyclopentanone and (4-chloro-phenyl)-hydrazine hydrochloride was prepared (RS,SR)-2-(benzenesulfonyl-benzooxazol-2-yl-fluoro-methyl)-7-chloro-1,2,3,4-tetrahydro-cyclopenta[b]indole as a white solid, MS: 481 ($MH^+$).

The enantiomers were separated by preparative chiral HPLC. Column: chiralpak AD, solvent: 20% isopropanol/heptane.

Example 95

(RS,SR)-N-{5-[benzenesulfonyl-(7-chloro-1,2,3,4-tetrahydro-cyclopenta[b]indol-2-yl)-fluoro-methyl]-[1,2,4]oxadiazol-3-ylmethyl}-acetamide To a stirred solution of 57 mg (0.123 mmol) of (RS,SR)-C-{5-[benzenesulfonyl-(7-chloro-1,2,3,4-tetrahydro-cyclopenta[b]indol-2-yl)-fluoro-methyl]-[1,2,4]oxadiazol-3-yl}-methylamine in 5 mL of THF, 20 μL (0.123 mmol, 1 eq) of Huenig base and 11.6 μL (0.123 mmol, 1 eq) of acetic anhydride were added at 0° C. After 30 min., the reaction mixture was quenched by addition of an aqueous solution of NaHCO$_3$ and extracted with CH$_2$Cl$_2$. The combined organic phases were dried over Na$_2$SO$_4$, filtered and evaporated. Column chromatography on silica gel gave 30 mg (48%) of (RS,SR)-N-{5-[benzenesulfonyl-(7-chloro-1,2,3,4-tetrahydro-cyclopenta[b]indol-2-yl)-fluoro-methyl]-[1,2,4]oxadiazol-3-ylmethyl}-acetamide as a light yellow solid, MS: 503 (MH$^+$).

Example 96

(RS,SR)-N-{5-[benzenesulfonyl-(7-chloro-1,2,3,4-tetrahydro-cyclopenta[b]indol-2-yl)-fluoro-methyl]-[1,2,4]oxadiazol-3-ylmethyl}-benzamide To a stirred solution of 44 mg (0.095 mmol) of (RS,SR)-C-{5-[benzenesulfonyl-(7-chloro-1,2,3,4-tetrahydro-cyclopenta[b]indol-2-yl)-fluoro-methyl]-[1,2,4]oxadiazol-3-yl}-methylamine in 5 mL of THF, 19 μL (0.114 mmol, 1.2 eq) of Huenig's base and 11 μL (0.095 mmol, 1 eq) of benzoyl chloride were added at 0° C. After 2 hours, the reaction mixture was quenched by addition of an aqueous solution of NaHCO$_3$ and extracted with CH$_2$Cl$_2$. The combined organic phases were dried over Na$_2$SO$_4$, filtered and evaporated. Column chromatography on silica gel EtOAc/Heptane 1:1 gave 28 mg (51%) of (RS,SR)-N-{5-[benzenesulfonyl-(7-chloro-1,2,3,4-tetrahydro-cyclopenta[b]indol-2-yl)-fluoro-methyl]-[1,2,4]oxadiazol-3-ylmethyl}-benzamide as a white solid, MS: 565 (M).

Example 97

(RS,SR)-2-benzenesulfonyl-2-(6-bromo-2,3,4,9-tetrahydro-1H-carbazol-2-yl)-propionic acid methyl ester Analogously to example 3.2, from (RS,SR)-2-benzenesulfonyl-2-(3-oxo-cyclohexyl)-propionic acid methyl ester and (4-bromo-phenyl)-hydrazine hydrochloride was prepared (RS,SR)-2-benzenesulfonyl-2-(6-bromo-2,3,4,9-tetrahydro-1H-carbazol-2-yl)-propionic acid methyl ester as a white solid, MS: 475 (M, 1Br).

Example 98

(RS,SR)-2-benzenesulfonyl-2-(6-dimethylamino-2,3,4,9-tetrahydro-1H-carbazol-2-yl)-propionic acid methyl ester 98.1
To 1.2 g (2.52 mmol) of (RS,SR)-2-benzenesulfonyl-2-(6-bromo-2,3,4,9-tetrahydro-1H-carbazol-2-yl)-propionic acid methyl ester (from example 99) in 40 mL of THF were added 31 mg (0.25 mmol, 0.1 eq) of DMAP and 660 mg (3.02 mmol, 1.2 eq) of carbonic acid di-tert-butyl ester at 0° C. The reaction mixture was stirred at RT for 2 hours. EtOAc and a solution of aqueous NaHCO$_3$ were added, the phases were separated, and the organic one was extracted with 1M KHSO$_4$. The organic phases were dried over Na$_2$SO$_4$, filtered and evaporated. Column chromatography afforded 1.3 g (90%) of (RS,SR)-2-(-1-benzenesulfonyl-1-methoxycarbonyl-ethyl)-6-bromo-1,2,3,4-tetrahydro-carbazole-9-carboxylic acid tert-butyl ester as white solid, MS: 575 (M,1Br).
98.2

Under argon a flask was charged with 24 mg of (0.03 mmol, 0.05 eq) tris(dibenzylidene-acetone) dipalladium, 16 mg (0.05 mmol, 0.1 eq) of 2(di-tertbutylphosphino)biphenyl and 85 mg (0.88 mmol, 1.7 eq) of sodium tert-butylate, evacuated and backfilled with argon. 300 mg (0.52 mmol) of (RS,SR)-2-(-1-benzenesulfonyl-1-methoxycarbonyl-ethyl)-6-bromo-1,2,3,4-tetrahydro-carbazole-9-carboxylic acid tert-butyl ester in 15 ml of toluene were added, followed by a solution of 1.95 ml 2M (3.9 mmol, 7.5 eq) of dimethylamine in THF. The solution was heated to 80° C. overnight in a sealed tube. The mixture was diluted with EtOAc and a saturated solution of Na$_2$CO$_3$ was added. The inorganic layer was extracted with EtOAc. The combined organic phases were washed with brine and dried over Na$_2$SO$_4$. Column chromatography yielded 68 mg (24%) of (RS,SR)-2-(-1-benzenesulfonyl-1-methoxycarbonyl-ethyl)-6-dimethylamino-1,2,3,4-tetrahydro-carbazole-9-carboxylic acid tert-butyl ester as orange oil, MS: 541 (MH$^+$).
98.3
To 42 mg (9.3 mmol) of (RS,SR)-2-(-1-benzenesulfonyl-1-methoxycarbonyl-ethyl)-6-dimethylamino-1,2,3,4-tetrahydro-carbazole-9-carboxylic acid tert-butyl ester in 1 ml of CH$_2$Cl$_2$ were added 0.06 ml of TFA at 0° C. The solution was stirred at RT for 5 h, a NaHCO$_3$ solution was added, and the inorganic phase was extracted with CH$_2$Cl$_2$, washed with brine and dried over Na$_2$SO$_4$. Column chromatography on ISOLUTE Flash NH2 (Separtis, aminopropyl-modified silicagel) with EtOAc/heptane 2:1, followed by tituration with ether/heptane yielded 190 mg (56%) of (RS,SR)-2-benzenesulfonyl-2-(6-dimethylamino-2,3,4,9-tetrahydro-1H-carbazol-2-yl)-propionic acid methyl ester as light green amorphous material, MS: 441 (MH$^+$).

Example 99

(6-bromo-2,3,4,9-tetrahydro-1H-carbazol-2-yl)-methanesulfonyl-acetic acid methyl ester 99.1
Analogously to example 1.1, from methyl methylsulfonylacetate and 2-cyclohexen-1-one were prepared methanesulfonyl-(3-oxo-cyclohexyl)-acetic acid methyl ester as a racemic mixture of diastereomers, orange amorphous material, MS: 249 (MH$^+$).
99.2
Analogously to example 1.2, from methanesulfonyl-(3-oxo-cyclohexyl)-acetic acid methyl ester and (4-bromo-phenyl)-hydrazine hydrochloride was prepared (6-bromo-2,3,4,9-tetrahydro-1H-carbazol-2-yl)-methanesulfonyl-acetic acid methyl ester as a racemic mixture of diastereomers, light brown solid, MS: 400 (MH$^+$,1Br).

Example 100

(RS,SR)-2-(6-bromo-2,3,4,9-tetrahydro-1H-carbazol-2-yl)-2-methanesulfonyl-propionic acid methyl ester 100.1
Analogously to example 3.1, from a racemic mixture of diastereomers of methanesulfonyl-(3-oxo-cyclohexyl)-acetic acid methyl ester (from example 101.1) and methyl iodide was prepared a racemic mixture of diastereomers of 2-methanesulfonyl-2-(3-oxo-cyclohexyl)-propionic acid methyl ester as a colorless foam, MS: 263 (MH$^+$).

100.2

Analogously to example 1.2, from a racemic mixture of diastereomers of 2-methanesulfonyl-2-(3-oxo-cyclohexyl)-propionic acid methyl ester and (4-bromo-phenyl)-hydrazine hydrochloride were prepared the following 2 racemic diastereomers which could be separated by column chromatography to yield (RS,SR)-2-(6-bromo-2,3,4,9-tetrahydro-1H-carbazol-2-yl)-2-methanesulfonyl-propionic acid methyl ester, MS: 414 (MH$^+$,1Br), and (RR,SS)-2-(6-bromo-2,3,4,9-tetrahydro-1H-carbazol-2-yl)-2-methanesulfonyl-propionic acid methyl ester, MS: 414 (MH$^+$,1Br).

Example 101

(RS,SR)-2-(6-dimethylamino-2,3,4,9-tetrahydro-1H-carbazol-2-yl)-2-methanesulfonyl-propionic acid methyl ester 101.1

Analogously to example 98.1, from (RS,SR)-2-(6-bromo-2,3,4,9-tetrahydro-1H-carbazol-2-yl)-2-methanesulfonyl-propionic acid methyl ester (from example 102.2) was prepared (RS,SR)-6-bromo-2-(1-methanesulfonyl-1-methoxycarbonyl-ethyl)-1,2,3,4-tetrahydro-carbazole-9-carboxylic acid tert-butyl ester as white solid, MS: 531(M+NH4$^+$, 1Br).

101.2

Analogously to example 98.2, from (RS,SR)-6-bromo-2-(1-methanesulfonyl-1-methoxycarbonyl-ethyl)-1,2,3,4-tetrahydro-carbazole-9-carboxylic acid tert-butyl ester was prepared (RS,SR)-6-dimethylamino-2-(1-methanesulfonyl-1-methoxycarbonyl-ethyl)-1,2,3,4-tetrahydro-carbazole-9-carboxylic acid tert-butyl ester as light yellow solid, MS: 479 (MH$^+$).

101.3

Analogously to example 98.3, from (RS,SR)-6-dimethylamino-2-(1-methanesulfonyl-1-methoxycarbonyl-ethyl)-1,2,3,4-tetrahydro-carbazole-9-carboxylic acid tert-butyl ester was prepared (RS,SR)-2-(6-dimethylamino-2,3,4,9-tetrahydro-1H-carbazol-2-yl)-2-methanesulfonyl-propionic acid methyl ester as light green foam, MS: 378 (M).

Example 102

(3-bromo-benzenesulfonyl)-(7-chloro-1,2,3,4-tetrahydro-cyclopenta[b]indol-2-yl)-acetic acid methyl ester 102.1

A solution of 8.0 g (42 mmol) of 3-bromothiophenol was treated with 7.1 g (47 mmol) of methyl bromoacetate and potassium carbonate. The resulting suspension was stirred at reflux for 24 hrs, cooled to RT and neutralized with a saturated aqueous solution of NH$_4$Cl. Diethylether was added, the phases were separated and the aqueous one was extracted twice with diethylether. The combined organic phases were dried over Na$_2$SO$_4$, filtered and evaporated to give 12.1 g (99%) of (3-bromo-phenylsulfanyl)-acetic acid methyl ester as a light yellow oil, MS: 279 (MNH$_4^+$, 1Br).

102.2

A solution of 6.0 g (23 mmol) of (3-bromo-phenylsulfanyl)-acetic acid methyl ester in 50 mL of dichloroethane was treated with 6.2 g (25 mmol) of 3-chloroperbenzoic acid. After 30 min of stirring another 6.2 g (25 mmol) of 3-chloroperbenzoic acid were added, the resulting suspension was stirred overnight at RT and then treated with a 0.5 M aqueous solution of sodium thiosulfate. The phases were separated and the aqueous one extracted twice with diethylether. The combined organic phases were washed with a ca. 1M aqueous NaHCO$_3$ solution, dried over Na$_2$SO$_4$, filtered and evaporated to give 6.3 g (93%) of (3-bromo-benzenesulfonyl)-acetic acid methyl ester as a colorless oil, MS: 312 (MNH$_4^+$, 1Br).

102.3

In analogy to example 74.4, from (3-bromo-benzenesulfonyl)-acetic acid methyl ester and cyclopent-2-enone was prepared (3-bromo-benzenesulfonyl)-(3-oxo-cyclopentyl)-acetic acid methyl ester as a racemic mixture of diastereomers, colorless gum, MS: 394 (MNH$_4^+$, 1Br).

102.4

In analogy to example 1.2, from (3-bromo-benzenesulfonyl)-(3-oxo-cyclopentyl)-acetic acid methyl ester (racemic mixture of diastereomers) and (4-chlorophenyl)-hydrazine hydrochloride was prepared (3-bromo-benzenesulfonyl)-(7-chloro-1,2,3,4-tetrahydro-cyclopenta[b]indol-2-yl)-acetic acid methyl ester as a racemic mixture of diastereomers, orange solid, MS: 484 (MH$^+$, 1Br).

Example 103

(RS, SR)-2-(3-bromo-benzenesulfonyl)-2-((7-chloro-1,2,3,4-tetrahydro-cyclopenta[b]indol-2-yl)-propionic acid methyl ester 103.1

In analogy to example 3.1, but omitting the separation of the diastereomers, from (3-bromo-benzenesulfonyl)-(3-oxo-cyclopentyl)-acetic acid methyl ester (racemic mixture of diastereomers) and iodomethane was prepared 2-(3-bromo-benzenesulfonyl)-2-(3-oxo-cyclopentyl)-propionic acid methyl ester as a racemic mixture of diastereomers, colorless oil, MS: 408 (MNH$_4^+$, 1Br).

103.2

In analogy to example 3.2 from 2-(3-bromo-benzenesulfonyl)-2-(3-oxo-cyclopentyl)-propionic acid methyl ester (racemic mixture of diastereomers) and (4-chlorophenyl)-hydrazine hydrochloride was prepared (3-bromo-benzenesulfonyl)-2-(7-chloro-1,2,3,4-tetrahydro-cyclopenta[b]indol-2-yl)-propionic acid methyl ester as a racemic mixture of diastereomers. The diastereomers were separated by chromatography on silica gel with heptane/EtOAc to give (RS, SR)-2-(3-bromo-benzenesulfonyl)-2-(7-chloro-1,2,3,4-tetrahydro-cyclopenta[b]indol-2-yl)-propionic acid methyl ester as a brown solid, MS: 498 (MH$^+$, 1Br) and (RR, SS)-2-(3-bromo-benzenesulfonyl)-2-(7-chloro-1,2,3,4-tetrahydro-cyclopenta[b]indol-2-yl)-propionic acid methyl ester as an orange solid, MS: 498 (MH$^+$, 1Br).

Example 104

(RS, SR)-(7-chloro-1,2,3,4-tetrahydro-cyclopenta[b]indol-2-yl)-2-(3-pyrrolidin-1-yl-benzenesulfonyl)-propionic acid methyl ester A solution of 40 mg (0.08 mmol) (RS, SR)-2-(3-bromo-benzenesulfonyl)-2-(7-chloro-1,2,3,4-tetrahydro-cyclopenta[b]indol-2-yl)-propionic acid methyl ester (example 103) in toluene was treated with 13 mg (0.13 mmol) of NaOtBu, 2 mg (0.007 mmol) of 2-(di-tbutylphosphino)biphenyl, 0.03 mL (0.4 mmol) of pyrrolidine and 4 mg (0.004 mmol) of tris(dibenzylideneacetone)dipalladium. The resulting suspension was stirred at 80° for 4 hrs, treated with a diluted aqueous NaHCO$_3$-solution and extracted twice with EtOAc. The combined organic phases were dried over Na$_2$SO$_4$, filtered and evaporated to give 14 mg (35%) of (RS, SR)-(7-chloro-1,2, 3,4-tetrahydro-cyclopenta[b]indol-2-yl)-2-(3-pyrrolidin-1-yl-benzenesulfonyl)-propionic acid methyl ester as a light brown solid, MS: 488 (MH$^+$).

Example 105

(RS, SR) 2-[1-(3-bromo-benzenesulfonyl)-1-(5-methyl-[1,3,4]oxadiazol-2-yl)-ethyl]-7-chloro-1,2,3,4-tetrahydro-cyclopenta[b]indole 105.1
In analogy to examples 74.1-74.3, from (3-bromo-benzenesulfonyl)-acetic acid methyl ester was prepared 2-(3-bromo-benzenesulfonylmethyl)-5-methyl-[1,3,4]oxadiazole as a light yellow oil. MS: 319 (MH$^+$, 1Br).

105.2
In analogy to example 74.4, from 2-(3-bromo-benzenesulfonylmethyl)-5-methyl-[1,3,4]oxadiazole and cyclopent-2-enone was prepared 3-[(3-bromo-benzenesulfonyl)-(5-methyl-[1,3,4]oxadiazol-2-yl)-methyl]-cyclopentanone as a racemic mixture of diastereomers, white solid, MS: 400 (MH$^+$, 1Br).

105.3
In analogy to example 103.1, from 3-[(3-bromo-benzenesulfonyl)-(5-methyl-[1,3,4]oxadiazol-2-yl)-methyl]-cyclopentanone (racemic mixture of diastereomers) and iodomethane was prepared 3-[1-(3-bromo-benzenesulfonyl)-1-(5-methyl-[1,3,4]oxadiazol-2-yl)-ethyl]-cyclopentanone as a racemic mixture of diastereomers, yellow oil, MS: 414 (MH$^+$, 1Br).

105.4
In analogy to example 103.2, from 3-[1-(3-bromo-benzenesulfonyl)-1-(5-methyl-[1,3,4]oxadiazol-2-yl)-ethyl]-cyclopentanone (racemic mixture of diastereomers) and (4-chlorophenyl)-hydrazine hydrochloride were prepared (RS, SR) 2-[1-(3-bromo-benzenesulfonyl)-1-(5-methyl-[1,3,4]oxadiazol-2-yl)-ethyl]-7-chloro-1,2,3,4-tetrahydro-cyclopenta[b]indole as a dark brown gum, MS: 522 (MH$^+$, 1Br) and (RR, SS) 2-[1-(3-bromo-benzenesulfonyl)-1-(5-methyl-[1,3,4]oxadiazol-2-yl)-ethyl]-7-chloro-1,2,3,4-tetrahydro-cyclopenta[b]indole as a dark brown solid, MS: 522 (MH$^+$, 1Br).

Example 106

(RS, SR)-2-[(3-bromo-benzenesulfonyl)-fluoro-(5-methyl-[1,3,4]oxadiazol-2-yl)-methyl]-7-chloro-1,2,3,4-tetrahydro-cyclopenta[b]indole 106.1
In analogy to example 12.1, from 3-[(3-bromo-benzenesulfonyl)-(5-methyl-[1,3,4]oxadiazol-2-yl)-methyl]-cyclopentanone (racemic mixture of diastereomers) and N-fluorobenzenesulfonimide was prepared 3-[(3-bromo-benzenesulfonyl)-fluoro-(5-methyl-[1,3,4]oxadiazol-2-yl)-methyl]-cyclopentanone as a racemic mixture of diastereomers, white solid, MS: 418 (MH$^+$, 1Br).

106.2
In analogy to example 103.2, from 3-[(3-bromo-benzenesulfonyl)-fluoro-(5-methyl-[1,3,4]oxadiazol-2-yl)-methyl]-cyclopentanone (racemic mixture of diastereomers) and (4-chlorophenyl)-hydrazine hydrochloride was prepared (RS, SR)-2-[(3-bromo-benzenesulfonyl)-fluoro-(5-methyl-[1,3,4]oxadiazol-2-yl)-methyl]-7-chloro-1,2,3,4-tetrahydro-cyclopenta[b]indole as a brown gum, MS: 526 (MH$^+$, 1Br) and (RR, SS)-2-[(3-bromo-benzenesulfonyl)-fluoro-(5-methyl-[1,3,4]oxadiazol-2-yl)-methyl]-7-chloro-1,2,3,4-tetrahydro-cyclopenta[b]indole as a light brown solid, MS: 526 (MH$^+$, 1Br).

Example 107

(RS, SR) 2-[(5-benzyl-[1,3,4]oxadiazol-2-yl)-(3-bromo-benzenesulfonyl)-fluoro-methyl]-7-chloro-1,2,3,4-tetrahydro-cyclopenta[b]indole 107.1
In analogy to example 74.1, from 3-bromobenzenesulfonyl-acetic acid methyl ester (example 102.2) and hydrazine hydrate was prepared 3-bromobenzenesulfonyl-acetic acid hydrazide as a colorless oil, MS: 294 (MH$^+$, 1Br).

107.2
In analogy to example 74.2, from 3-bromobenzenesulfonyl-acetic acid hydrazide and phenylacetyl chloride was prepared phenyl-acetic acid N-[2-(3-bromo-benzenesulfonyl)-acetyl]-hydrazide as a white solid, MS: 412 (MH$^+$, 1Br).

107.3
In analogy to example 74.3, by treatment of phenyl-acetic acid N-[2-(3-bromo-benzenesulfonyl)-acetyl]-hydrazide with phosphorous oxychloride was prepared 2-benzyl-5-(3-bromo-benzenesulfonylmethyl)-[1,3,4]oxadiazole as an orange oil, MS: 394 (MH$^+$, 1Br).

107.4
In analogy to example 74.4, from 2-benzyl-5-(3-bromo-benzenesulfonylmethyl)-[1,3,4]oxadiazole and cyclopent-2-enone was prepared 3-[(5-benzyl-[1,3,4]oxadiazol-2-yl)-(3-bromo-benzenesulfonyl)-methyl]-cyclopentanone as a racemic mixture of diastereomers, colorless gum, MS: 476 (MH$^+$, 1Br).

107.5
In analogy to example 12.1, from 3-[(5-benzyl-[1,3,4]oxadiazol-2-yl)-(3-bromo-benzenesulfonyl)-methyl]-cyclopentanone (racemic mixture of diastereomers) and N-fluorobenzenesulfonimide, was prepared 3-[(5-benzyl-[1,3,4]oxadiazol-2-yl)-(3-bromo-benzenesulfonyl)-fluoro-methyl]-cyclopentanone as a racemic mixture of diastereomers light yellow solid, MS: 494 (MH$^+$, 1Br).

107.6
In analogy to example 103.2 from 3-[(5-benzyl-[1,3,4]oxadiazol-2-yl)-(3-bromo-benzenesulfonyl)-fluoro-methyl]-cyclopentanone (racemic mixture of diastereomers) and (4-chlorophenyl)-hydrazine hydrochloride was prepared (RS, SR)-2-[(5-benzyl-[1,3,4]oxadiazol-2-yl)-(3-bromo-benzenesulfonyl)-fluoro-methyl]-7-chloro-1,2,3,4-tetrahydro-cyclopenta[b]indole as a yellow solid, MS: 602 (MH$^+$, 1Br) and (RR, SS)-2-[(5-benzyl-[1,3,4]oxadiazol-2-yl)-(3-bromo-benzenesulfonyl)-fluoro-methyl]-7-chloro-1,2,3,4-tetrahydro-cyclopenta[b]indole as a brown solid, MS: 602 (MH$^+$, 1Br).

Example 108

(RS, SR) {3-[(7-chloro-1,2,3,4-tetrahydro-cyclopenta[b]indol-2-yl)-fluoro-(5-methyl-[1,3,4]oxadiazol-2-yl)-methanesulfonyl]-phenyl}-dimethyl-amine In analogy to example 104 from (RS, SR)-2-[(3-bromo-benzenesulfonyl)-fluoro-(5-methyl-[1,3,4]oxadiazol-2-yl)-methyl]-7-chloro-1,2,3,4-tetrahydro-cyclopenta[b]indole (example 106) and dimethylamine in THF was prepared (RS, SR) {3-[(7-chloro-1,2,3,4-tetrahydro-cyclopenta[b]indol-2- yl)-fluoro-(5-methyl-[1,3,4]oxadiazol-2-yl)-methanesulfonyl]-phenyl}-dimethyl-amine as a yellow gum, MS: 489 (MH$^+$).

Example 109

(RS, SR)-7-chloro-2-[(3-ethynyl-benzenesulfonyl)-fluoro-(5-methyl-[1,3,4]oxadiazol-2-yl)-methyl]-1,2,3,4-tetrahydro-cyclopenta[b]indole A solution of 76 mg (0.133 mmol) of (RS, SR)-2-[(3-bromo-benzenesulfonyl)-fluoro-(5-methyl-[1,3,4]oxadiazol-2-yl)-methyl]-7-chloro-1,2,3,4-tetrahydro-cyclopenta[b]indole (example 106) in 1.5 mL of DMF was treated with 1 mg (0.005 mmol) of CuI, 37 mg (0.29 mmol) of DIPEA, 17 mg (0.015 mmol) of tetrakis(triphenylphosphine)palladium and 71 mg (0.72 mmol) of ethynyltrimethylsilane and the resulting suspension stirred at 80° C. during 4 hrs. Diluted aqueous NaOH was added and the mixture extracted twice with dichloromethane. The combined organic layers were dried over Na$_2$SO$_4$, filtered and evaporated. Chromatography on silica gel with heptane/EtOAc (1:1) gave 33 mg (48%) of (RS, SR)-7-chloro-2-[(3-ethynyl-benzenesulfonyl)-fluoro-(5-methyl-[1,3,4]oxadiazol-2-yl)-methyl]-1,2,3,4-tetrahydro-cyclopenta[b]indole as a yellow solid, MS: 471 (MH$^+$).

Example 110

(RS, SR)-2-[5-(4-benzyloxy-benzyl)-[1,3,4]oxadiazol-2-yl-(3-bromo-benzenesulfonyl)-fluoro-methyl]-7-chloro-1,2,3,4-tetrahydro-cyclopenta[b]indole 110.1
In analogy to example 74.2, from 3-bromobenzenesulfonyl-acetic acid hydrazide (example 107.1) and 4-benzyloxyphenylacetyl chloride was prepared (4-benzyloxy-phenyl)-acetic acid N-[2-(3-bromo-benzenesulfonyl)-acetyl]-hydrazide as a light yellow solid, MS: 518 (MH$^+$, 1Br).

110.2
In analogy to examples 74.3, by treatment of (4-benzyloxy-phenyl)-acetic acid N-[2-(3-bromo-benzenesulfonyl)-acetyl]-hydrazide with phosphorous oxychloride was prepared 2-(4-benzyloxy-benzyl)-5-(3-bromo-benzenesulfonylmethyl)-[1,3,4]oxadiazole as a light yellow solid, MS: 500 (MH$^{30}$, 1Br).

110.3
In analogy to example 74.4, from 2-(4-benzyloxy-benzyl)-5-(3-bromo-benzenesulfonylmethyl)-[1,3,4]oxadiazole and cyclopent-2-enone was prepared 3-[[5-(4-benzyloxy-benzyl)-[1,3,4]oxadiazol-2-yl]-(3-bromo-benzenesulfonyl)-methyl]-cyclopentanone as a racemic mixture of diastereomers, white solid, MS: 582 (MH$^+$, 1Br).

110.4
In analogy to example 12.1, from 3-[[5-(4-benzyloxy-benzyl)-[1,3,4]oxadiazol-2-yl]-(3-bromo-benzenesulfonyl)-methyl]-cyclopentanone (racemic mixture of diastereomers) and N-fluorobenzenesulfonimide, was prepared 3-[[5-(4-benzyloxy-benzyl)-[1,3,4]oxadiazol-2-yl]-(3-bromo-benzenesulfonyl)-fluoro-methyl]-cyclopentanone as a racemic mixture of diastereomers white solid, MS: 600 (MH$^{30}$, 1Br).

110.5
In analogy to example 103.2 from 3-[[5-(4-benzyloxy-benzyl)-[1,3,4]oxadiazol-2-yl]-(3-bromo-benzenesulfonyl)-fluoro-methyl]-cyclopentanone (racemic mixture of diastereomers) and (4-chlorophenyl)-hydrazine hydrochloride was prepared (RS, SR)-2-[5-(4-benzyloxy-benzyl)-[1,3,4]oxadiazol-2-yl-(3-bromo-benzenesulfonyl)-fluoro-methyl]-7-chloro-1,2,3,4-tetrahydro-cyclopenta[b]indole as a brown solid, MS: 708 (MH$^+$, 1Br) and (RR, SS)-2-[5-(4-benzyloxy-benzyl)-[1,3,4]oxadiazol-2-yl-(3-bromo-benzenesulfonyl)-fluoro-methyl]-7-chloro-1,2,3,4-tetrahydro-cyclopenta[b]indole as a yellow solid, MS: 708 (MH$^{30}$, 1Br).

Example 111

(RS, SR)-7-chloro-2-[(3-ethyl-benzenesulfonyl)-fluoro-(5-methyl-[1,3,4]oxadiazol-2-yl)-methyl]-1,2,3,4-tetrahydro-cyclopenta[b]indole A solution of 22 mg (0.05 mmol) (RS, SR)-7-chloro-2-[(3-ethynyl-benzenesulfonyl)-fluoro-(5-methyl-[1,3,4]oxadiazol-2-yl)-methyl]-1,2,3,4-tetrahydro-cyclopenta[b]indole in 0.5 mL of methanol was treated with 1 mg of palladium on activated charcoal (10%) and stirred intensely under H$_2$ (atmospheric pressure) during 5 hrs. Filtration and evaporation of the solvent gave 21 mg (92%) of (RS, SR) 7-chloro-2-[(3-ethyl-benzenesulfonyl)-fluoro-(5-methyl-[1,3,4]oxadiazol-2-yl)-methyl]-1,2,3,4-tetrahydro-cyclopenta[b]indole, as a yellow solid, MS: 475 (MH$^+$)

Example 112

(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzoic acid methyl ester 112.1
In analogy to example 74.2, from 3-bromobenzenesulfonyl-acetic acid hydrazide (example 107.1) and methyl 4-chlororcarbonylbenzoate was prepared 4-{N-[2-(3-bromo-benzenesulfonyl)-acetyl]-hydrazinocarbonyl}-benzoic acid methyl ester, as a light yellow solid, MS: 456 (MH$^{30}$, 1Br).

112.2
In analogy to example 74.3, by treatment of 4-{N-[2-(3-bromo-benzenesulfonyl)-acetyl]-hydrazinocarbonyl}-benzoic acid methyl ester with phosphorous oxychloride was prepared 4-[5-(3-bromo-benzenesulfonylmethyl)-[1,3,4]oxadiazol-2-yl]-benzoic acid methyl ester as a light yellow solid, MS: 438 (MH$^+$, 1Br).

112.3
In analogy to example 74.4, from 4-[5-(3-bromo-benzenesulfonylmethyl)-[1,3,4]oxadiazol-2-yl]-benzoic acid methyl ester and cyclopent-2-enone was prepared 4-{5-[(3-bromo-benzenesulfonyl)-(3-oxo-cyclopentyl)-methyl]-[1,3,4]oxadiazol-2-yl}-benzoic acid methyl ester as a racemic mixture of diastereomers, white solid, MS: 520 (MH$^+$, 1Br).

112.4
In analogy to example 12.1, from 4-{5-[(3-bromo-benzenesulfonyl)-(3-oxo-cyclopentyl)-methyl]-[1,3,4]oxadiazol-2-yl}-benzoic acid methyl ester (racemic mixture of diastereomers) and N-fluorobenzenesulfonimide was prepared 4-{5-[(3-bromo-benzenesulfonyl)-fluoro-(3-oxo-cyclopentyl)-methyl]-[1,3,4]oxadiazol-2-yl}-benzoic acid methyl ester as a racemic mixture of diastereomers white solid, MS: 538 (MH$^+$, 1Br).

112.5
In analogy to example 103.2, from 4-{5-[(3-bromo-benzenesulfonyl)-fluoro-(3-oxo-cyclopentyl)-methyl]-[1,3,4]oxadiazol-2-yl}-benzoic acid methyl ester (racemic mixture of diastereomers) and (4-chlorophenyl)-hydrazine was prepared (RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzoic acid methyl ester as a brown solid, MS: 646 (MH⁺, 1Br) and (RR, SS) 4-{5-[(3-bromo-benzene-sulfonyl)-(7-chloro-1,2,3,4-tetrahydro-cyclopenta[b]indol-2-yl)-fluoro-methyl]-[1,3,4]oxadiazol-2-yl}-benzoic acid methyl ester as a light brown solid, MS: 646 (MH⁺, 1Br).

Example 113

(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzoic acid A solution of 13 mg (0.02 mmol) of (RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzoic acid methyl ester in a 1:1 mixture of 0.5 mL of THF and 0.5 mL of 1M aqueous LiOH was stirred at RT during one hour. Diluted aqueous HCl was added and the mixture extracted twice with dichloromethane. Drying of the combined organic phases over Na₂SO₄, filtration and evaporation of the solvent gave ca 13 mg (quantitative) of (RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzoic acid as a yellow solid, MS: 632 (MH³⁰, 1Br).

Example 114

(RS, SR) (4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-phenyl)-methanol A solution of 12 mg (0.02 mmol) of (RS, SR) 4-[5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzoic acid methyl ester in 0.5 mL of THF was treated with 3 mg (0.08 mmol) of lithium aluminiumhydride and stirred at RT for one hour. The mixture was treated with a mixture of ice cubes and water and extracted twice with dichlormothane. Drying of the combined organic phases over Na₂SO₄, filtration and evaporation gave 10 mg (86%) of (RS, SR) (4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-phenyl)-methanol as a yellow solid, MS: 618 (MH⁺, 1Br).

Example 115

(RS, SR) 2-{benzenesulfonyl-fluoro-[5-(4-iodo-benzyl)-[1,3,4]oxadiazol-2-yl]-methyl}-7-chloro-1,2,3,4-tetrahydro-cyclopenta[b]indole 115.1
A solution of 1 g (4.7 mmol) of benzenesulfonyl-acetic acid hydrazide (example 74.1) in 4 mL of THF was treated with 391 mg (4.7 mmol) of iodophenylacetic acid, 126 mg (0.93 mmol) of 1-hydroxybenzotriazole and 2.8 g (28 mmol) of N-methylmorpholine. The mixture was stirred during 15 min at 0° C., treated with 1.25 g (6.5 mmol) of EDCI and stirred during 12 hrs. The crude was treated with diluted aqueous NH₄Cl and extracted twice with EtOAc. Drying of the combined organic layers over Na₂SO₄, filtration and evaporation gave 2 g (93%) of benzenesulfonyl-acetic acid N'-[2-(4-iodo-phenyl)-acetyl]-hydrazide as a brown oil, MS: 266 (MH⁺)

115.2
In analogy to example 74.3, by treatment of (4-iodo-phenyl)-acetic acid N-[2-(benzenesulfonyl)-acetyl]-hydrazide with phosphorous oxychloride was prepared 2-benzenesulfonylmethyl-5-(4-iodo-benzyl)-[1,3,4]oxadiazole as a light yellow solid, MS: 441 (MH⁺)

115.3
In analogy to example 74.4, from 2-benzenesulfonylmethyl-5-(4-iodo-benzyl)-[1,3,4]oxadiazole and cyclopent-2-enone was prepared 3-{(benzenesulfonyl)-[5-(4-iodo-benzyl)-[1,3,4]oxadiazol-2-yl]-methyl}-cyclopentanone as a racemic mixture of diastereomers, light brown gum, MS: 523 (MH⁺).

115.4
In analogy to example 12.1, from 3-{(benzenesulfonyl)-[5-(4-iodo-benzyl)-[1,3,4]oxadiazol-2-yl]-methyl}-cyclopentanone (racemic mixture of diastereomers) and N-fluorobenzenesulfonimide, was prepared 3-{(3-bromo-benzenesulfonyl)-fluoro-[5-(4-iodo-benzyl)-[1,3,4]oxadiazol-2-yl]-methyl}-cyclopentanone as a racemic mixture of diastereomers that was separated by chormatography on silica gel with EtOAc/heptane 1:2 to give to give N-fluorobenzenesulfonimide, was prepared (RS, SR) 3-{(benzenesulfonyl)-fluoro-[5-(4-iodo-benzyl)-[1,3,4]oxadiazol-2-yl]-methyl}-cyclopentanone as a white solid MS: 541 (MH⁺), and (RR, SS) 3-{(benzenesulfonyl)-fluoro-[5-(4-iodo-benzyl)-[1,3,4]oxadiazol-2-yl]-methyl}-cyclopentanone as a white solid MS: 541 (MH⁺).

115.5
In analogy to example 103.2 from (RS, SR) 3-{(benzenesulfonyl)-fluoro-[5-(4-iodo-benzyl)-[1,3,4]oxadiazol-2-yl]-methyl}-cyclopentanone and (4-chlorophenyl)-hydrazine hydrochloride was prepared (RS, SR) 2-{benzenesulfonyl-fluoro-[5-(4-iodo-benzyl)-[1,3,4]oxadiazol-2-yl]-methyl}-7-chloro-1,2,3,4-tetrahydro-cyclopenta[b]indole light yellow solid, MS: 648 (MH⁺).

Example 116

(RS, SR) 4-{5-[(benzenesulfonyl)-(7-chloro-1,2,3,4-tetrahydro-cyclopenta[b]indol-2-yl)-fluoro-methyl]-[1,3,4]oxadiazol-2-yl}-benzoic acid A solution of 17 mg (0.027 mmol) of (RS, SR) 4-{5-[3-bromo-benzenesulfonyl)-(7-chloro-1,2,3,4-tetrahydro-cyclopenta[b]indol-2-yl)-fluoro-methyl]-[1,3,4]oxadiazol-2-yl}-benzoic acid in 1 mL of methanol was treated with 1 mg of palladium on activated charcoal (10%) and intensely stirred during 2 hrs under H₂ (atmospheric pressure). Filtration and evaporation of the solvent gave 14 mg (94%) of (RS, SR) 4-{5-[(benzenesulfonyl)-(7-chloro-1,2,3,4-tetrahydro-cyclopenta[b]indol-2-yl)-fluoro-methyl]-[1,3,4]oxadiazol-2-yl}-benzoic acid as a white solid, MS: 553 (MHⁱ).

Example 117

(RS, SR) 4-{5-[benzenesulfonyl-(7-chloro-1,2,3,4-tetrahydro-cyclopenta[b]indol-2-yl)-fluoro-methyl]-[1,3,4]oxadiazol-2-ylmethyl}-benzoic acid A solution of 66 mg (0.10 mmol) of (RS, SR) 2-{benzenesulfonyl-fluoro-[5-(4-iodo-benzyl)-[1,3,4]oxadiazol-2-yl]-methyl}-7-chloro-1,2,3,4-tetrahydro-cyclopenta[b]indole (example 115) in 0.5 mL of DMF and 0.5 mL of water was treated with 1 mg of NaI and 2 mg (0.009 mmol) of palladium acetate. The mixture was then stirred for 144 hrs under CO (atmospheric pressure), treated with 2M aqueous HCl and extracted with dichloromethane. Drying of the combined organic phases over $Na_2SO_4$, filtration and evaporation of the solvent gave 45 mg (78%) of (RS, SR) 4-{5-[benzenesulfonyl-(7-chloro-1,2,3,4-tetrahydro-cyclopenta[b]indol-2-yl)-fluoro-methyl]-[1,3,4]oxadiazol-2-ylmethyl}-benzoic acid as a light brown solid, MS: 566 ($MH^+$).

Example 118

(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzamide A solution of 63 mg (0.1 mmol) of (RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzoic acid (example 113) in 0.5 mL of DMF was treated with 27 mg (0.511 mmol) of $NH_4Cl$, 61 mg (0.6 mmol) of N-methylmorpholine, 3 mg (0.02 mmol) and of 1-hydroxybenzotriazole. The mixture was stirred for 15 at 0° C. and treated with 29 mg (0.15 mmol) of EDCI and stirred at RT for 10 hrs. A diluted aqueous solution of HCl was added and the mixture extracted with EtOAc. The combined organic phases were dried over $Na_2SO_4$, filtered and the solvent evaporated to give 60 mg of (RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzamide as a brown solid, MS: 630 ($MH^+$, 1Br).

Example 119

(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-N-methyl-benzamide In analogy to example 118, from (RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzoic acid (example 113) and methylamine hydrochloride was prepared (RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-N-methyl-benzamide as a brown solid, MS: 643 ($MH^{30}$, 1Br).

Example 120

(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-N,N-dimethyl-benzamide In analogy to example 118, from (RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzoic acid (example 113) and dimethylamine hydrochloride was prepared (RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-N,N-dimethyl-benzamide as a brown solid, MS: 657 ($MH^{30}$, 1Br).

Example 121

(RS,SR)-2-[-benzenesulfonyl-fluoro-(5-methyl-[1,3,4]oxadiazol-2-yl)-methyl]-7-bromo-1,2,3,4-tetrahydro-cyclopenta[b]indole In analogy to example 74.6, from (RS,SR)-3-[benzenesulfonyl-fluoro-(5-methyl-[1,3,4]oxadiazol-2-yl)-methyl]-cyclopentanone (example 74.5) and (4-bromo-phenyl)-hydrazine hydrochloride was prepared (RS,SR)-2-[-benzenesulfonyl-fluoro-(5-methyl-[1,3,4]oxadiazol-2-yl)-methyl]-7-bromo-1,2,3,4-tetrahydro-cyclopenta[b]indole as light brown solid, MS: 489 (M, 1Br).

Example 122

(RS,SR)-2-[-benzenesulfonyl-fluoro-(5-methyl-[1,3,4]oxadiazol-2-yl)-methyl]-7-piperidin-1-yl-1,2,3,4-tetrahydro-cyclopenta[b]indole 122.1

Analogously to example 98.1, from (RS,SR)-2-[-benzenesulfonyl-fluoro-(5-methyl-[1,3,4]oxadiazol-2-yl)-methyl]-7-bromo-1,2,3,4-tetrahydro-cyclopenta[b]indole (from example 121) was prepared (RS,SR)-2-[-benzenesulfonyl-fluoro-(5-methyl-[1,3,4]oxadiazol-2-yl)-methyl]-7-bromo-2,3-dihydro-1H-cyclopenta[b]indole-4-carboxylic acid tert-butyl ester as light brown foam, MS: 589 (M, 1Br).

122.2

Analogously to example 98.2, from (RS,SR)-2-[-benzenesulfonyl-fluoro-(5-methyl-[1,3,4]oxadiazol-2-yl)-methyl]-7-bromo-2,3-dihydro-1H-cyclopenta[b]indole-4-carboxylic acid tert-butyl ester and piperidine was prepared (RS,SR)-2-[benzenesulfonyl-fluoro-(5-methyl-[1,3,4 ]oxadiazol-2-yl)-methyl]-7-piperidin-1-yl-2,3-dihydro-1H-cyclopenta[b]indole-4-carboxylic acid tert-butyl ester as light orange foam, MS: 595 ($MH^+$).

122.3

Analogously to example 98.3, from (RS,SR)-2-[-benzenesulfonyl-fluoro-(5-methyl-[1,3,4 ]oxadiazol-2-yl)-methyl]-7-piperidin-1-yl-2,3-dihydro-1H-cyclopenta[b]indole-4-carboxylic acid tert-butyl ester was prepared (RS,SR)-2-[-benzenesulfonyl-fluoro-(5-methyl-[1,3,4]oxadiazol-2-yl)-methyl]-7-piperidin-1-yl-1,2,3,4-tetrahydro-cyclopenta[b]indole as colorless semisolid, MS: 494 (M).

Example 123

(RS,SR)-N-{2-[-benzenesulfonyl-fluoro-(5-methyl-[1,3,4]oxadiazol-2-yl)-methyl]-1,2,3,4-tetrahydro-cyclopenta[b]indol-7-yl}-N-methyl-amine 123.1

Analogously to example 98.2, from (RS,SR)-2-[-benzenesulfonyl-fluoro-(5-methyl-[1,3,4]oxadiazol-2-yl)-methyl]-7-bromo-2,3-dihydro-1H-cyclopenta[b]indole-4-carboxylic acid tert-butyl ester (from example 122.1) and methylamine was prepared (RS,SR)-2-[benzenesulfonyl-fluoro-(5-methyl-[1,3,4]oxadiazol-2-yl)-methyl]-7-methylamino-2,3-dihydro-1H-cyclopenta[b]indole-4-carboxylic acid tert-butyl ester, MS: 541 ($MH^+$).

123.2

Analogously to example 98.3, from (RS,SR)-2-[-benzenesulfonyl-fluoro-(5-methyl-[1,3,4]oxadiazol-2-yl)-methyl]-7-methylamino-2,3-dihydro-1H-cyclopenta[b]indole-4-carboxylic acid tert-butyl ester was prepared (RS,SR)-N-{2-[-benzenesulfonyl-fluoro-(5-methyl-[1,3,4]oxadiazol-2-yl)-methyl]-1,2,3,4-tetrahydro-cyclopenta[b]indol-7-yl}-N-methyl-amine as light yellow oil, MS: 441 ($MH^+$).

Example 124

2-[benzenesulfonyl-fluoro-(5-trifluoromethyl-[1,3,4] oxadiazol-2-yl)-methyl]-7-chloro-1,2,3,4-tetrahydro-cyclopenta[b]indole 124.1
Analogously to example 74.2 and 74.3, from benzenesulfonyl-acetic acid hydrazide (from example 74.1) and TFA was prepared 2-benzenesulfonylmethyl-5-trifluoromethyl-[1,3,4]oxadiazole as pink crystalline material, MS: 293 (MH$^+$).

124.2
At 0° C. 170 mg (0.5 mmol, 0.2 eq) of $Cs_2CO_3$ were added to a stirred solution of 760 mg (2.6 mmol) of 2-benzenesulfonylmethyl-5-trifluoromethyl-[1,3,4]oxadiazole in 30 mL of THF. After 45 min, 0.23 mL (2.9 mmol) of 2-cyclopenten-1-one were added. The reaction mixture was stirred at RT for 15 hours, diluted with saturated aqueous $NH_4Cl$ and extracted with EtOAc. The combined organic phases were dried over $Na_2SO_4$, filtered and evaporated. Column chromatography on silica gel with heptane/EtOAc 1:1 yielded 0.88 mg (90%) of 3-[benzenesulfonyl-(5-trifluoromethyl-[1,3,4]oxadiazol-2-yl)-methyl]-cyclopentanone as colorless foam, 375 (MH$^+$).

124.3
In analogy to example 12.1, from 3-[benzenesulfonyl-(5-trifluoromethyl-[1,3,4]oxadiazol-2-yl)-methyl]-cyclopentanone at −20° C. was prepared 3-[benzenesulfonyl-fluoro-(5-trifluoromethyl-[1,3,4]oxadiazol-2-yl)-methyl]-cyclopentanone as white solid, MS: 393 (MH$^+$)

124.4
In analogy to example 74.6, from 3-[benzenesulfonyl-fluoro-(5-trifluoromethyl-[1,3,4]oxadiazol-2-yl)-methyl]-cyclopentanone and (4-chloro-phenyl)-hydrazine hydrochloride was prepared a racemic mixture of diastereomers of 2-[benzenesulfonyl-fluoro-(5-trifluoromethyl-[1,3,4]oxadiazol-2-yl)-methyl]-7-chloro-1,2,3,4-tetrahydro-cyclopenta[b]indole as brown oil, MS: 500 (MH, 1Cl)$^+$.

Example 125

(RS,SR)-2-(1-benzenesulfonyl-2-methoxy-1-methyl-ethyl)-7-chloro-1,2,3,4-tetrahydro-cyclopenta[b]indole 125.1
In analogy to example 19.3, from (RS,SR)-2-benzenesulfonyl-2-(3-oxo-cyclopentyl)-propionic acid methyl ester and (4-chloro-phenyl)-hydrazine hydrochloride was prepared (RS,SR)-2-benzenesulfonyl-2-(7-chloro-1,2,3,4-tetrahydro-cyclopenta[b]indol-2-yl)-propionic acid methyl ester as a light brown solid.

125.2
130 mg (0.31 mmol) (RS,SR)-2-benzenesulfonyl-2-(7-chloro-1,2,3,4-tetrahydro-cyclopenta[b]indol-2-yl)-propionic acid methyl ester were dissolved in 7 mL $CH_2Cl_2$ at RT. 90 μL (0.62 mmol, 2 eq) triethylamine, 4 mg (0.031 mmol, 0.1 eq) DMAP and 81 mg (0.37 mmol, 1.2 eq) $BOC_2O$ were added. The reaction mixture was stirred for 2 hours. The reaction was quenched with 10 mL of an aqueous 1M solution of HCl. The organic layer was separated and the aquous layer was washed with $CH_2Cl_2$. The combined organic layers were dried over $Na_2SO_4$, filtered and evaporated to dryness to yield to 152 mg (94%) (RS,SR)-2-(1-benzenesulfonyl-1-methoxycarbonyl-ethyl)-7-chloro-2,3-dihydro-1H-cyclopenta[b]indole-4-carboxylic acid tert-butyl ester as a white powder, M: 535 ($MNH_4^+$).

125.3
152 mg (0.29 mmol) (RS,SR)-2-(1-benzenesulfonyl-1-methoxycarbonyl-ethyl)-7-chloro-2,3-dihydro-1H-cyclopenta[b]indole-4-carboxylic acid tert-butyl ester were dissolved in 3 mL dry THF at RT. 0.32 mL (0.32 mmol, 1.1 eq) of $LiAlH_4$ (1M in THF) were added dropwise. The reaction mixture was stirred for 1 hour and 40 minutes. The reaction was quenched with a saturated $NaHCO_3$ solution. The organic phase was washed with brine, dried over $Na_2SO_4$, filtered and evaporated. Column chromatography on silica gel (EtOAc/heptane 1:2) yielded 50 mg (35%) (RS,SR)-2-(1-benzenesulfonyl-2-hydroxy-1-methyl-ethyl)-7-chloro-2,3-dihydro-1H-cyclopenta[b]indole-4-carboxylic acid tert-butyl ester as a white powder.

125.4
50 mg (0.1 mmol) (RS,SR)-2-(1-benzenesulfonyl-2-hydroxy-1-methyl-ethyl)-7-chloro-2,3-dihydro-1H-cyclopenta[b]indole-4-carboxylic acid tert-butyl ester were dissolved in 5 mL dry THF at 0° C. 5 mg (0.11 mmol, 1.1 eq) NaH (55%) were added and the reaction mixture was stirred for 20 minutes. 10 μL (0.15 mmol, 1.5 eq) methyliodide were then added and the reaction was stirred for 1 hour at 0° C. The reaction was quenched with a saturated $NaHCO_3$ solution. The organic phase was washed with brine, dried over $Na_2SO_4$, filtered and evaporated to dryness to yield 52 mg (100%) (RS,SR)-2-(1-benzenesulfonyl-2-methoxy-1-methyl-ethyl)-7-chloro-2,3-dihydro-1H-cyclopenta[b]indole-4-carboxylic acid tert-butyl ester as a white powder.

125.5
52 mg (0.1 mmol) (RS,SR)-2-(1-benzenesulfonyl-2-methoxy-1-methyl-ethyl)-7-chloro-2,3-dihydro-1H-cyclopenta[b]indole-4-carboxylic acid tert-butyl ester were dissolved in 4 mL $CH_2Cl_2$ at 0° C. Then, 1 mL of TFA was added dropwise and the temperature was slowly raised to RT and the reaction was stirred for 20 minutes. The reaction was quenched with a saturated $NaHCO_3$ solution. The organic phase was dried over $Na_2SO_4$, filtered and evaporated. Column chromatography on silica gel (EtOAc/heptane 1:2) yielded 11 mg (26%) (RS,SR)-2-(1-benzenesulfonyl-2-methoxy-1-methyl-ethyl)-7-chloro-1,2,3,4-tetrahydro-cyclopenta[b]indole as a white powder, MS: 404 (MH$^1$).

Example 126

(RS,SR)-2-benzenesulfonyl-2-(6-chloro-2,3,4,9-tetrahydro-1H-carbazol-2-yl)-2-fluoro-N-methyl-N-(3-methyl-but-2-enyl)-acetamide 126.1
In analogy to example 1.1, from methylphenylsulfonylacetate and cyclohexen-1-one was prepared benzenesulfonyl-(3-oxo-cyclohexyl)-acetic acid methyl ester as a racemic mixture of diastereomers, light yellow oil, MS: 311 (MH$^+$).

126.2
In analogy to example 74.5, from benzenesulfonyl-(3-oxo-cyclohexyl)-acetic acid methyl ester and N-fluorobenzensulfonimide was prepared (RS,SR) benzenesulfonyl-fluoro-(-3-oxo-cyclohexyl)-acetic acid methyl ester as an yellow oil, MS: 346 ($MNH_4^+$).

126.3
In analogy to example 19.3, from (RS,SR)-benzenesulfonyl-fluoro-(-3-oxo-cyclohexyl)-acetic acid methyl ester and 4-chlorophenylhydrazine hydrochloride was prepared (RS,SR)-benzenesulfonyl-(6-chloro-2,3,4,9-tetrahydro-1H-carbazol-2-yl)-fluoro-acetic acid methyl ester as an orange solid.

126.4

In analogy to example 55, from (RS,SR)-benzenesulfonyl-(6-chloro-2,3,4,9-tetrahydro-1H-carbazol-2-yl)-fluoro-acetic acid methyl ester and methylamine was prepared (RS,SR)-2-benzenesulfonyl-2-(6-chloro-2,3,4,9-tetrahydro-1H-carbazol-2-yl)-2-fluoro-N-methyl-acetamide as a white solid, MS: 435 (MH$^+$).

126.5

0.924 g (0.002 mol) of (RS, SR)-2-benzenesulfonyl-2-(6-chloro-2,3,4,9-tetrahydro-1H-carbazol-2-yl)-2-fluoro-N-methyl-acetamide were dissolved in 20 mL CH$_2$Cl$_2$ at RT. Then, 0.59 mL triethylamine (0.004 mol, 2 eq), 26 mg DMAP (0.2 mmol, 0.1 eq) and 0.556 g BOC$_2$O (0.003 mol, 1.2 eq) were added. The reaction mixture was stirred for 2H30. The reaction was quenched with a saturated NH$_4$Cl aqueous solution, and the product extracted with CH$_2$Cl$_2$. The combined organic phases were dried on Na$_2$SO$_4$, filtered and evaporated. The crude material was precipitated in diethyl ether. The solvent was removed and the remaining solid was dried under vaccum to yield to 0.840 g (74%) of (RS, SR)-2-(benzenesulfonyl-fluoro-methylcarbamoyl-methyl)-6-chloro-1,2,3,4-tetrahydro-carbazole-9-carboxylic acid tert-butyl ester as a white solid, MS: 552 (MNH$_4^+$).

126.6

To a stirred solution of 60 mg (0.11 mmol) of (RS,SR)-2-(benzenesulfonyl-fluoro-methylcarbamoyl-methyl)-6-chloro-1,2,3,4-tetrahydro-carbazole-9-carboxylic acid tert-butyl ester in 3 mL THF was added on 7 mg NaH (60% in oil, 0.165 mmol, 1.5 eq) at 0° C. The reaction mixture was stirred for 40 minutes and then, 52 µL (0.22 mmol, 2 eq) 1-bromo-3-methyl-but-2-ene (1 mL in THF) was added and the reaction mixture was stirred for 2 hours at 0° C. and then overnight at RT. The solvent was evaporated. Then, 1 mL CH$_2$Cl$_2$ was added and after dissolution, 1 mL TFA and 1 mL CH$_2$Cl$_2$ were added at RT. The reaction mixture was stirred overnight. The solvent was then evaporated and purification by prep. HPLC gave 9 mg (19%) of (RS,SR)-2-benzenesulfonyl-2-(-6-chloro-2,3,4,9-tetrahydro-1H-carbazol-2-yl)-2-fluoro-N-methyl-N-(3-methyl-but-2-enyl)-acetamide as a white solid, MS: 503 (MH$^+$).

Example 127

(RS,SR)-5-[benzenesulfonyl-(7-chloro-1,2,3,4-tetrahydro-cyclopenta[b]indol-2-yl)-fluoro-methyl]-[1,2,4]oxadiazole-3-carbonitrile 127.1

In analogy to example 82.1, from nitriloacetic acid methyl ester and hydroxylamine hydrochloride was prepared amino-hydroxyimino-acetic acid methyl ester as a white solid.

127.2

In analogy to example 82.2, from amino-hydroxyimino-acetic acid methyl ester and phenylsulfanyl-acetyl chloride was prepared 5-phenylsulfanylmethyl-[1,2,4]oxadiazole-3-carboxylic acid methyl ester as an yellow oil, MS: 521 (MH$^+$).

127.3

In analogy to example 81.3, from 5-phenylsulfanylmethyl-[1,2,4]oxadiazole-3-carboxylic acid methyl ester and mCPBA was prepared 5-benzenesulfonylmethyl-[1,2,4]oxadiazole-3-carboxylic acid methyl ester as a white solid, MS: 282 (MH$^+$).

127.4

In analogy to example 74.4, from 5-benzenesulfonylmethyl-[1,2,4]oxadiazole-3-carboxylic acid methyl ester and cyclopent-2-enone was prepared 5-[benzenesulfonyl-(3-oxo-cyclopentyl)-methyl]-[1,2,4]oxadiazole-3-carboxylic acid methyl ester as a racemic mixture of diastereomers, colorless oil, MS: 382 (MNH$_4^+$).

127.5

In analogy to example 74.5, from 5-[benzenesulfonyl-(3-oxo-cyclopentyl)-methyl]-[1,2,4]oxadiazole-3-carboxylic acid methyl ester and N-fluorobenzenesulfonimide were prepared (RS,SR)-5-[benzenesulfonyl-fluoro-(3-oxo-cyclopentyl)-methyl]-[1,2,4]oxadiazole-3-carboxylic acid methyl ester as a white solid, MS: 400 (MNH$_4^+$) and (RR,SS)-5-[benzenesulfonyl-fluoro-(3-oxo-cyclopentyl)-methyl]-[1,2,4]oxadiazole-3-carboxylic acid methyl ester as a white solid, MS: 400 (MNH$_4^+$).

127.6

In analogy to example 19.3, from (RS,SR)-5-[benzenesulfonyl-fluoro-(3-oxo-cyclopentyl)-methyl]-[1,2,4]oxadiazole-3-carboxylic acid methyl ester and (4-chloro-phenyl)-hydrazine hydrochloride was prepared (RS,SR)-5-[benzenesulfonyl-(7-chloro-1,2,3,4-tetrahydro-cyclopenta[b]indol-2-yl)-fluoro-methyl]-[1,2,4]oxadiazole-3-carboxylic acid methyl ester as a light orange solid, MS: 490 (MH$^+$).

127.7

In analogy to example 85, from (RS, SR)-5-[benzenesulfonyl-(7-chloro-1,2,3,4-tetrahydro-cyclopenta[b]indol-2-yl)-fluoro-methyl]-[1,2,4]oxadiazole-3-carboxylic acid methyl ester and ammonium hydroxide solution (25% in water) was prepared (RS,SR)-5-[benzenesulfonyl-(7-chloro-1,2,3,4-tetrahydro-cyclopenta[b]indol-2-yl)-fluoro-methyl]-[1,2,4]oxadiazole-3-carboxylic acid amide, as a yellow oil, MS: 475 (MH$^+$).

127.8

To a stirred solution of 170 mg (0.35 mmol) of (RS,SR)-5-[benzenesulfonyl-(7-chloro-1,2,3,4-tetrahydro-cyclopenta[b]indol-2-yl)-fluoro-methyl]-[1,2,4]oxadiazole-3-carboxylic acid amide in 2 mL acetonitrile at RT was added 0.5 mL phosphorous oxychloride. The dark brown solution was stirred for 1 hour and then the temperature was raised to 50° C. and stirred overnight. After cooling down to RT, 0.5 mL phosphorous oxychloride were added. The reaction mixture was stirred for 2 hours under reflux condition. The solvent was partially evaporated and the resulting oil was dissolved with EtOAc and washed with saturated NaHCO$_3$ solution. The organic phase was dried over Na$_2$SO$_4$, filtered and evaporated. Column chromatography on silica gel (EtOAc/heptane 1:1) yielded 20 mg (12%) of (RS, SR)-5-[benzenesulfonyl-(7-chloro-1,2,3,4-tetrahydro-cyclopenta[b]indol-2-yl)-fluoro-methyl]-[1,2,4]oxadiazole-3-carbonitrile as a light red solid, MS: 457 (MH$^+$).

Example 128

(RS,SR)-{5-[benzenesulfonyl-(6-chloro-2,3,4,9-tetrahydro-1H-carbazol-2-yl)-fluoro-methyl]-[1,2,4]oxadiazol-3-yl}-dimethyl-amine 128.1

To a stirred solution of 20.4 g (0.285 mol) of dimethylcyanamide in 500 mL of MeOH at RT, was added 19.820 g (0.285 mol, 1 eq) hydroxylamine and then 52.82 mL (0.285 mol, 1 eq) sodium methylate were slowly added (exothermic reaction). The reaction mixture was stirred overnight. The mixture was filtered in order to remove the salt, MeOH was evaporated and the mixture was diluted with chloroform. The precipitate was filtered off and the filtrate was evaporated to dryness to yield to 29.4 g (95%) of 3-hydroxy-1,1-dimethyl-guanidine as an orange oil.

128.2

In analogy to example 81.1, from phenylthiol and bromomethylethyl ester was prepared phenylsulfanyl-acetic acid ethyl ester as a colorless oil, MS: 197 (MH$^+$).

128.3

To a stirred suspension of 14 g (0.129 mol, 1.4 eq) of 3-hydroxy-1,1-dimethyl-guanidine in 300 mL dry THF at 0° C. was added portionwise 6.191 g (0.155 mol, 1.2 eq) of NaH (60% in oil). The resulting heavy suspension was stirred at RT for 1 hour 30 minutes. Then, 28.126 g (0.129 mol) phenylsulfanyl-acetic acid ethyl ester were slowly added. The reaction mixture was stirred at RT for 2 hours and then at 65° C. for 1 hour. The reaction was quenched by addition of a saturated aqueous solution of NH$_4$Cl and the product extracted with EtOAc. The combined organic phase was dried on Na$_2$SO$_4$, filtered and evaporated. Column chromatography on silica gel (EtOAc/heptane, 1:9 to 1:2) yielded 19.370 g (64%) dimethyl-(5-phenylsulfanylmethyl-[1,2,4]oxadiazol-3-yl)-amine as a colorless oil, MS: 236 (MH$^+$).

128.4

In analogy to example 81.3, from dimethyl-(5-phenylsulfanylmethyl-[1,2,4]oxadiazol-3-yl)-amine and mCPBA was prepared (5-benzenesulfonylmethyl-[1,2,4]oxadiazol-3-yl)-dimethyl-amine as a white solid, MS: 268 (MH$^+$).

128.5

In analogy to example 74.4, from (5-benzenesulfonylmethyl-[1,2,4]oxadiazol-3-yl)-dimethyl-amine and 2-cyclohexen-1-one was prepared 3-[benzenesulfonyl-(3-dimethylamino-[1,2,4]oxadiazol-5-yl)-methyl]-cyclohexanone as a racemic mixture of diastereomers, light brown solid, MS: 364 (MNH$_4^+$).

128.6

In analogy to example 74.5, from 3-[benzenesulfonyl-(3-dimethylamino-[1,2,4]oxadiazol-5-yl)-methyl]-cyclohexanone and N-fluorobenzenesulfonimide was prepared (RR,SS)-3-[benzenesulfonyl-(3-dimethylamino-[1,2,4]oxadiazol-5-yl)-fluoro-methyl]-cyclohexanone as a colorless oil, MS:382 (MH$^+$) and (RS,SR)-3-[benzenesulfonyl-(3-dimethylamino-[1,2,4]oxadiazol-5-yl)-fluoro-methylcyclohexanone as a colorless oil, MS: 382 (MH$^+$).

128.7

In analogy to example 19.3, from (RS,SR)-3-[benzenesulfonyl-(3-dimethylamino-[1,2,4]oxadiazol-5-yl)-fluoro-methyl]-cyclohexanone and (4-chloro-phenyl)-hydrazine hydrochloride was prepared (RS,SR)-{5-[benzenesulfonyl-(6-chloro-2,3,4,9-tetrahydro-1H-carbazol-2-yl)-fluoro-methyl]-[1,2,4]oxadiazol-3-yl}-dimethyl-amine as a light yellow solid, MS: 489 (MH$^+$).

Example 129

(RS,SR)-4-[({5-[-benzenesulfonyl-(7-chloro-1,2,3,4-tetrahydro-cyclopenta[b]indol-2-yl)-fluoro-methyl]-[1,2,4]oxadiazol-3-ylmethyl}-amino)-methyl]-benzoic acid methyl ester 129.1

In analogy to example 89.7, from (RS,SR)-2-{5-[benzenesulfonyl-fluoro-(3-oxo-cyclopentyl)-methyl]-[1,2,4]oxadiazol-3-ylmethyl}-isoindole-1,3-dione (example 89.6) and (4-chloro-phenyl)-hydrazine hydrochloride was prepared (RS,SR)-2-{5-[benzenesulfonyl-(7-chloro-1,2,3,4-tetrahydro-cyclopenta[b]indol-2-yl)-fluoro-methyl]-[1,2,4]oxadiazol-3-ylmethyl}-isoindole-1,3-dione as a light yellow powder, MS: 608 (MNH$_4^+$).

129.2

To a suspension of 420 mg (0.7 mmol) of (RS,SR)-2-{5-[benzenesulfonyl-(7-chloro-1,2,3,4-tetrahydro-cyclopenta[b]indol-2-yl)-fluoro-methyl]-[1,2,4]oxadiazol-3-ylmethyl}-isoindole-1,3-dione in 50 mL EtOH at RT, was added 0.1 mL (2.1 mmol, 3 eq) hydrazine. The reaction mixture was heated at 80° C. over 3 hours 30 minutes. After cooling down, the reaction was quenched with a 1M solution of HCl, and extracted with EtOAc. The combined organic phases were dried over Na$_2$SO$_4$, filtered and evaporated. Column chromatography on silica gel (CH$_2$Cl$_2$/MeOH 95/5) yielded 210 mg (64%) of (RS,SR)-C-{5-[benzenesulfonyl-(7-chloro-1,2,3,4-tetrahydro-cyclopenta[b]indol-2-yl)-fluoro-methyl]-[1,2,4]oxadiazol-3-yl}-methylamine as a light brown powder, MS: 461 (MH$^+$).

129.3

To a stirred solution of 50 mg (0.1 mmol) of (RS,SR)-C-{5-[benzenesulfonyl-(7-chloro-1,2,3,4-tetrahydro-cyclopenta[b]indol-2-yl)-fluoro-methyl]-[1,2,4]oxadiazol-3-yl}-methylamine in 5 mL MeOH at 0° C. was added 19 mg (0.1 mmol, 1 eq) of methyl 4-formylbenzoate, 7 mg (0.1 mmol, leg) sodium cyanoborohydride and one drop of acetic acid. The reaction mixture was stirred at 0° C. for 20 minutes and then the temperature was raised to RT and the reaction quenched with saturated aqueous solution of NaHCO$_3$. The reaction mixture was poured on water and extracted with EtOAc. The organic phase were dried over Na$_2$SO$_4$, filtered and evaporated. Column chromatography on silica gel (heptane/EtOAc 1:1) yielded 30 mg (45%) of (RS,SR)-4-[({5-[benzenesulfonyl-(7-chloro-1,2,3,4-tetrahydro-cyclopenta[b]indol-2-yl)-fluoro-methyl]-[1,2,4]oxadiazol-3-ylmethyl}-amino)-methyl]-benzoic acid methyl ester as a light yellow powder, MS: 609 (MH$^+$).

Example 130

(RS,SR)-3-[({5-[benzenesulfonyl-(7-chloro-1,2,3,4-tetrahydro-cyclopenta[b]indol-2-yl)-fluoro-methyl]-[1,2,4]oxadiazol-3-ylmethyl}-amino)-methyl]-benzoic acid methyl ester In analogy to example 129.3, from (RS,SR)-C-{5-[benzenesulfonyl-(7-chloro-1,2,3,4-tetrahydro-cyclopenta[b]indol-2-yl)-fluoro-methyl]-[1,2,4]oxadiazol-3-yl}-methylamine and methyl-3-formylbenzoate was prepared (RS,SR)-3-[{5-[benzenesulfonyl-(7-chloro-1,2,3,4-tetrahydro-cyclopenta[b]indol-2-yl)-fluoro-methyl]-[1,2,4]oxadiazol-3-ylmethyl}-amino)-methyl]-benzoic acid methyl ester as a light yellow powder, MS: 609 (MH$^+$).

Example 131

(RS,SR)-{4-[({5-[benzenesulfonyl-(7-chloro-1,2,3,4-tetrahydro-cyclopenta[b]indol-2-yl)-fluoro-methyl]-[1,2,4]oxadiazol-3-ylmethyl}-amino)-methyl]-phenyl}-methanol To a stirred solution of 27 mg (0.04 mmol) of (RS,SR)-4-[({5-[-benzenesulfonyl-(-7-chloro-1,2,3,4-tetrahydro-cyclopenta[b]indol-2-yl)-fluoro-methyl]-[1,2,4]oxadiazol-3-ylmethyl}-amino)-methyl]-benzoic acid methyl ester (example 129.3) in 2 mL THF at 0° C., 40 µl (0.04 mmol, 1 eq) lithium aluminum hydride (1M solution in THF) were added. The reaction mixture was stirred at 0° C. for 1 hour and then at RT for 30 minutes. The reaction was quenched with a saturated NaHCO$_3$ aqueous solution, and the crude product extracted with EtOAc. The combined organic phases were dried over

83

Na$_2$SO$_4$, filtered and evaporated. Column chromatography on silica gel (heptane/EtOAc 2:8) yielded 12 mg (48%) of (RS,SR)-{4-[{5-[benzenesulfonyl-(7-chloro-1,2,3,4-tetrahydro-cyclopenta[b]indol-2-yl)-fluoro-methyl]-[1,2,4]oxadiazol-3-ylmethyl}-amino)-methyl]-phenyl}-methanol as a light yellow powder, MS: 581 (MH$^+$).

Example 132

(RS,SR)-2-(benzenesulfonyl-pyridin-2-yl-methyl)-7-chloro-1,2,3,4-tetrahydro-cyclopenta[b]indole 132.1
To a stirred suspension of 2.5 g (0.010 mol) of 2-bromomethyl-pyridine hydrobromide in 10 mL of CH$_3$CN at RT, was added 1.78 mL (0.0105 mol, 1.05 eq.) of Hunig's base. After complete dissolution of the salt, 1.62 g (0.010 mol, 1 eq.) of sodium benzene sulfinat and 0.52 g (0.002 mol, 0.2 eq.) were added. The mixture was stirred at RT for 48 hours, and then the reaction was quenched by addition of water, and the product extracted with EtOAc. The combined organic phases were dried over Na$_2$SO$_4$, filtered and dried under vacuum to afford 1.86 g (80%) of 2-benzenesulfonylmethyl-pyridine.

132.2
In analogy to example 74.4, from 2-benzenesulfonylmethyl-pyridine and cyclopenten-2-one was prepared 3-(benzenesulfonyl-pyridin-2-yl-methyl)-cyclopentanone as a racemic mixture of diastereomeres.

132.3
In analogy to example 19.3, from 3-(benzenesulfonyl-pyridin-2-yl-methyl)-cyclopentanone and (4-chloro-phenyl)-hydrazine hydrochloride was prepared (RR, SS)-2-(benzenesulfonyl-pyridin-2-yl-methyl)-7-chloro-1,2,3,4-tetrahydro-cyclopenta[b]indole and (RS, SR)-2-(benzenesulfonyl-pyridin-2-yl-methyl)-7-chloro-1,2,3,4-tetrahydro-cyclopenta[b]indole as a white solid, MS: 423 (MH$^+$).

Example 133

(RS,SR)-N-{5-[benzenesulfonyl-(7-chloro-1,2,3,4-tetrahydro-cyclopenta[b]indol-2-yl)-fluoro-methyl]-[1,2,4]oxadiazol-3-ylmethyl}-2,2,2-trifluoro-acetamide 133.1
In analogy to example 129.2, from (RS,SR)-2-{5-[benzenesulfonyl-(7-chloro-1,2,3,4-tetrahydro-cyclopenta[b]indol-2-yl)-fluoro-methyl]-[1,2,4]oxadiazol-3-ylmethyl}-isoindole-1,3-dione (example 129.1) and hydrazine was prepared (RS,SR)-C-{5-[benzenesulfonyl-(7-chloro-1,2,3,4-tetrahydro-cyclopenta[b]indol-2-yl)-fluoro-methyl]-[1,2,4]oxadiazol-3-yl}-methylamine as a light brown powder, MS: 461 (MH$^+$).

133.2
To a stirred solution of 46 mg (0.1 mmol) of (RS,SR)-C-{5-[benzenesulfonyl-(7-chloro-1,2,3,4-tetrahydro-cyclopenta[b]indol-2-yl)-fluoro-methyl]-[1,2,4]oxadiazol-3-yl}-methylamine in 3 mL CH$_2$Cl$_2$ at RT, was added 10 μl (0.1 mmol, 1 eq) trifluoroacetic acid and 80 μl pyridine (1 mmol, 10 eq). Stirring was continued overnight, and the reaction mixture was evaporated to dryness. Column chromatography on silica gel (heptane/EtOAc 6:4) yielded 6 mg (12%) of (RS,SR)-N-{5-[benzenesulfonyl-(7-chloro-1,2,3,4-tetrahydro-cyclopenta[b]indol-2-yl)-fluoro-methyl]-[1,2,4]oxadiazol-3-ylmethyl}-2,2,2-trifluoro-acetamide as a light yellow powder, MS: 557 (MH$^+$).

84

Example 134

2-[benzenesulfonyl-fluoro-(3-phenyl-[1,2,4]oxadiazol-5-yl)-methyl]-7-chloro-1,2,3,4-tetrahydro-cyclopenta[b]indole 134.1
From N-hydroxy-benzamidine and chloro acetyl chloride [described in Heterocycles, 26(1), 163-73, 1987] was prepared 5-chloromethyl-3-phenyl-[1,2,4]oxadiazole.

134.2
To a stirred solution of 525 mg (2.7 mmol) of 5-chloromethyl-3-phenyl-[1,2,4]oxadiazole in acetonitrile at RT, 465 mg (2.8 mmol, 1.05 eq) of sodium benzenesulfinate and 143 mg (0.5 mmol, 0.2 eq) of 18-crown-6 were added. Stirring was continued overnight, and an additional 50 mg (0.3 mmol, 0.12 eq) of sodium benzenesulfinate were added and the reaction mixture was allowed to stirr for one further hour. The solvent was evaporated and the resulting oil was taken up in EtOAc, washed with a saturated NaHCO$_3$ solution. The organic phase was dried over Na$_2$SO$_4$, filtered and evaporated. Column chromatography on silica gel (heptane/EtOAc 8:2) yielded 622 mg (77%) of 5-benzenesulfonylmethyl-3-phenyl-[1,2,4]oxadiazole as a white solid, MS: 301 (MH$^+$).

134.3
In analogy to example 74.4, from 5-benzenesulfonylmethyl-3-phenyl-[1,2,4]oxadiazole and cyclopenten-2-one was prepared 3-[benzenesulfonyl-(3-phenyl-[1,2,4]oxadiazol-5-yl)-methyl]-cyclopentanone as a racemic mixture of diastereoisomers, white solid, MS: 400 (MNH$_4^+$).

134.4
In analogy to example 74.5, from 3-[benzenesulfonyl-(3-phenyl-[1,2,4]oxadiazol-5-yl)-methyl]-cyclopentanone and N-fluorobenzensulfonimide was prepared 3-[benzenesulfonyl-fluoro-(3-phenyl-[1,2,4]oxadiazol-5-yl)-methyl]-cyclopentanone as an off-white viscous oil, MS: 401 (MH$^+$).

134.5
In analogy to example 19.3, from 3-[benzenesulfonyl-fluoro-(3-phenyl-[1,2,4]oxadiazol-5-yl)-methyl]-cyclopentanone and (4-chloro-phenyl)-hydrazine hydrochloride was prepared 2-[benzenesulfonyl-fluoro-(3-phenyl-[1,2,4]oxadiazol-5-yl)-methyl]-7-chloro-1,2,3,4-tetrahydro-cyclopenta[b]indole as a brown solid, MS: 508 (MH$^+$).

Example 135

(RS,SR)-2-[benzenesulfonyl-(7-chloro-1,2,3,4-tetrahydro-cyclopenta[b]indol-2-yl)-fluoro-methyl]-oxazole-4-carboxylic acid methyl ester 135.1
17.140 g (0.123 mol) of aminoacetic acid ethyl ester hydrochloride and 15.175 g (0.123 mol, 1 eq) of acetimidic acid ethyl ester hydrochloride were stirred in solution in 300 mL ice cold water. 200 mL diethyl ether and then 16.97 g (0.123 mol, 1 eq) K$_2$CO$_3$ were added. The reaction mixture was stirred for 10 minutes. The organic phase was separated and dried over Na$_2$SO$_4$, filtered and evaporated to dryness to yield to 15.229 g (72%) of (1-ethoxy-ethylideneamino)-acetic acid ethyl ester as a light yellow oil.

135.2
To a stirred suspension of 3.222 g (36 mmol, 1.05 eq) of potassium ethoxide in 30 mL diethyl ether and 5 mL EtOH at 0° C., a solution of 3.849 g (52 mmol, 1.5 eq) ethyl formate and 6 g (35 mmol) (1-ethoxy-ethylideneamino)-acetic acid ethyl ester in 30 mL diethyl ether and 5 mL EtOH is then slowly added. The reaction mixture is stirred for one hour at 0° C. After addition of 40 mL diethyl ether, the reaction mixture was stirred at RT overnight. The reaction mixture was filtered and the obtained solid was washed with diethyl ether and dried under vaccum to yielded 5 g (60%) of potassium 2-ethoxycarbonyl-2-(1-ethoxy-ethylideneamino)-ethenolate as an orange solids.

135.3

5 g (25 mmol) of potassium 2-ethoxycarbonyl-2-(1-ethoxy-ethylideneamino)-ethenolate were completely dissolved in 15 mL acetic acid at RT, and then the solution was heated to 110° C. overnight. After cooling down, 100 mL EtOAc were added and the solution is neutralized with saturated $NaHCO_3$ solution. The organic phase was separated, dried over $Na_2SO_4$, filtered and evaporated. Column chromatography on silica gel (heptane/EtOAc 1:2) yielded 1.74 g (45%) of 2-methyl-oxazole-4-carboxylic acid ethyl ester as an yellow oil, MS: 156 ($MH^+$).

135.4

To a stirred solution of 1.74 g (11 mmol) of 2-methyl-oxazole-4-carboxylic acid ethyl ester in 15 mL tetrachloromethane at RT, 2.994 g (17 mmol, 1.5 eq) N-bromosuccinimide and 50 mg (0.2 mmol, 0.02 eq) benzoyl peroxyde were added. The reaction mixture was stirred under reflux overnight. The reaction mixture was filtered, the filtrate was extracted with $CH_2Cl_2$ and $Na_2S_2O_3$ solution. The combined organic phases were dried over $Na_2SO_4$, filtered and evaporated to dryness to yield 265 mg (10%) of 2-bromomethyl-oxazole-4-carboxylic acid ethyl ester as an yellow oil, MS: 235 ($MH^+$).

135.5

In analogy to example 134.2, from 2-bromomethyl-oxazole-4-carboxylic acid ethyl ester and sodium benzosulfinat was prepared 2-benzenesulfonylmethyl-oxazole-4-carboxylic acid ethyl ester as a white solid, MS: 296 ($MH^+$).

135.6

In analogy to example 74.4, from 2-benzenesulfonylmethyl-oxazole-4-carboxylic acid ethyl ester and cyclopenten-2-one was prepared 2-[benzenesulfonyl-(3-oxo-cyclopentyl)-methyl]-oxazole-4-carboxylic acid methyl ester as a racemic mixture of diastereoisomers, as an yellow oil, MS: 364 ($MH^+$).

135.7

In analogy to example 74.5, from 2-[benzenesulfonyl-(3-oxo-cyclopentyl)-methyl]-oxazole-4-carboxylic acid methyl ester and N-fluorobenzensulfonimide was prepared 2-[benzenesulfonyl-fluoro-(3-oxo-cyclopentyl)-methyl]-oxazole-4-carboxylic acid methyl ester as a racemic mixture of diastereoisomers, as a white oil, MS: 382 ($MH^+$).

135.8

In analogy to example 19.3, from 2-[benzenesulfonyl-fluoro-(3-oxo-cyclopentyl)-methyl]-oxazole-4-carboxylic acid methyl ester and (4-chloro-phenyl)-hydrazine hydrochloride was prepared (RS,SR)-2-[benzenesulfonyl-(7-chloro-1,2,3,4-tetrahydro-cyclopenta[b]indol-2-yl)-fluoro-methyl]-oxazole-4-carboxylic acid methyl ester as a brown oil, MS: 489 ($MH^+$).

Example 136

2-(benzenesulfonyl-benzothiazol-2-yl-fluoro-methyl)-7-chloro-1,2,3,4-tetrahydro-cyclopenta[b]indole 136.1

In analogy to example 134.2, from 2-(bromomethyl)-1,3-benzothiazole and sodium benzenesulfinate was prepared 2-benzenesulfonylmethyl-benzothiazole as a crystalline orange solid, MS: 290 ($MH^+$).

136.2

In analogy to example 74.4, from 2-benzenesulfonylmethyl-benzothiazole and cyclopenten-2-one was prepared 3-(benzenesulfonyl-benzothiazol-2-yl-methyl)-cyclopentanone as a racemic mixture of diastereoisomers, as a white powder, MS: 372 ($MH^+$).

136.3

In analogy to example 74.5, from 3-(benzenesulfonyl-benzothiazol-2-yl-methyl)-cyclopentanone and N-fluorobenzensulfonimide was prepared 3-(benzenesulfonyl-benzothiazol-2-yl-fluoro-methyl)-cyclopentanone as a racemic mixture of diastereoisomers, as a yellow foam, MS: 390 ($MH^+$).

136.4

In analogy to example 19.3, from 3-(benzenesulfonyl-benzothiazol-2-yl-fluoro-methyl)-cyclopentanone and (4-chloro-phenyl)-hydrazine hydrochloride was prepared 2-(benzenesulfonyl-benzothiazol-2-yl-fluoro-methyl)-7-chloro-1,2,3,4-tetrahydro-cyclopenta[b]indole as a racemic mixture of diastereoisomers, brown oil, MS: 497 ($MH^+$).

Example 137

(RS,SR)-2-[benzenesulfonyl-(4,5-dimethyl-oxazol-2-yl)-methyl]-7-chloro-1,2,3,4-tetrahydro-cyclopenta[b]indole 137.1

In analogy to example 135.4, from trimethyloxazole was prepared 2-bromomethyl-4,5-dimethyl-oxazole, as a brown oil, MS: 190 ($MH^+$).

137.2

In analogy to example 134.2, from 2-bromomethyl-4,5-dimethyl-oxazole and sodium benzosulfinate was prepared 2-benzenesulfonylmethyl-4,5-dimethyl-oxazole, as a light yellow oil, MS: 364 ($MH^+$).

137.3

In analogy to example 74.4, from 2-benzenesulfonylmethyl-4,5-dimethyl-oxazole and cyclopenten-2-one was prepared 3-[benzenesulfonyl-(4,5-dimethyl-oxazol-2-yl)-methyl]-cyclopentanone as a racemic mixture of diastereoisomers, light yellow oil, MS: 334 ($MH^+$).

137.4

In analogy to example 19.3, from 3-[benzenesulfonyl-(4,5-dimethyl-oxazol-2-yl)-methyl]-cyclopentanone and (4-chloro-phenyl)-hydrazine hydrochloride was prepared (RS, SR)-2-[benzenesulfonyl-(4,5-dimethyl-oxazol-2-yl)-methyl]-7-chloro-1,2,3,4-tetrahydro-cyclopenta[b]indole, as a light yellow oil, MS: 441 ($MH^+$).

Example 138

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |

| Ingredients | Per tablet | |
|---|---|---|
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example 139

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 140

Injection solutions can have the following composition:

| Compound of formula (I) | 3.0 mg |
|---|---|
| Polyethylene glycol 400 | 150.0 mg |
| Acetic acid | q.s. ad pH 5.0 |
| Water for injection solutions | ad 1.0 ml |

The active ingredient is dissolved in a mixture of polyethylene glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

It is to be understood that the invention is not limited to the particular embodiments of the invention described above, as variations of the particular embodiments may be made and still fall within the scope of the appended claims.

The invention claimed is:

1. A compound of the formula (I)

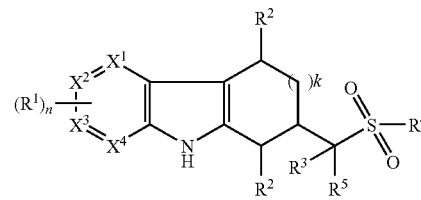

(I)

wherein n is an integer selected from 0 to 3;

$R^1$ is independently selected from the group consisting of halogen, —CN, —$NO_2$, —$SO_2$Me, lower alkyl, trifluoromethoxy, —$OR^{11}$, piperidinyl, pyrrolidinyl, and —$N(R^{11})(R^{11})$, wherein $R^{11}$ is independently selected from lower alkyl and H, $X^1$, $X^2$, $X^3$, and $X^4$ are independently selected from nitrogen and carbon, provided that no more than two of $X^1$, $X^2$, $X^3$, and $X^4$ can be nitrogen at one time, and when two of $X^1$, $X^2$, $X^3$, and $X^4$ are nitrogen, n is 0, 1, or 2;

k is an integer from 0 to 1;

$R^2$ is H;

$R^3$ is H, alkyl, or halogen;

$R^4$ is aryl, heteroaryl, alkylaryl or alkylheteroaryl, all being optionally substituted with from one to five substituents independently selected from the group consisting of halogen, alkyl, —$OR^{41}$, lower alkynyl, and $NR^{42}R^{43}$, wherein $R^{41}$ is lower alkyl or —H, $R^{42}$ and $R^{43}$ independently from each other are hydrogen or alkyl, or $NR^{42}R^{43}$ is piperidinyl or pyrrolidinyl, or $R^4$ is alkyl;

$R^5$ is selected from the group consisting of

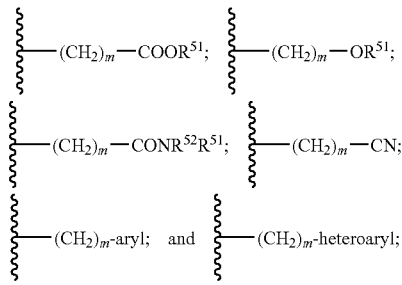

said aryl and heteroaryl being optionally substituted at one or more positions with one or more substituents independently selected from the group consisting of H, halogen, lower alkyl and $(CH_2)_v R^{53}$, wherein $R^{51}$ is selected from the group consisting of H, alkyl, lower alkenyl and alkylaryl, said alkylaryl being optionally substituted at one or more positions with one or more of lower alkyl, —CN, halogen, —$COOR^{54}$, and —$CH_2OR^{54}$, wherein $R^{54}$ is alkyl or —H;

$R^{52}$ is lower alkyl or —H;

$R^{53}$ is H, alkyl, cycloalkyl, —$COOR^{55}$, —$N(R^{55})(R^{56})$, —$CH_2OH$, —CN, $CF_3$, —$CONH_2$, —$CH_2OR^{55}$ or —$CONR^{55}R^{56}$, wherein $R^{55}$ is independently selected from the group consisting of alkyl, —H, —C(O)-aryl, —C(O)-alkyl, or —C(O)-heteroaryl, and $R^{56}$ is selected from the group consisting of H, alkyl, C(O)$CF_3$, —C(O)-aryl, —C(O)-alkyl, —C(O)-heteroaryl, alkylaryl and alkylheteroaryl, and wherein said aryl, heteroaryl, alkylaryl and alkyl-heteroaryl are optionally substituted at one or more positions with one or more of alkyl, —CN, halogen, —COOR$^{57}$, and —CH$_2$OR$^{57}$, wherein R$^{57}$ is lower alkyl or —H, or R$^{55}$ and R$^{56}$ together with the atom to which they are attached form a ring;
or R$^{53}$ is aryl which can optionally be substituted with benzyloxy, carboxy, lower-alkoxy-carbonyl, hydroxy-lower-alkyl, halogen, carbamoyl, lower-alkyl-carbamoyl, di-lower-alkyl-carbamoyl,
m is an integer selected from 0 to 2;
v is an integer selected from 0 to 4;
and pharmaceutically-acceptable salts and/or pharmaceutically-acceptable esters thereof.

2. The compound according to claim 1, wherein
n is an integer selected from 0 to 3;
R$^1$ is independently selected from the group consisting of halogen, —CN, —NO$_2$, —SO$_2$Me, lower alkyl, trifluoromethoxy, —OR$^{11}$, and —N(R$^{11}$)(R$^{11}$), wherein R$^{11}$ is independently selected from lower alkyl and H;
X$^1$, X$^2$, X$^3$, and X$^4$ are independently selected from nitrogen and carbon, provided that no more than two of X$^1$, X$^2$, X$^3$, and X$^4$ can be nitrogen at one time, and when two of X$^1$, X$^2$, X$^3$, and X$^4$ are nitrogen, n is 0, 1, or 2;
k is an integer from 0 to 1;
R$^2$ is H;
R$^3$ is H, alkyl, or halogen;
R$^4$ is aryl, heteroaryl, alkylaryl or alkylheteroaryl, all being optionally substituted with from one to five substituents independently selected from the group consisting of halogen, alkyl and —OR$^{41}$, wherein R$^{41}$ is lower alkyl or —H, or R$^4$ is alkyl;
R$^5$ is selected from the group consisting of

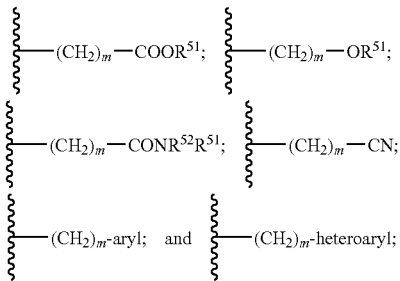

said aryl and heteroaryl being optionally substituted at one or more positions with one or more substituents independently selected from the group consisting of H, halogen, lower alkyl and (CH$_2$)$_v$R$^{53}$, wherein
R$^{51}$ is selected from the group consisting of H, alkyl, allyl and alkylaryl, said alkylaryl being optionally substituted at one or more positions with one or more of lower alkyl, —CN, halogen, —COOR$^{54}$, and —CH$_2$OR$^{54}$, wherein R$^{54}$ is alkyl or —H;
R$^{52}$ is lower alkyl or —H;
R$^{53}$ is H, alkyl, cycloalkyl, —COOR$^{55}$, —N(R$^{55}$)(R$^{56}$), —CH$_2$OH, —CN, —CONH$_2$, —CH$_2$OR$^{55}$ or —CONR$^{55}$R$^{56}$, wherein R$^{55}$ is independently selected from the group consisting of alkyl, —H, —C(O)-aryl, —C(O)-alkyl, or —C(O)-heteroaryl, and R$^{56}$ is selected from the group consisting of H, alkyl, —C(O)-aryl, —C(O)-alkyl, —C(O)-heteroaryl, alkylaryl and alkyl-heteroaryl, and wherein said aryl, heteroaryl, alkylaryl and alkyl-heteroaryl are optionally substituted at one or more positions with one or more of alkyl, —CN, halogen, —COOR$^{57}$, and —CH$_2$OR$^{57}$, wherein R$^{57}$ is lower alkyl or —H, or R$^{55}$ and R$^{56}$ together with the atom to which they are attached form a ring;
m is an integer selected from 0 to 2;
v is an integer selected from 0 to 4;
and pharmaceutically-acceptable salts and/or pharmaceutically-acceptable esters thereof.

3. The compound according to claim 1, wherein each of X$^1$, X$^2$, X$^3$, and X$^4$ is carbon.

4. The compound according to claim 1, wherein X$^1$ is nitrogen and each of X$^2$, X$^3$, and X$^4$ is carbon.

5. The compound according to claim 1, wherein n is 1, X$^2$ is carbon and R$^1$ is directly attached to the X$^2$ carbon.

6. The compound according to claim 5, wherein R$^1$ is selected from the group consisting of halogen, cyano, nitro, SO$_2$Me, lower alkyl, N(Me)$_2$, NHMe and piperidinyl.

7. The compound according to claim 6, wherein R$^1$ is halogen.

8. The compound according to claim 7, wherein R$^1$ is Cl.

9. The compound according to claim 1, wherein n is 2.

10. The compound according to claim 9, wherein each R$^1$ is halogen.

11. The compound according to claim 10, wherein X$^2$ is carbon, and one of the R$^1$ groups is directly attached to the X$^2$ carbon.

12. The compound according to claim 1, wherein k is 0.

13. The compound according to claim 1, wherein R$^3$ is H, halogen or methyl.

14. The compound according to claim 1, wherein R$^3$ is F or methyl.

15. The compound according to claim 1, wherein R$^4$ is aryl or heteroaryl, all being optionally substituted with from one to five substituents independently selected from the group consisting of halogen, alkyl, —OR$^{41}$, lower alkynyl, and NR$^{42}$R$^{43}$, wherein R$^{41}$ is lower alkyl or —H, R$^{42}$ and R$^{43}$ independently from each other are hydrogen or alkyl, or NR$^{42}$R$^{43}$ is piperidinyl or pyrrolidinyl, or R$^4$ is lower alkyl.

16. The compound according to claim 1, wherein R$^4$ is selected from the group consisting of napthyl, pyridinyl, methyl, phenyl or mono-or di-substituted phenyl, wherein the phenyl substituents are halogen, N(lower alkyl)$_2$ or OR$^{41}$.

17. The compound according to claim 1, wherein R$^4$ is phenyl, or mono- or di-substituted phenyl, wherein the one or more substituents are halogen.

18. The compound according to claim 1, wherein R$^4$ is phenyl, 4-chlorophenyl, 3-fluorophenyl, or 3,4-difluorophenyl.

19. The compound according to claim 1, wherein R$^4$ is phenyl, 3-bromophenyl or 3-dimethylaminophenyl.

20. The compound according to claim 1, wherein R$^5$ is selected from the group consisting of

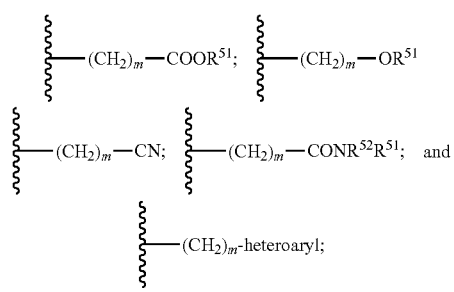

said heteroaryl being optionally substituted at one or more positions with one or more substituents independently selected from the group consisting of H, halogen, lower alkyl and $(CH_2)_vR^{53}$, wherein $R^{51}$ is selected from the group consisting of H, alkyl, allyl and alkylaryl, said alkylaryl being optionally substituted at one or more positions with one or more of lower alkyl, —CN, halogen, —COOR$^{54}$, and —CH$_2$OR$^{54}$, wherein $R^{54}$ is alkyl or —H;

$R^{52}$ is lower alkyl or —H;

$R^{53}$ is H, alkyl, cycloalkyl, —COOR$^{55}$, —N(R$^{55}$)(R$^{56}$), —CH$_2$OH, —CN, —CONH$_2$, —CH$_2$OR$^{55}$ or —CONR$^{55}$R$^{56}$, wherein R$^{55}$ is independently selected from the group consisting of alkyl, —H, —C(O)-aryl, —C(O)-alkyl, or —C(O)-heteroaryl, and R$^{56}$ is selected from the group consisting of H, alkyl, —C(O)-aryl, —C(O)-alkyl, —C(O)-heteroaryl, alkylaryl and alkyl-heteroaryl, and wherein said aryl, heteroarly, alkylaryl and alkyl-heteroaryl are optionally substituted at one or more positions with one or more of alkyl, —CN, halogen, —COOR$^{57}$, and —CH$_2$OR$^{57}$, wherein R$^{57}$ is lower alkyl or —H, or R$^{55}$ and R$^{56}$ together with the atom to which they are attached form a ring;

m is an integer selected from 0 to 2; and v is an integer selected from 0 to 4.

21. The compound according to claim 1, wherein m is 0.

22. The compound according to claim 19, wherein $R^5$ is selected from the group consisting of

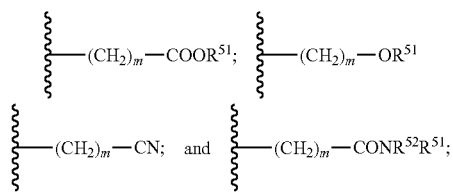

wherein $R^{5'}$ is selected from the group consisting of H, alkyl, allyl, alkylaryl optionally mono- or di-substituted at with one or more of lower alkyl, —CN, halogen, or —COOR$^{54}$, wherein $R^{54}$ is alkyl or —H; and $R^{52}$ is lower alkyl or H and , wherein m is an integer selected from 0 to 2.

23. The compound according to claim 20, wherein $R^5$ is selected from the group consisting of

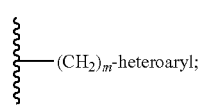

said heteroaryl being optionally substituted at one or more positions with one or more substituents independently selected from the group consisting of H, halogen, lower alkyl and $(CH_2)_vR^{53}$ and, wherein $R^{53}$ is aryl which can optionally be substituted with benzyloxy, carboxy, lower-alkoxy-carbonyl, hydroxyl-lower-alkyl, halogen, carbamoyl, lower-alkyl-carbamoyl, di-lower-alkyl-carbamoyl m is an integer selected from 0 to 2;

v is an integer selected from 0 to 4.

24. The compounds according to claim 23, wherein said heteroaryl is selected from the group consisting of

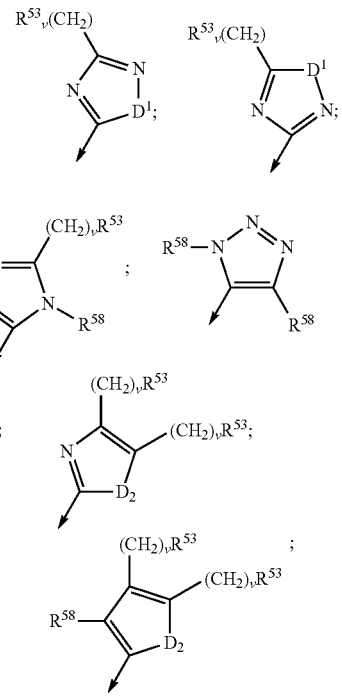

wherein v and $R^{53}$ are as defined in claim 19, $R^{58}$ is independently selected from H, halogen and lower alkyl, $D^1$ is O or S, and $D^2$ is O, S, or NR$^{58}$, and wherein, when said compound contains two $(CH_2)_vR^{53}$ groups, said groups may be optionally joined together along with the atoms to which they are attached to form a ring.

25. The compound according to claim 1, wherein $R^5$ is selected from the group consisting of

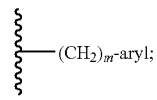

wherein aryl is selected from the group consisting of:

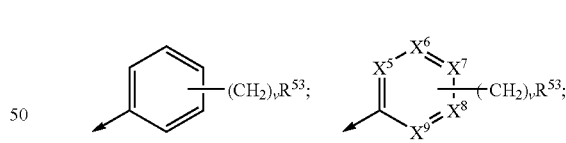

wherein $R^{53}$ is as described in claim 1, and wherein $X^5$, $X^6$, $X^7$, $X^8$ and $X^9$ are selected from carbon and nitrogen with the proviso that no more than two of $X^5$, $X^6$, $X^7$, $X^8$ and $X^9$ can be N at one time, and wherein m and v are defined as in claim 1.

26. The compound according to claim 24, wherein m is 0.

27. The compound according to claim 1, wherein $R^5$ is a heteroaryl selected from the group consisting of oxadiazolyl, oxazolyl and benzothiazolyl, which heteroaryl is optionally substituted with lower alkyl, lower alkoxy carbonyl or phenyl, which phenyl is optionally substituted with carboxy, lower alkyl carbonyl, carbamoyl or di (lower alkyl) carbamoyl.

28. The compound according to claim 26, wherein $R^5$ is 5-methyl-(1,3,4)oxadiazol-2-yl, 5-(4-benzoic acid methyl ester)-(1,3,4)oxadiazol-2-yl, 5-(4-benzoic acid)-(1,3,4)oxadiazol-2-yl, 5-(4-benzamide)-(1,3,4) oxadiazol-2-yl, 5-(4-dimethylbenzamide)-(1,3,4) oxadiazol-2-yl, 4-(carboxylic acid methyl ester)-oxazo-2-yl or benzothiazol-2-yl.

29. The compound according to claim 1, having the formula (Ia)

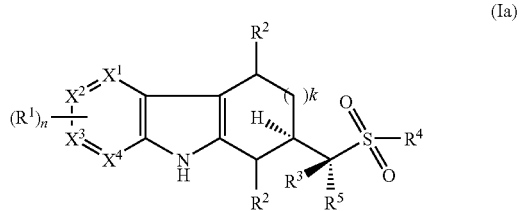

(Ia)

wherein $R^1$, $R^2$, $R^3$, $R^4$, $R^5$, n, k, $X^1$, $X^2$, $X^3$ and $X^4$ are as defined in any of claims 1 to 27.

30. The compound according to claim 1, having the formula (Ib)

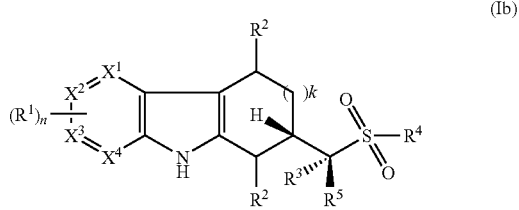

(Ib)

wherein $R^1$, $R^2$, $R^3$, $R^4$, $R^5$, n, k, $X^1$, $X^2$, $X^3$ and $X^4$ are as defined in any of claims 1 to 27.

31. The compound according to claim 1, wherein said compound is selected from the group consisting of
Benzenesulfonyl-(6-chloro-2,3,4,9-tetrahydro-1H-carbazol-2-yl)-acetic acid methyl ester;
Benzenesulfonyl-(6-fluoro-2,3,4,9-tetrahydro-1H-carbazol-2-yl)-acetic acid methyl ester;
(RS,SR)-2-Benzenesulfonyl-2-(6-chloro-2,3,4,9-tetrahydro-1H-carbazol-2-yl)-propionic acid methyl ester;
(RS,SR)-2-Benzenesulfonyl-2-(6-fluoro-2,3,4,9-tetrahydro-1H-carbazol-2-yl)-propionic acid methyl ester;
(RS,SR)-2-Benzenesulfonyl-2-(6-methyl-2,3,4,9-tetrahydro-1H-carbazol-2-yl)-propionic acid methyl ester;
(RS,SR)-2-Benzenesulfonyl-2-(6-nitro-2,3,4,9-tetrahydro-1H-carbazol-2-yl)-propionic acid methyl ester;
(RS,SR)-2-Benzenesulfonyl-2-(6-cyano-2,3,4,9-tetrahydro-1H-carbazol-2-yl)-propionic acid methyl ester;
(RS,SR)-2-Benzenesulfonyl-2-(2-chloro-6,7,8,9-tetrahydro-5H-pyrido[3,2-b]indol-7-yl)-propionic acid methyl ester;
(RS,SR)-2-Benzenesulfonyl-2-(2,3,4,9-tetrahydro-1H-carbazol-2-yl)-propionic acid methyl ester;
(RS,SR)-2-Benzenesulfonyl-2-(6-methanesulfonyl-2,3,4,9-tetrahydro-1H-carbazol-2-yl)-propionic acid methyl ester;
(RS,SR)-2-Benzenesulfonyl-2-(8-fluoro-2,3,4,9-tetrahydro-1H-carbazol-2-yl)-propionic acid methyl ester;
(RS,SR)-Benzenesulfonyl-(6-chloro-2,3,4,9-tetrahydro-1H-carbazol-2-yl)-fluoro-acetic acid methyl ester;
(RS,SR)-Benzenesulfonyl-fluoro-(6-methyl-2,3,4,9-tetrahydro-1H-carbazol-2-yl)-acetic acid methyl ester;
(RS,SR)-Benzenesulfonyl-(6-cyano-2,3,4,9-tetrahydro-1H-carbazol-2-yl)-fluoro-acetic acid methyl ester;
(RS,SR)-Benzenesulfonyl-(6-bromo-2,3,4,9-tetrahydro-1H-carbazol-2-yl)-fluoro-acetic acid methyl ester;
(RS,SR)-Benzenesulfonyl-(2-chloro-6,7,8,9-tetrahydro-5H-pyrido[3,2-b]indol-7-yl)-fluoro-acetic acid methyl ester;
(RS,SR)-Benzenesulfonyl-(6-bromo-7-fluoro-2,3,4,9-tetrahydro-1H-carbazol-2-yl)-fluoro-acetic acid methyl ester;
(RS,SR)-Benzenesulfonyl-(6-bromo-5-fluoro-2,3,4,9-tetrahydro-1H-carbazol-2-yl)-fluoro-acetic acid methyl ester;
(RS,SR)-2-Benzenesulfonyl-2-(7-chloro-1,2,3,4-tetrahydro-cyclopenta[b]indol-2-yl)-propionic acid methyl ester;
(RS,SR)-2-Benzenesulfonyl-2-(7-bromo-1,2,3,4-tetrahydro-cyclopenta[b]indol-2-yl)-propionic acid methyl ester;
(RS,SR)-2-Benzenesulfonyl-2-(7-cyano-1,2,3,4-tetrahydro-cyclopenta[b]indol-2-yl)-propionic acid methyl ester;
(RS,SR)-2-Benzenesulfonyl-2-(7-methyl-1,2,3,4-tetrahydro-cyclopenta[b]indol-2-yl)-propionic acid methyl ester;
(RS,SR)-Benzenesulfonyl-(7-chloro-1,2,3,4-tetrahydro-cyclopenta[b]indol-2-yl)-fluoro-acetic acid methyl ester;
(RS,SR)-Benzenesulfonyl-(7-bromo-1,2,3,4-tetrahydro-cyclopenta[b]indol-2-yl)-fluoro-acetic acid methyl ester;
(RS,SR)-Benzenesulfonyl-(5-chloro-1,2,3,8-tetrahydro-4,8-diaza-cyclopenta[a]inden-2-yl)-fluoro-acetic acid methyl ester;
(RS,SR)-Benzenesulfonyl-(7-bromo-6-fluoro-1,2,3,4-tetrahydro-cyclopenta[b]indol-2-yl)-fluoro-acetic acid methyl ester;
(RS,SR)-Benzenesulfonyl-(7-bromo-8-fluoro-1,2,3,4-tetrahydro-cyclopenta[b]indol-2-yl)-fluoro-acetic acid methyl ester;
(RS,SR)-2-(6-Chloro-2,3,4,9-tetrahydro-1H-carbazol-2-yl)-2-(naphthalene-1-sulfonyl)-propionic acid methyl ester;
(RS,SR)-2-(6-Chloro-2,3,4,9-tetrahydro-1H-carbazol-2-yl)-2-(naphthalene-2-sulfonyl)-propionic acid methyl ester;
(RS,SR)-2-(6-Chloro-2,3,4,9-tetrahydro-1H-carbazol-2-yl)-2-(3,4-dichloro-benzenesulfonyl)-propionic acid methyl ester;
(RS,SR)-2-(6-Chloro-2,3,4,9-tetrahydro-1H-carbazol-2-yl)-2-(toluene-3-sulfonyl)-propionic acid methyl ester;
(RS,SR)-2-(6-Chloro-2,3,4,9-tetrahydro-1H-carbazol-2-yl)-2-(3-methoxy-benzenesulfonyl)-propionic acid methyl ester;
(RS,SR)-2-(2-Chloro-benzenesulfonyl)-2-(6-chloro-2,3,4,9-tetrahydro-1H-carbazol-2-yl)-propionic acid methyl ester;
(RS,SR)-2-(6-Chloro-2,3,4,9-tetrahydro-1H-carbazol-2-yl)-2-(2-methoxy-benzenesulfonyl)-propionic acid methyl ester;
(RS,SR)-2-(6-Chloro-2,3,4,9-tetrahydro-1H-carbazol-2-yl)-2-(4-fluoro-benzenesulfonyl)-propionic acid methyl ester;
(RS,SR)-2-(3-Chloro-benzenesulfonyl)-2-(6-chloro-2,3,4,9-tetrahydro-1H-carbazol-2-yl)-propionic acid methyl ester;
(RS,SR)-(6-Chloro-2,3,4,9-tetrahydro-1H-carbazol-2-yl)-fluoro-(4-fluoro-benzenesulfonyl)-acetic acid methyl ester;

(RS,SR)-(3-Chloro-benzenesulfonyl)-(6-chloro-2,3,4,9-tetrahydro-1H-carbazol-2-yl)-fluoro-acetic acid methyl ester;
(RS,SR)-(6-Chloro-2,3,4,9-tetrahydro-1H-carbazol-2-yl)-fluoro-(3-fluoro-benzenesulfonyl)-acetic acid methyl ester;
(RS,SR)-(6-Chloro-2,3,4,9-tetrahydro-1H-carbazol-2-yl)-(3,4-difluoro-benzenesulfonyl)-fluoro-acetic acid methyl ester;
(RS,SR)-(6-Chloro-2,3,4,9-tetrahydro-1H-carbazol-2-yl)-fluoro-(pyridine-3-sulfonyl)-acetic acid methyl ester;
(RS,SR)-(7-Chloro-1,2,3,4-tetrahydro-cyclopenta[b]indol-2-yl)-fluoro-(3-methoxy-benzenesulfonyl)-acetic acid methyl ester;
(RS,SR)-(3-Chloro-benzenesulfonyl)-(7-chloro-1,2,3,4-tetrahydro-cyclopenta[b]indol-2-yl)-fluoro-acetic acid methyl ester;
(RS,SR)-(7-Chloro-1,2,3,4-tetrahydro-cyclopenta[b]indol-2-yl)-fluoro-(pyridine-2-sulfonyl)-acetic acid methyl ester;
(RS,SR)-(7-Chloro-1,2,3,4-tetrahydro-cyclopenta[13]indol-2-yl)-fluoro-(3-fluoro-benzenesulfonyl)-acetic acid methyl ester;
(RS,SR)-(7-Chloro-1,2,3,4-tetrahydro-cyclopenta[b]indol-2-yl)-(3,4-difluoro-benzenesulfonyl)-fluoro-acetic acid methyl ester;
(RS,SR)-(7-Chloro-1,2,3,4-tetrahydro-cyclopenta[b]indol-2-yl)-fluoro-(pyridine-3-sulfonyl)-acetic acid methyl ester;
(RS,SR)-2-(7-Chloro-1,2,3,4-tetrahydro-cyclopenta[b]indol-2-yl)-2-(pyridine-2-sulfonyl)-propionic acid methyl ester;
(RS,SR)-2-Benzenesulfonyl-2-(6-chloro-2,3,4,9-tetrahydro-1H-carbazol-2-yl)-propionic acid;
(RS,SR)-Benzenesulfonyl-(6-chloro-2,3,4,9-tetrahydro-1H-carbazol-2-yl)-fluoro-acetic acid;
(RS,SR)-2-(1-Benzenesulfonyl-2-methoxy-1-methyl-ethyl)-6-chloro-2,3,4,9-tetrahydro-1H-carbazole;
(RS,SR)-2-Benzenesulfonyl-2-(6-methyl-2,3,4,9-tetrahydro-1H-carbazol-2-yl)-propionitrile;
(RS,SR)-2-Benzenesulfonyl-2-(6-chloro-2,3,4,9-tetrahydro-1H-carbazol-2-yl)-propionitrile;
(RS,SR)-Benzenesulfonyl-(6-chloro-2,3,4,9-tetrahydro-1H-carbazol-2-yl)-fluoro-acetonitrile;
(RS,SR)-2-Benzenesulfonyl-2-(6-chloro-2,3,4,9-tetrahydro-1H-carbazol-2-yl)-2-fluoro-N-methyl-acetamide;
(RS,SR)-2-Benzenesulfonyl-2-(7-chloro-1,2,3,4-tetrahydro-cyclopenta[b]indol-2-yl)-2-fluoro-N-methyl-acetamide;
(RS,SR)-2-(6-Chloro-2,3,4,9-tetrahydro-1H-carbazol-2-yl)-2-fluoro-2-(3-fluoro-benzenesulfonyl)-N-methyl-acetamide;
(RS,SR)-2-(7-Chloro-1,2,3,4-tetrahydro-cyclopenta[b]indol-2-yl)-2-fluoro-2-(3-fluoro-benzenesulfonyl)-N-methyl-acetamide;
(RS,SR)-2-Benzenesulfonyl-2-(6-chloro-2,3,4,9-tetrahydro-1H-carbazol-2-yl)-2-fluoro-N,N-dimethyl-acetamide;
(RS,SR)-2-Benzenesulfonyl-2-(7-chloro-1,2,3,4-tetrahydro-cyclopenta[b]indol-2-yl)-2-fluoro-N,N-dimethyl-acetamide;
(RS,SR)-2-(6-Chloro-2,3,4,9-tetrahydro-1H-carbazol-2-yl)-2-fluoro-2-(3-fluoro-benzenesulfonyl)-N,N-dimethyl-acetamide;
(RS,SR)-2-(7-Chloro-1,2,3,4-tetrahydro-cyclopenta[b]indol-2-yl)-2-fluoro-2-(3-fluoro-benzenesulfonyl)-N,N-dimethyl-acetamide;
(RS,SR)-2-Benzenesulfonyl-N-benzyl-2-(6-chloro-2,3,4,9-tetrahydro-1H-carbazol-2-yl)-2-fluoro-N-methyl-acetamide;
(RS,SR)-2-Benzenesulfonyl-2-(6-chloro-2,3,4,9-tetrahydro-1H-carbazol-2-yl)-N-(4-cyano-benzyl)-2-fluoro-N-methyl-acetamide;
(RS,SR)-2-Benzenesulfonyl-N-(4-bromo-benzyl)-2-(6-chloro-2,3,4,9-tetrahydro-1H-carbazol-2-yl)-2-fluoro-N-methyl-acetamide;
(RS,SR)-2-Benzenesulfonyl-2-(6-chloro-2,3,4,9-tetrahydro-1H-carbazol-2-yl)-N-(3,5-difluoro-benzyl)-2-fluoro-N-methyl-acetamide;
(RS,SR)-4-({[2-Benzenesulfonyl-2-(6-chloro-2,3,4,9-tetrahydro-1H-carbazol-2-yl)-2-fluoro-acetyl]-methyl-amino}-methyl)-benzoic acid methyl ester;
(RS,SR)-3-({[2-Benzenesulfonyl-2-(6-chloro-2,3,4,9-tetrahydro-1H-carbazol-2-yl)-2-fluoro-acetyl]-methyl-amino}-methyl)-benzoic acid methyl ester;
(RS,SR)-2-Benzenesulfonyl-2-(6-chloro-2,3,4,9-tetrahydro-1H-carbazol-2-yl)-N-(2-cyano-benzyl)-2-fluoro-N-methyl-acetamide;
(RS,SR)-N-Allyl-2-benzenesulfonyl-2-(6-chloro-2,3,4,9-tetrahydro-1H-carbazol-2-yl)-2-fluoro-N-methyl-acetamide;
(RS,SR)-2-Benzenesulfonyl-2-(6-chloro-2,3,4,9-tetrahydro-1H-carbazol-2-yl)-N-(3-cyano-benzyl)-2-fluoro-N-methyl-acetamide;
(RS,SR)-3-({[2-Benzenesulfonyl-2-(6-chloro-2,3,4,9-tetrahydro-1H-carbazol-2-yl)-2-fluoro-acetyl]-methyl-amino}-methyl)-benzoic acid;
(RS,SR)-2-Benzenesulfonyl-2-(6-chloro-2,3,4,9-tetrahydro-1H-carbazol-2-yl)-2-fluoro-N-(3-hydroxymethyl-benzyl)-N-methyl-acetamide;
(RS,SR)-2-[Benzenesulfonyl-fluoro-(5-methyl-[1,3,4]oxadiazol-2-yl)-methyl]-7-chloro-1,2,3,4-tetrahydro-cyclopenta[b]indole;
(S)-2-[(R)-Benzenesulfonyl-fluoro-(5-methyl-[1,3,4]oxadiazol-2-yl)-methyl]-7-chloro-1,2,3,4-tetrahydro-cyclopenta[b]indole;
(R)-2-[(S)-Benzenesulfonyl-fluoro-(5-methyl-[1,3,4]oxadiazol-2-yl)-methyl]-7-chloro-1,2,3,4-tetrahydro-cyclopenta[b]indole;
(RS,SR)-2-[1-Benzenesulfonyl-1-(5-methyl-[1,3,4]oxadiazol-2-yl)-ethyl]-7-chloro-1,2,3,4-tetrahydro-cyclopenta[b]indole;
(RS,SR)-2-(Benzenesulfonyl-fluoro-[1,3,4]oxadiazol-2-yl-methyl)-7-chloro-1,2,3,4-tetrahydro-cyclopenta[b]indole;
(RS,SR)-2-[Benzenesulfonyl-(5-cyclopropyl-[1,3,4]oxadiazol-2-yl)-fluoro-methyl]-7-chloro-1,2,3,4-tetrahydro-cyclopenta[b]indole;
(RS,SR)-2-[Benzenesulfonyl-(5-cyclopropyl-[1,3,4]oxadiazol-2-yl)-fluoro-methyl]-6-chloro-2,3,4,9-tetrahydro-1H-carbazole;
(RS,SR)-{5-[Benzenesulfonyl-(7-chloro-1,2,3,4-tetrahydro-cyclopenta[b]indol-2-yl)-fluoro-methyl]-[1,3,4]oxadiazol-2-yl}-dimethyl-amine;
(RS,SR)-{5-[Benzenesulfonyl-(7-chloro-1,2,3,4-tetrahydro-cyclopenta[b]indol-2-yl)-fluoro-methyl]-[1,3,4]oxadiazol-2-yl}-dimethyl-amine;
(RS,SR)-2-[Benzenesulfonyl-fluoro-(3-methyl-[1,2,4]oxadiazol-5-yl)-methyl]-7-chloro-1,2,3,4-tetrahydro-cyclopenta[b]indole;

(RS,SR)-5-[Benzenesulfonyl-(7-chloro-1,2,3,4-tetrahydro-cyclopenta[b]indol-2-yl)-fluoro-methyl ]-[1,2,4]oxadiazole-3-carboxylic acid methyl ester;
(RS,SR)-{5-[Benzenesulfonyl-(7-chloro-1,2,3,4-tetrahydro-cyclopent[b]indol-2-yl)-fluoro-methyl ]-[1,2,4]oxadiazol-3-yl}-methanol;
(RS,SR)-5-[Benzenesulfonyl-(7-chloro-1,2,3,4-tetrahydro-cyclopenta[b]indol-2-yl)-fluoro-methyl ]-[1,2,4]oxadiazole-3-carboxylic acid;
(RS,SR)-5-[Benzenesulfonyl-(7-chloro-1,2,3,4-tetrahydro-cyclopenta[b]indol-2-yl)-fluoro-methyl ]-[1,2,4]oxadiazole-3-carboxylic acid amide;
(RS,SR)-{5-[Benzenesulfonyl-(7-chloro-1,2,3,4-tetrahydro-cyclopenta[b]indol-2-yl)-fluoro-methyl ]-[1,2,4]oxadiazol-3-yl}-dimethyl-amine;
(RS,SR)-7-Chloro-2-[(3-chloro-benzenesulfonyl)-fluoro-(3-methyl-[1,2,4]oxadiazol-5-yl)-methyl ]-1,2,3,4-tetrahydro-cyclopenta[b]indole;
(RS,SR)-7-Chloro-2-[(3-chloro-benzenesulfonyl)-fluoro-(5-methyl-[1,3,4]oxadiazol-2-yl)-methyl ]-1,2,3,4-tetrahydro-cyclopenta[b]indole;
(RS,SR)-2-{5-[Benzenesulfonyl-(7-chloro-1,2,3,4-tetrahydro-cyclopenta[b ]indol-2-yl)-fluoro-methyl ]-[1,2,4]oxadiazol-3-ylmethyl}-isoindole-1,3-dione;
(RS,SR)-C-{5-[Benzenesulfonyl-(7-chloro-1,2,3,4-tetrahydro-cyclopenta[b ]indol-2-yl)-fluoro-methyl ]-[1,2,4]oxadiazol-3-yl}-methylamine;
(RS,SR)-{5-[Benzenesulfonyl-(7-chloro-1,2,3,4-tetrahydro-cyclopenta[b]indol-2-yl)-fluoro-methyl ]-[1,2,4]oxadiazol-3-ylmethyl}-dimethyl-amine;
(RS,SR)-{5-[Benzenesulfonyl-(7-chloro-1,2,3,4-tetrahydro-cyclopenta[b]indol-2-yl)-fluoro-methyl ]-[1,2,4]oxadiazol-3-ylmethyl}-diethyl-amine;
(RS,SR)-{5-[Benzenesulfonyl-(7-chloro-1,2,3,4-tetrahydro-cyclopenta[b]indol-2-yl)-fluoro-methyl ]-[1,2,4]oxadiazol-3-ylmethyl}-diethyl-amine;
(RS,SR)-2-(Benzenesulfonyl-benzooxazol-2-yl-fluoro-methyl)-7-chloro-1,2,3,4-tetrahydro-cyclopenta [b]indole;
(RS,SR)-N-{5-[Benzenesulfonyl-(7-chloro-1,2,3,4-tetrahydro-cyclopenta[b]indol-2-yl)-fluoro-methyl ]-[1,2,4]oxadiazol-3-ylmethyl}-acetamide;
(RS,SR)-N-{5-[Benzenesulfonyl-(7-chloro-1,2,3,4-tetrahydro-cyclopenta[b]indol-2-yl)-fluoro-methyl ]-[1,2,4]oxadiazol-3-ylmethyl}-benzamide;
(RS,SR)-2-Benzenesulfonyl-2-(6-bromo-2,3,4,9-tetrahydro-1H-carbazol-2-yl)-propionic acid methyl ester;
(RS,SR)-2-Benzenesulfonyl-2-(6-dimethylamino-2,3,4,9-tetrahydro-1H-carbazol-2-yl)-propionic acid methyl ester;
(6-Bromo-2,3,4,9-tetrahydro-1H-carbazol-2-yl)-methanesulfonyl-acetic acid methyl ester (RS,SR)-2-(6-Bromo-2,3,4,9-tetrahydro-1H-carbazol-2-yl)-2-methanesulfonyl-propionic acid methyl ester;
(RS,SR)-2-(6-Dimethylamino-2,3,4,9-tetrahydro-1H-carbazol-2-yl)-2-methanesulfonyl-propionic acid methyl ester;
and pharmaceutically-acceptable salts and/or pharmaceutically-acceptable esters thereof.

32. The compound according to claim 1, wherein said compound is selected from the group consisting of
(RS,SR)-2-Benzenesulfonyl-2-(6-bromo-2,3,4,9-tetrahydro-1H-carbazol-2-yl)-propionic acid methyl ester;
(RS,SR)-Benzenesulfonyl-(6-chloro-2,3,4,9-tetrahydro-1H-carbazol-2-yl)-fluoro-acetic acid methyl ester;
(RS,SR)-2-Benzenesulfonyl-2-(7-chloro-1,2,3,4-tetrahydro-cyclopenta [b]indol-2-yl)-propionic acid methyl ester;
(RS,SR)-Benzenesulfonyl-(7-chloro-1,2,3,4-tetrahydro-cyclopenta PA indol-2-yl)-fluoro-acetic acid methyl ester;
(RS,SR)-Benzenesulfonyl-(7-bromo-8-fluoro-1,2,3,4-tetrahydro-cyclopenta [b]indol-2-yl)-fluoro-acetic acid methyl ester;
(RS,SR)-(3-Chloro-benzenesulfonyl)-(7-chloro-1,2,3,4-tetrahydro-cyclopenta [b]indol-2-yl)-fluoro-acetic acid methyl ester;
(RS,SR)-(7-Chloro-1,2,3,4-tetrahydro-cyclopenta[b]indol-2-yl)-fluoro-(3-fluoro-benzenesulfonyl)-acetic acid methyl ester;
(RS,SR)-(7-Chloro-1,2,3,4-tetrahydro-cyclopenta[b]indol-2-yl)-(3,4-difluoro-benzenesulfonyl)-fluoro-acetic acid methyl ester;
(RS,SR)-2-(6-Chloro-2,3,4,9-tetrahydro-1H-carbazol-2-yl)-2-fluoro-2-(3-fluoro-benzenesulfonyl)-N,N-dimethyl-acetamide;
(RS,SR)-2-[Benzenesulfonyl-fluoro-(5-methyl-[1,3,4]oxadiazol-2-yl)-methyl]-7-chloro-1,2,3,4-tetrahydro-cyclopenta [b]indole;
(S)-2-[(R)-Benzenesulfonyl-fluoro-(5-methyl-[1,3,4]oxadiazol-2-yl)-methyl]-7-chloro-1,2,3,4-tetrahydro-cyclopenta [b]indole;
(R)-2-[(S)-Benzenesulfonyl-fluoro-(5-methyl-[1,3,4]oxadiazol-2-yl)-methyl]-7-chloro-1,2,3,4-tetrahydro-cyclopenta [b]indole;
(RS,SR)-2-[Benzenesulfonyl-(5-cyclopropyl-[1,3,4]oxadiazol-2-yl)-fluoro-methyl]-7-chloro-1,2,3,4-tetrahydro-cyclopenta[b]indole;
(RS,SR)-{5-[Benzenesulfonyl-(7-chloro-1,2,3,4-tetrahydro-cyclopenta[b]indol-2-yl)-fluoro-methyl ]-[1,3,4]oxadiazol-2-yl}-dimethyl-amine;
(RS,SR)-2-[Benzenesulfonyl-fluoro-(3-methyl-[1,2,4]oxadiazol-5-yl)-methyl]-7-chloro-1,2,3,4-tetrahydro-cyclopenta [b]indole;
(RS,SR)-{5-[Benzenesulfonyl-(7-chloro-1,2,3,4-tetrahydro-cyclopenta[b]indol-2-yl)-fluoro-methyl ]-[1,2,4]oxadiazol-3-yl}-dimethyl-amine;
and pharmaceutically-acceptable salts and/or pharmaceutically-acceptable esters thereof.

33. The compound according to claim 1, wherein said compound is selected from the group consisting of
(3-bromo-benzenesulfonyl)-(7-chloro-1,2,3,4-tetrahydro-cyclopenta [b]indol-2-yl)-acetic acid methyl ester;
(RS, SR)-2-(3-bromo-benzenesulfonyl)-2-(7-chloro-1,2,3,4-tetrahydro-cyclopenta[b]indol-2-yl)-propionic acid methyl ester;
(RS, SR)-(7-chloro-1,2,3,4-tetrahydro-cyclopenta[b]indol-2-yl)-2-(3-pyrrolidin-1-yl-benzenesulfonyl)-propionic acid methyl ester;
(RS, SR) 2-[1-(3-bromo-benzenesulfonyl)-1-(5-methyl-[1,3,4]oxadiazol-2-yl)-ethyl]-7-chloro-1,2,3,4-tetrahydro-cyclopenta[b]indole;
(RS, SR)-2-[(3-bromo-benzenesulfonyl)-fluoro-(5-methyl-[1,3,4]oxadiazol-2-yl)-methyl]-7-chloro-1,2,3,4-tetrahydro-cyclopenta[b]indole;
(RS, SR) 2-[(5-benzyl-[1,3,4]oxadiazol-2-yl)-(3-bromo-benzenesulfonyl)-fluoro-methyl]-7-chloro-1,2,3,4-tetrahydro-cyclopenta[b]indole;
(RS, SR) {3-[(7-chloro-1,2,3,4-tetrahydro-cyclopenta[b]indol-2-yl)-fluoro-(5-methyl-[1,3,4]oxadiazol-2-yl)-methanesulfonyl]-phenyl}-dimethyl-amine;

(RS, SR)-7-chloro-2-[(3-ethynyl-benzenesulfonyl)-fluoro-(5-methyl-[1,3,4]oxadiazol-2-yl)-methyl]-1,2,3,4-tetrahydro-cyclopenta[b]indole;

(RS, SR)-2-[5-(4-benzyloxy-benzyl)-[1,3,4]oxadiazol-2-yl-(3-bromo-benzenesulfonyl)-fluoro-methyl]-7-chloro-1,2,3,4-tetrahydro-cyclopenta[b]indole;

(RS, SR)-7-chloro-2-[(3-ethyl-benzenesulfonyl)-fluoro-(5-methyl-[1,3,4]oxadiazol-2-yl)-methyl]-1,2,3,4-tetrahydro-cyclopenta[b]indole;

(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzoic acid methyl ester;

(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzoic acid;

(RS, SR) (4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-phenyl)-methanol;

(RS, SR) 2-{benzenesulfonyl-fluoro-[5-(4-iodo-benzyl)-[1,3,4]oxadiazol-2-yl]-methyl}-7-chloro-1,2,3,4-tetrahydro-cyclopenta[b]indole;

(RS, SR) 4-{5-[(benzenesulfonyl)-(7-chloro-1,2,3,4-tetrahydro-cyclopenta[b]indol-2-yl)-fluoro-methyl]-[1,3,4]oxadiazol-2-yl}-benzoic acid;

(RS, SR) 4-{5-[benzenesulfonyl-(7-chloro-1,2,3,4-tetrahydro-cyclopenta[b]indol-2-yl)-fluoro-methyl]-[1,3,4]oxadiazol-2-ylmethyl}-benzoic acid;

(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzamide;

(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-N-methyl-benzamide;

(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-N,N-dimethyl-benzamide;

(RS,SR)-2-[-benzenesulfonyl-fluoro-(5-methyl-[1,3,4]oxadiazol-2-yl)-methyl]-7-bromo-1,2,3,4-tetrahydro-cyclopenta[b]indole;

(RS,SR)-2-[-benzenesulfonyl-fluoro-(5-methyl-[1,3,4]oxadiazol-2-yl)-methyl]-7-piperidin-1-yl-1,2,3,4-tetrahydro-cyclopenta[b]indole;

(RS,SR)-N-{2-[-benzenesulfonyl-fluoro-(5-methyl-[1,3,4]oxadiazol-2-yl)-methyl]-1,2,3,4-tetrahydro-cyclopenta[b]indol-7-yl}-N-methyl-amine;

2-[benzenesulfonyl-fluoro-(5-trifluoromethyl-[1,3,4]oxadiazol-2-yl)-methyl]-7-chloro-1,2,3,4-tetrahydro-cyclopenta[b]indole;

(RS,SR)-2-(1-benzenesulfonyl-2-methoxy-1-methyl-ethyl)-7-chloro-1,2,3,4-tetrahydro-cyclopenta [b]indole;

(RS,SR)-2-benzenesulfonyl-2-(-6-chloro-2,3,4,9-tetrahydro-1H-carbazol-2-yl)-2-fluoro-N-methyl-N-(3-methyl-but-2-enyl)-acetamide;

(RS,SR)-5-[-benzenesulfonyl-(-7-chloro-1,2,3,4-tetrahydro-cyclopenta[b]indol-2-yl)-fluoro-methyl]-[1,2,4]oxadiazole-3-carbonitrile;

(RS,SR)-{5-[-benzenesulfonyl-(-6-chloro-2,3,4,9-tetrahydro-1H-carbazol-2-yl)-fluoro-methyl]-[1,2,4]oxadiazol-3-yl}-dimethyl-amine;

(RS,SR)-4-[({5-[-benzenesulfonyl-(-7-chloro-1,2,3,4-tetrahydro-cyclopenta[b]indol-2-yl)-fluoro-methyl]-[1,2,4]oxadiazol-3-ylmethyl}-amino)-methyl]-benzoic acid methyl ester;

(RS,SR)-3-[({5-[-benzenesulfonyl-(-7-chloro-1,2,3,4-tetrahydro-cyclopenta[b]indol-2-yl)-fluoro-methyl]-[1,2,4]oxadiazol-3-ylmethyl}-amino)-methyl]-benzoic acid methyl ester;

(RS,SR)-{4-[({5-[-benzenesulfonyl-(-7-chloro-1,2,3,4-tetrahydro-cyclopenta[b]indol-2-yl)-fluoro-methyl]-[1,2,4]oxadiazol-3-ylmethyl}-amino)-methyl]-phenyl}-methanol;

(RS,SR)-2-(benzenesulfonyl-pyridin-2-yl-methyl)-7-chloro-1,2,3,4-tetrahydro-cyclopenta [b]indole;

(RS,SR)-N-{5-[(S)-benzenesulfonyl-((R)-7-chloro-1,2,3,4-tetrahydro-cyclopenta[b]indol-2-yl)-fluoro-methyl]-[1,2,4]oxadiazol-3-ylmethyl}-2,2,2-trifluoro-acetamide 2-[benzenesulfonyl-fluoro-(3-phenyl-[1,2,4]oxadiazol-5-yl)-methyl]-7-chloro-1,2,3,4-tetrahydro-cyclopenta [b]indole;

(RS,SR)-2-[-benzenesulfonyl-(-7-chloro-1,2,3,4-tetrahydro-cyclopenta[b]indol-2-yl)-fluoro-methyl]-oxazole-4-carboxylic acid methyl ester;

2-(benzenesulfonyl-benzothiazol-2-yl-fluoro-methyl)-7-chloro-1,2,3,4-tetrahydro-cyclopenta [b]indole;

(RS,SR)-2-[-benzenesulfonyl-(4,5-dimethyl-oxazol-2-yl)-methyl]-7-chloro-1,2,3,4-tetrahydro-cyclopenta [b]indole;

and pharmaceutically acceptable salts and/or pharmaceutically acceptable esters thereof.

34. The compound according to claim 1, wherein said compound is selected from the group consisting of (RS, SR)-2-[(3-bromo-benzenesulfonyl)-fluoro-(5-methyl-[1,3,4]oxadiazol-2-yl)-methyl]-7-chloro-1,2,3,4-tetrahydro-cyclopenta[b]indole;

(RS, SR) {3-[(7-chloro-1,2,3,4-tetrahydro-cyclopenta[b]indol-2-yl)-fluoro-(5-methyl-[1,3,4]oxadiazol-2-yl)-methanesulfonyl]-phenyl}-dimethyl-amine;

(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzoic acid methyl ester;

(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzoic acid;

(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-benzamide;

(RS, SR) 4-{5-[(3-bromo-benzenesulfonyl)-(7-chloro-1,2,3,4-tetrahydro-cyclopenta[b]indol-2-yl)-fluoro-methyl]-[1,3,4]oxadiazol-2-yl}-N,N-dimethyl-benzamide;

(RS,SR)-2-[-benzenesulfonyl-(-7-chloro-1,2,3,4-tetrahydro-cyclopenta[b]indol-2-yl)-fluoro-methyl]-oxazole-4-carboxylic acid methyl ester;

2-(benzenesulfonyl-benzothiazol-2-yl-fluoro-methyl)-7-chloro-1,2,3,4-tetrahydro-cyclopenta [b]indole;

and pharmaceutically-acceptable salts and/or pharmaceutically-acceptable esters thereof.

35. A pharmaceutical composition comprising a compound according to claim 1 and a pharmaceutically acceptable carrier and/or adjuvant.

* * * * *